United States Patent
Sciascia

(10) Patent No.: US 11,660,296 B2
(45) Date of Patent: *May 30, 2023

(54) TREATMENT OF CHRONIC COUGH, BREATHLESSNESS AND DYSPNEA

(71) Applicant: TREVI THERAPEUTICS, INC., New Haven, CT (US)

(72) Inventor: Thomas Sciascia, Belmont, MA (US)

(73) Assignee: Trevi Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/702,995

(22) Filed: Mar. 24, 2022

(65) Prior Publication Data

US 2022/0218697 A1 Jul. 14, 2022

Related U.S. Application Data

(63) Continuation of application No. 17/576,208, filed on Jan. 14, 2022, which is a continuation of application No. 17/341,936, filed on Jun. 8, 2021, now abandoned, which is a continuation of application No. 17/085,098, filed on Oct. 30, 2020, now abandoned, which is a continuation of application No. 16/810,317, filed on Mar. 5, 2020, now abandoned, which is a continuation of application No. 16/519,831, filed on Jul. 23, 2019, now abandoned.

(60) Provisional application No. 62/701,902, filed on Jul. 23, 2018.

(51) Int. Cl.
| | | |
|---|---|---|
| *A61K 31/485* | (2006.01) | |
| *A61K 45/06* | (2006.01) | |
| *A61K 9/20* | (2006.01) | |
| *A61P 11/14* | (2006.01) | |

(52) U.S. Cl.
CPC ............ *A61K 31/485* (2013.01); *A61K 9/205* (2013.01); *A61K 9/2009* (2013.01); *A61K 9/2013* (2013.01); *A61K 9/2018* (2013.01); *A61K 9/2054* (2013.01); *A61K 45/06* (2013.01); *A61P 11/14* (2018.01)

(58) Field of Classification Search
CPC combination set(s) only.
See application file for complete search history.

(56) References Cited

U.S. PATENT DOCUMENTS

| | | |
|---|---|---|
| 4,443,442 A | 4/1984 | Skillern |
| 4,720,384 A | 1/1988 | Di Luccio et al. |
| 5,760,023 A | 6/1998 | Farrar et al. |
| 5,855,913 A | 1/1999 | Hanes et al. |
| 5,874,064 A | 2/1999 | Edwards et al. |
| 6,156,769 A | 12/2000 | Farrar et al. |
| 6,174,891 B1 | 1/2001 | Nagase et al. |
| 6,316,461 B1 | 11/2001 | Nagase et al. |
| 6,451,806 B2 | 9/2002 | Farrar |
| 6,565,885 B1 | 5/2003 | Tarara et al. |
| 6,787,149 B1 | 9/2004 | El Khoury et al. |
| 6,946,117 B1 | 9/2005 | Schutt et al. |
| 6,984,493 B1 | 1/2006 | Kumagai et al. |
| 7,056,500 B2 | 6/2006 | Bentley et al. |
| 7,563,899 B2 | 7/2009 | Boyd et al. |
| 7,884,102 B2 | 2/2011 | Dolle et al. |
| 8,105,590 B2 | 1/2012 | Yao et al. |
| 8,309,596 B2 | 11/2012 | Flohr et al. |
| 8,394,812 B2 | 3/2013 | Baichwal et al. |
| 8,476,318 B2 | 7/2013 | Schmaus et al. |
| 8,637,538 B1 | 1/2014 | Sciascia |
| 8,940,753 B1 | 1/2015 | Sciascia |
| 8,987,289 B2 | 3/2015 | Sciascia |
| 2001/0006967 A1 | 7/2001 | Crain et al. |
| 2001/0047005 A1 | 11/2001 | Farrar |
| 2002/0013296 A1 | 1/2002 | Zhang et al. |
| 2003/0054030 A1 | 3/2003 | Gordon |
| 2003/0191147 A1 | 10/2003 | Sherman et al. |
| 2004/0157913 A1 | 8/2004 | Jacob et al. |
| 2004/0171631 A1 | 9/2004 | Hu et al. |
| 2004/0241101 A1 | 12/2004 | Baran, Jr. et al. |
| 2004/0266806 A1 | 12/2004 | Sanghvi et al. |
| 2005/0182258 A1 | 8/2005 | Schmidhammer et al. |
| 2006/0063792 A1 | 3/2006 | Dolle et al. |
| 2006/0194826 A1 | 8/2006 | Oshlack et al. |
| 2007/0048376 A1 | 3/2007 | Baichwal et al. |
| 2007/0060501 A1 | 3/2007 | Jhamandas et al. |
| 2007/0099946 A1 | 5/2007 | Doshan et al. |
| 2008/0160092 A1 | 7/2008 | Batycky et al. |
| 2008/0176884 A1 | 7/2008 | Perez et al. |
| 2008/0207667 A1 | 8/2008 | Rhame |

(Continued)

FOREIGN PATENT DOCUMENTS

| | | |
|---|---|---|
| CN | 1214634 A | 4/1999 |
| CN | 1370082 A | 9/2002 |

(Continued)

OTHER PUBLICATIONS

Manen (Cough in idiopathic pulmonary fibrosis, Review in cough, Eur Respir Rev 2016; 25: 278-286).*
Hawi (Pharmacokinetics of nalbuphine hydrochloride extended release tablets in hemodialysis patients with exploratory effect on pruritus, BMC Nephrology (2015) 16:47, pp. 2-10).*
International Search Report and Written Opinion in International Application No. PCT/US2013/075096, dated Apr. 14, 2014, 7 pages.
International Preliminary Report on Patentability in International Application No. PCT/US2013/075096, dated Jun. 16, 2015, 6 pages.
International Search Report and Written Opinion in International Application No. PCT/US2015/035650, dated Sep. 4, 2015, 9 pages.

(Continued)

Primary Examiner — Kathrien A Hartsfield
(74) Attorney, Agent, or Firm — Cooley LLP

(57) ABSTRACT

The present invention relates to methods for treating patients with chronic cough with nalbuphine compositions as well as treating cough, breathlessness, or dyspnea associated with IPF with nalbuphine compositions, wherein the method provides a therapeutic effect in a patient.

26 Claims, 1 Drawing Sheet

(56) References Cited

U.S. PATENT DOCUMENTS

| | | |
|---|---|---|
| 2008/0207669 A1 | 8/2008 | Perez et al. |
| 2008/0234306 A1 | 9/2008 | Perez et al. |
| 2008/0242720 A1 | 10/2008 | Mangel et al. |
| 2008/0275074 A1 | 11/2008 | Izumimoto et al. |
| 2009/0030026 A1 | 1/2009 | Baichwal et al. |
| 2009/0093509 A1 | 4/2009 | Nazir et al. |
| 2009/0131466 A1 | 5/2009 | Liang et al. |
| 2009/0209569 A1 | 8/2009 | Arnelle et al. |
| 2009/0220583 A1 | 9/2009 | Pereswetoff-Morath et al. |
| 2009/0247635 A1 | 10/2009 | Ehrenpreis |
| 2009/0312359 A1 | 12/2009 | Foss et al. |
| 2010/0150854 A1 | 6/2010 | Schmaus et al. |
| 2010/0227876 A1 | 9/2010 | Rech |
| 2010/0261746 A1 | 10/2010 | Sanghvi et al. |
| 2010/0329984 A1 | 12/2010 | Weers et al. |
| 2011/0067697 A1 | 3/2011 | Lellouche et al. |
| 2011/0190331 A1 | 8/2011 | Avey et al. |
| 2011/0262446 A1 | 10/2011 | Cohen |
| 2012/0040009 A1 | 2/2012 | Hermann |
| 2012/0077803 A1 | 3/2012 | Stuetz et al. |
| 2013/0203797 A1 | 8/2013 | Kobayashi et al. |
| 2014/0171459 A1 | 6/2014 | Sciascia |
| 2014/0179727 A1 | 6/2014 | Sciascia |
| 2014/0350042 A1 | 11/2014 | Sciascia |
| 2015/0197545 A1 | 7/2015 | Schteingart et al. |
| 2015/0359789 A1 | 12/2015 | Sciascia |
| 2016/0346273 A1 | 12/2016 | Sciascia |
| 2017/0000782 A1 | 1/2017 | Sciascia |
| 2017/0216277 A1 | 8/2017 | Sciascia |
| 2017/0326142 A1 | 11/2017 | Ford et al. |
| 2018/0008592 A1 | 1/2018 | Sciascia et al. |
| 2018/0125840 A1 | 5/2018 | Sciascia et al. |
| 2018/0193259 A1 | 7/2018 | Gerhart et al. |
| 2020/0022974 A1 | 1/2020 | Sciascia |
| 2022/0347171 A1 | 11/2022 | Sciascia et al. |
| 2022/0409613 A1 | 12/2022 | Sciascia |

FOREIGN PATENT DOCUMENTS

| | | |
|---|---|---|
| CN | 1835768 A | 9/2006 |
| CN | 104981246 A | 10/2015 |
| CN | 105560202 A | 5/2016 |
| JP | 2001-163784 A | 6/2001 |
| JP | 2008-502603 A | 1/2008 |
| JP | 2008-109898 A | 5/2008 |
| JP | 2009-167198 A | 7/2009 |
| JP | 2016506398 A | 3/2016 |
| JP | 2017517553 A | 6/2017 |
| KR | 10-2015-0093702 A | 8/2015 |
| WO | WO 1984/000889 A1 | 3/1984 |
| WO | WO 98/23290 A1 | 6/1998 |
| WO | WO 2002/087582 A1 | 11/2002 |
| WO | WO-2004008099 A2 | 1/2004 |
| WO | WO 2004/091623 A1 | 10/2004 |
| WO | WO-2004099249 A2 | 11/2004 |
| WO | WO 2005/117871 A2 | 12/2005 |
| WO | WO 2007/025005 A2 | 3/2007 |
| WO | WO 2008/024490 A2 | 2/2008 |
| WO | WO 2008/129000 A1 | 10/2008 |
| WO | WO 2009/047562 A1 | 4/2009 |
| WO | WO 2009/070733 A1 | 6/2009 |
| WO | WO 2009/132313 A2 | 10/2009 |
| WO | WO 2010/107457 A1 | 9/2010 |
| WO | WO 2011/117306 A1 | 9/2011 |
| WO | WO 2012/022919 A2 | 2/2012 |
| WO | WO 2012/052169 A2 | 4/2012 |
| WO | WO 2014/093871 A1 | 6/2014 |
| WO | WO 2015/192071 A1 | 12/2015 |
| WO | WO 2017/108041 A1 | 6/2017 |
| WO | WO 2017/108917 A1 | 6/2017 |
| WO | WO 2017/120468 A1 | 7/2017 |
| WO | WO 2017/165409 A1 | 9/2017 |
| WO | WO 2018/081273 A1 | 5/2018 |
| WO | WO 2020/014342 A1 | 1/2020 |
| WO | WO 2020/023486 A1 | 1/2020 |

OTHER PUBLICATIONS

International Preliminary Reporton Patentability for International Application No. PCT/US2015/035650, dated Dec. 15, 2016, 6 pages.
International Search Report and Written Opinion in International Application No. PCT/US2017/012530, dated Mar. 20, 2017, 19 pages.
International Search Report and Written Opinion in International Application No. PCT/US2017/023398, dated May 25, 2017, 12 pages.
International Search Report and Written Opinion in International Application No. PCT/US2017/058294, dated Dec. 18, 2017, 11 pages.
International Search Report and Written Opinion in International Application No. PCT/US2019/042994, dated Nov. 15, 2019, 24 pages.
European Application No. 13863494.4, Extended European Search Report dated Apr. 12, 2016, 7 pages.
Extended European Search Report for European Application No. 17770981.3, dated Oct. 1, 2019, 10 pages.
Supplementary European Search Report for European Application No. 17863420.0, dated Jun. 8, 2020, 6 pages.
Extended European Search Report for European Application No. 19840931.0, dated Mar. 29, 2022, 9 pages.
"A Study of Nalbuphine (Extended Release) ER in Idiopathic Pulmonary Fibrosis (IPF) for Treatment of Cough (CANAL)," ClinicalTrials.gov, Jul. 23, 2019, retrieved from URL <https://www.clinicaltrials.gov/ct2/show/NCT04030026>, 8 pages.
Bacci et al., "Evaluation of a respiratory symptom diary for clinical studies of idiopathic pulmonary fibrosis," Respiratory Medicine (2018) 134: 130-138.
Bakker, et al., "Bullous pemphigoid as pruritus in the elderly: a common presentation." JAMA Dermatology, Aug. 2013 vol. 149, No. 8, pp. 950-953 (abstract), 2 pages.
Bergasa, N., "An approach to the management of the pruritus of cholestasis," Clin Liver Dis 8 (2004) 55-66.
Bergasa, N., "Medical Palliation of the Jaundiced Patient with Pruritus," Gastroenterol Clin N Am 35 (2006) 113-123.
Bernstein, J. et al., "Butorphanol-induced pruritus antagonized by naloxone," J Am Acad Dermatol, 5[2]:227-228 (1981).
Bigliardi et al., "Peripheral Opiate Receptor System in Human Epidermis and Itch", Itch Basic Mechanism and Therapy, 10:97-106 (2004).
Bruni, E. et al., "Phototherapy of generalized prurigo nodularis", Journal compilation, British Association of Dermatologists, Clinical and Experimental Dermatology, 35, 549-550 (2009).
Butelman et al., "Kappa-Opioid Receptor Binding Populations in Rhesus Monkey Brain: Relationship to an Assay of Thermal Antinociception," J. Pharmacol. Exp. Ther. 285(2):595-601 (1998).
Carstens et al., "Animal Models of Itch: Scratching Away at the Problem", Itch: Basic Mechanisms and Therapy, Yosipovitch et al., Eds., Marcel Dekker Inc, New York, pp. 35-50 (2004).
Cohen et al., "Nalbuphine is better than naloxone for treatment of side effects after epidural morphine," Anesth Analg. 75(5):747-52 (1992).
Davies et al., "A Blinded Study Using Nalbuphine for Prevention of Pruritus Induced by Epidural Fentanyl," Anesthesiology 69(5): 763-765 (1998).
Dawn et al., "Butorphanol for treatment of intractable pruritus," J Am Acad Dermatol 54(3):527-531 (2006).
Dworkin et al., "Phamacologic management of neuropathic pain: Evidence-based recommendations", International Assoc for the Study of Pain, pp. 237-251 (2007).
European Association for the Study of the Liver, "EASL Clinical Practice Guidelines: Management of cholestatic liver diseases," Journal of Hepatology 51 (2009) 237-267.
European Association for the Study of the Liver, "EASL Clinical Practice Guidelines: the diagnosis and management of patients with primary biliary cholangitis," Journal of Hepatology, 2017, vol. 67, pp. 145-172.

(56) References Cited

OTHER PUBLICATIONS

European Medicines Agency (2010) "Public summary of opinion on orphan designation (-)-17-(cyclopropylmethyl)-3,14 β-dihydroxy-4, 5 α-epoxy-6β-[N-methyl-trans-3-(3-furyl) acrylamido] morphinan hydrochloride (intravenous use) for the treatment of uremic pruritus," http://www.ema.europa.eu/docs/en_GB/document_library/Orphan_designation/2009/10/WC500005585.pdf.
European Patent Application No. 15807379.1, Supplementary European Search Report dated Dec. 7, 2017, 10 pages.
Filho, J. W. et al., Prurigo Nodularis of Hyde—an Update—Journal of the European Academy of Dermatology and Venereology, 14(2):75-82 (2000).
Fujii et al., "Essential structure of opioid κ receptor agonist nalfurafine for binding to the κ receptor 3: Synthesis of decahydro(iminoethano)phenanthrene derivatives with an oxygen functionality at the 3-position and their pharmacologies," Bioorg. Med. Chem. Lett., 22:7711-7714 (2012).
Gerak et al., "Antinociceptive and Respiratory Effects of Nalbuphine in Rhesus Monkeys," J. Pharmacol. Exp. Ther., 271(2):993-999 (1994).
Gharagozlou, P. et al., "Activation profiles of opioid ligands in HEK cells expressing delta opioid receptors," BMC Neurosci., 2002, 3:19.
Gharagozlou et al., "Activity of opioid ligands in cells expressing cloned μ opioid receptors," BMC Pharmacol. 3:1, (2003).
Gharagozlou et al., "Pharmacological profiles of opioid ligands at Kappa opioid receptors," BMC Pharmacol. 6:3, (2006).
Gutstein et al., "Chapter 23: Opioid Analgesics" in: Goodman & Gilman's the Pharmacologic Basis of Therapeutics. 10th Ed., Hardman et al., Eds., McGraw Hill, pp. 569-619 (2001).
Hawi, A., et al., "A proof-of-concept study with pharmacokinetics demonstrating anti-pruritic activity of oral nalbuphine in hemodialysis patients with uremic pruritus." Trevi Therapeutics Exhibits Poster at 2014 Annual Meeting of the Society for Investigative Dermatology. Biotech Week, May 28, 2014 (May 28, 2014), p. 1522, XP55429305, Retrieved from the Internet: URL:http://www.trevitherapeutics.com/ckfinder/userfiles/files/SID poster Trevi Therapeutics 567.pdf [retrieved on Nov. 27 2017], 1 page.
Hawi, A., et al., "Pharmacokinetics of nalbuphine hydrochloride extended release tablets in hemodialysis patients with exploratory effect on pruritus." BMC Nephrology (2015); 16: 47.
History of Changes for Study: NCT02143973, ClinicalTrials.gov archive [online], Mar. 18, 2016, [Retrieved on Jan. 20, 2021], Internet, URL, https://www.clinicaltrials.gov/ct2/history/NCT02143973?V_8=View#StudyPageTop.
History of Changes for Study: NCT02143648, ClinicalTrials.gov archive [online], Feb. 22, 2016, [Retrieved on Jan. 20, 2021], Internet, URL, https://www.clinicaltrials.gov/ct2/history/NCT02143648?V_12=View#StudyPageTop.
Iking, et al., "Prurigo as a symptom of atopic and non-atopic diseases: aetiological survey in a consecutive cohort of 108 patients." Journal of the European Academy of Dermatology and Venereology (2013); 27(5): 550-557.
Jung, S., II et al., "Efficacy of Naltrexone in the Treatment of Chronic Refractory Itching in Burn Patients: Preliminary Report of an Open Trial," J. of Burn Care & Research, 30[2]:257-260 (2009).
Kamimura et al., "Long-term efficacy and safety of nalfurafine hydrochloride on pruritus in chronic liver disease patients: Patient-reported outcome based analyses," PLoS ONE (2017) 12(6): e0178991, 11 pages.
Kanavy, H. et al., "Treatmentof Refractory Prurigo Nodularis With Lenalidomide", The Cutting Edge: Challenges in Medical and Surgical Therapies, Archives of Dermatology, 148(7):794-796 (2012).
Keithi-Reddy et al., "Uremic Pruritus," Kidney International, 72:373-377 (2007).
Kendrick et al., "Naloxone versus nalbuphine infusion for prophylaxis of epidural morphine-induced pruritus", Anesth. Analg., 82(3):641-7 (1996).
Kfoury et al., "Uremic pruritus," J. Nephrol,. 25(5):644-652 (2011).
King, Jr., et al., "Idiopathic Pulmonary Fibrosis: Relationship between Histopathologic Features and Mortality," Am. J. Respir. Crit. Care Med., 2001, 164, pp. 1025-1032.
Kjellberg et al., "Pharmacological control of opioid-induced pruritus: a quantitative systematic review of randomized trials", European J. of Anaesthesiology, 18(6): 46-357 (2001).
Kremer et al., "Pathogenesis and Treatment of Pruritus in Cholestasis," Drugs 2008; 68(15): 2163-2182.
Kumada et al., "Efficacy of nalfurafine hydrochloride in patients with chronic liver disease with refractory pruritus: a randomized, doubleblind trial," Hepatology Research 2017; 47: 972-982.
Kumagai et al., "Prospects for a novel kappa-opioid receptor agonist, TRK-820 in uremic pruritus," in: Itch, Basic Mechanisms and Therapy, Yosipovitch et al., Eds., Marcel Dekker Inc, New York, pp. 279-286 (2004).
Kumar et al., "Long-Term Effects of Nalbuphine ER Tablets in Hemodialysis Patients With Uremic Pruritus: a Multicenter Open-Label Trial," American Journal of Kidney Diseases, 2016, vol. 67, No. 5, Abstract 184, p. A64.
Kumar et al., "Nalbuphine ER Tablets in Hemodialysis Patients With Severe Uremic Pruritus: Multicenter, Randomized, Double-Blind, Placebo-Controlled Trial," American Journal of Kidney Diseases, 2016, vol. 67, No. 5, Abtract 185, p. A65.
Lalley, P., "Opioidergic and Dopaminergic Modulation of Respiration," Respir Physiol Neurobiol., 2008, 164(1-2): 160-167.
Lawnhorn et al., "Epidural Morphine With Butorphanol for Postoperative Analgesia After Cesarean Delivery," Anesth. Analg. 72:53-57 (1991).
Lee et al., "Effects of Butorphanol on Morphine-induced Itch and Analgesia in Primates," Anesthesiology 107 (3): 478-485 (2007).
Lee, M. R. et al., "Prurigo nodularis: a review", Australasian J. of Dermatology, 46:211-220 (2005).
Leidy et al., "Measuring respiratory symptoms of COPD: performance of the EXACT—Respiratory Symptoms Tool (E-RS) in three clinical trials," Respiratory Research 2014, 15:124, 10 pages.
Levy, C., "Management of Pruritus in Patients with Cholestatic Liver Disease," Gastroenterology & Hepatology, Sep. 2011, vol. 7, Issue 9, pp. 615-617.
Liao, Chia-Chih, et al. "Efficacy of intramuscular nalbuphine versus diphenhydramine for the prevention of epidural morphine-induced pruritus after cesarean delivery." Chang Gung Med J (2011); 34.2: 172-178.
Lindor et al., "Primary Biliary Cirrhosis," Hepatology, Jul. 2009, vol. 50, No. 1, pp. 291-308.
Mahler and O'Donnell, "Recent Advances in Dyspnea," Chest. 2015;147(1):232-241.
Malgorzata et al., "Understanding Pruritus in Systemic Disease," Journal of Pain and Symptom Management, 21(2):151-168 (2001).
Mazzone et al., "Mapping supramedullary pathways involved in cough using functional brain imaging: Comparison with pain," Pulm Pharmacol Ther., 2009; 22(2): 90-96.
Mela et al., "Review article: pruritus in cholestatic and other liver diseases," Aliment Pharmacol Ther 2003; 17: 857-870.
Metze, D. et al., "Efficacy and safety of naltrexone, an oral opiate receptor antagonist, in the treatment of pruritus in internal and dermatological diseases", J .Am Acad Dermatol, 41 [4]:533-539 (1999).
Montgomery, Clinical Trial: "Nalbuphine for the Treatment of Opioid Induced Pruritus in Children," Dec. 20, 2013, 3 pages, http://clinicaltrials.gov/show/NCT00323154.
Morice et al., "Expert opinion on the cough hypersensitivity syndrome in respiratory medicine," Eur Respir J 2014; 44:1132-1148.
Nagase et al., "Essential structure of opioid κ receptor agonist nalfurafine for binding to the κ receptor 2: Synthesis of decahydro(iminoethano)phenanthrene derivatives and their pharmacologies," Bioorg. Med. Chem. Lett. 22:5071-5074 (2012).
Naini et al., G., "A Promising Drug for the Treatment of Uremic Pruritus", Saudi J. Kidney Dis. Transpl., 18:378-381(2007).
Oeda et al., "Prevalence of pruritus in patients with chronic liver disease: a multicenter study," Hepatology Research 2018; 48: E252-E262.
Pan, "μ-Opposing actions of the κ-opioid receptor," Trends in Pharmacological Sciences 19:94-98 (1998).

(56) References Cited

OTHER PUBLICATIONS

Patel et al., "An update on pruritus associated with CKD," Am J Kidney Dis 50: 11-20 (2007).
Pauli-Magnus et al., "Naltrexone Does Not Relieve Uremic Pruritus: Results of a Randomized, Double-Blind, Placebo-Controlled Crossover Study," J. Am. Soc. Nephrol. 11:514-519 (2000).
Peer et al., "Randomised crossover trial of naltrexone in uraemic pruritus", The Lancet, 348[9041]:1552-1554 (1996).
Peng et al., "Pharmacological Properties of Bivalent Ligands Containing Butorphan Linked to Nalbuphine, Naltrexone and Naloxone at μ, δ and κ Opioid Receptors," J. Med. Chem. 50(9):2254-2258 (2007).
Penning et al., "Reversal of epidural morphine-induced respiratory depression and pruritus with nalbuphine," Canadian Journal of Anesthesia 35(6): 599-604 (1988).
Phan et al., "Antipruritic treatment with systemic μ-opioid receptor antagonists: a review," Journal of the American Academy of Dermatology 63(4): 680-688 (2010).
Phan et al., "Systemic Kappa Opioid Receptor Agonists in the Treatment of Chronic Pruritus: a Literature Review," Acta Dermato-Venereologica 92: 555-560 (2012).
Raghu et al., "Diagnosis of Idiopathic Pulmonary Fibrosis. An Official ATS/ERS/JRS/ALAT Clinical Practice Guideline," Am J Respir Crit Care Med, Sep. 1, 2018, vol. 198, Issue 5, pp. e44-e68.
Reddy et al., "Transdermal Buprenorphine May Be Effective in the Treatment of Pruritus in Primary Biliary Cirrhosis," Journal of Pain and Symptom Management, Nov. 2007, vol. 34, No. 5, pp. 455 and 456.
Rose et al., "Gabapentin: pharmacology and its use in pain management", Anaesthesia, 57(5): 451-462 (2002).
Romagnoli et al., "Ceiling effect for respiratory depression by nalbuphine," Clin. Pharmacol. Ther., vol. 27, No. 4, Apr. 1980, pp. 478-485.
Ryerson et al., "Cough predicts prognosis in idiopathic pulmonary fibrosis," Respirology, (2011) 16:969-975.
Ryerson et al., "Dyspnea in Idiopathic Pulmonary Fibrosis: a Systematic Review," Journal of Pain and Symptom Management, Apr. 2012, 43(4):771-782.
Schmelz, "Itch-mediators and mechanisms", J. of Dermatological Science, 28:91-96, (2002).
Schmidt et al., "Nalbuphine," Drugs and Alcohol Dependence 14:339-362 (1985).
Schwacha, M. G., "Opiates and the Development of Post-Injury Complications: a Review", Int. J. Clin. Exp. Med., 1:42-49 (2008).
Simons, "Advances in $H_1$-Antihistamines." N Engl J Med (2004); 351(21): 2203-2217.
Somrat, C., et al. "Optimal Dose of Nalbuphine for Treatment of Intrathecal-Morphine Induced Pruritus after Caesarean Section." Journal of Obstetrics and Gynaecology Research (1999); 25.3: 209-213.
Spring, P. et al., "Prurigo nodularis: retrospective study of 13 cases managed with methotrexate", Clinical and Experimental Dermatology, 39:468-473 (2014).
Stander, S. et al. "Treatment of Pruritus in Internal and Dermatological Diseases with Opioid Receptor Antagonists", Itch, Basic Mechanisms and Therapy, Michael Dekker, Inc., New York, pp. 259-277 (2004).
Stander, S. et al., "Targeting the Neurokinin Receptor 1 with Aprepitant: a Novel Antipruritic Strategy", PLoS ONE 5(6):1-5 (2010).
Steinhoff, M. et al. "Modern Aspects of Cutaneous Neurogenic Inflammation", Archives of Dermatology (2003); 139.11: 1479-1488.
Tajiri et al., "Recent advances in the management of pruritus in chronic liver diseases," World J Gastroenterol, May 21, 2017; 23(19): 3418-3426.
Trawinska et al., "Patient considerations and drug selection in the treatment of idiopathic pulmonary fibrosis," Therapeutics and Clinical Risk Management 2016:12 563-574.
Trevi Therapeutics Announces Positive Results from Phase 2 Trial in Prurigo Nodularis. Trevi Therapeutics. Oct. 13, 2016. [retrieved on Nov. 22, 2017]. Retrieved from the Internet. <URL: http://www.trevitherapeutics.com/news/view/39>. 3 pages.
Umechi et al., "Involvement of central mu-opioid system in the scratching behavior in mice, and the suppression of it by the activation of kappa-opioid system," Eur. J. Pharmacol. 477(1): 29-35 (2003).
Van Manen et al., "Cough in idiopathic pulmonary fibrosis," Eur Respir Rev 2016; 25:278-286.
Vigeland et al., "Etiology and treatment of cough in idiopathic pulmonary fibrosis," Respiratory Medicine (2017) 123:98-104.
Volkow et al., "Opioid Abuse in Chronic Pain—Misconceptions and Mitigation Strategies," N Engl J Med, 2016, 374(13), 1253-1263.
Wang et al., "Comparison of intravenous nalbuphine infusion versus saline as an adjuvant for epidural morphine," Reg. Anesth. 21(3):214-218 (1996).
Wang et al., "Comparison of Intravenous Nalbuphine Infusion VVersus Naloxone in the Prevention of Epidural Morphine-Related Side Effects," Reg. Anesth. Pain Med. 23(5):479-484 (1998).
Wang et al., "Comparison of Pharmacological Activities of Three Distinct κ Ligands (Salvinorin A, TRK-820 and 3FLB) on κ Opioid Receptors in Vitro and Their Antipruritic and Antinociceptive Activities in Vivo," J. Pharmacol. Exp. Ther. 312(1):220-230 (2005).
Wittels et al., "Opioid Antagonist Adjuncts to Epidural Morphine for Postcesarean Analgesia: Maternal Outcomes," Anesth. Analg 77:925-32 (1993).
Wikström et al., "κ-Opioid System in Uremic Pruritus: Multicenter, Randomized, Double-Blind, Placebo-Controlled Clinical Studies," Journal of the American Society of Nephrology, 2005, vol. 16, No. 12, pp. 3742-3747.
Yeh et al. "Combination of opioid agonist and agonist-antagonist: patient-controlled analgesia requirement and adverse events among different-ratio morphine and nalbuphine admixtures for postoperative pain," British Journal of Anaesthesia 101 (4): 542-548 (2008).
Yokoyama et al. "Treatment of epidural morphine induced pruritus with butorphanol," English Abstract, Masui, 8(2):178-82 (2009).
Yosipovitch, "Chronic Pruritus: a Paraneoplastic Sign," Dermatol. Ther. 23(6): 590-596 (2010).
Yosipovitch, G. et al., "Chronic Pruritus", N. Eng. J. Med., 368[17]:1625-1634 (2013).
Zylicz et al., "Severe Pruritus of Cholestasis in Disseminated Cancer: Developing a Rational Treatment Strategy. A Case Report," Journal of Pain and Symptom Management, Jan. 2005, vol. 29 No. 1, pp. 100-103.
Clinical Trial: Open Label Extension Study of Nalbuphine HCI ER in Patients With Prurigo Nodularis, v8 [retrieved from internet on Apr. 5, 2022], Retrieved from https://www.clinicaltrials.gov/ct2/history/NCT02174432?V_8=View#StudyPageTop.
Clinical Trial: Study of Nalbuphine HCI ER Tablets in Patients With Prurigo Nodularis, v13 [retrieved from internet on Apr. 5, 2022]. Retrieved from https://www.clinicaltrials.gov/ct2/history/NCT02174419?V_13=View#StudyPageTop.
Pallasch et al., "Butorphanol and nalbuphine: a pharmacologic comparison," Oral Surgery, Oral Medicine, Oral Pathology, Jan. 1985, 59(1):15-20.
Prous Science Integrity, "Nalbuphine hydrochloride," Prous Science, 2009, Entry No. 91357, CAS Registry No. 23277-43-2, 1 pages.
2016 Nubain® label at p. 5 (WARNINGS, Life-Threatening Respiratory Depression in Patients with Chronic Pulmonary Disease or in Elderly, Cachectic, or Debilitated Patients), 17 pages.
Collard, H. R. et al., "Acute exacerbation of idiopathic pulmonary fibrosis. An international working group report", American Journal of Respiratory and Critical Care Medicine. (Aug. 1, 2016); 194(3): 265-275.
COMBIVENT® RESPIMAT® (ipratropium bromide and albuterol inhalation spray), for oral inhalation use brochure Initial U.S. Approval: 1996, 17 pages.
COPD and Asthma: Differential Diagnosis, American Academy of Family Physicians (2016); 12 pages.
Coughing: Controlled Coughing, Cleveland Clinic (Sep. 1, 20184) 9 pages.

(56) References Cited

OTHER PUBLICATIONS

Delcò F. et al., "Dose Adjustment in Patients with Liver Disease," Drug Safety. (2005); 28(6): 529-545.
Franklin M.C., et al. "Insights into ErbB signaling from the structure of the ErbB2-pertuzumab complex." Cancer Cell (2004); 5(4): 317-328.
Gelot S. et al., "Opioid Dosing in Renal and Hepatic Impairment," Nephrology. (Aug. 20, 2014); 39(8): 34-38.
Horton M.R. et al., "Thalidomide for the treatment of cough in idiopathic pulmonary fibrosis: a randomized trial", Annals of Internal Medicine. (Sep. 18, 2012); 157(6): 398-406.
Kotb et al., "Pharmacokinetics of controlled release morphine (MST) in patients with liver cirrhosis," British Journal of Anaesthesia. (1997); 79: 804-806.
Liu H. et al., "Effects of first and second generation antihistamines on muscarinic induced mucus gland cell ion transport" BMC Pharmacology. (Dec. 2005); 5(1): 1-10. Epub date Mar. 24, 2005.
Martinez F.J. et al., "Phase 2B study of inhaled RVT-1601 for chronic cough in idiopathic pulmonary fibrosis: a multicenter, randomized, placebo-controlled study (SCENIC trial)", American Journal of Respiratory and Critical Care Medicine. (May 1, 2022); 205(9): 1084-1092.
Martinez, F.J. et al., "Treatment of persistent cough in subjects with idiopathic pulmonary fibrosis (IPF) with gefapixant, a P2X3 antagonist, in a randomized, placebo-controlled clinical trial", Pulmonary therapy. (Dec. 2021); 7(2): 471-486 Epub date Jun. 21, 2021.
McGarvey L.P., et al., "Efficacy and safety of gefapixant, a P2X3 receptor antagonist, in refractory chronic cough and unexplained chronic cough (COUGH-1 and COUGH-2): results from two double-blind, randomised, parallel-group, placebo-controlled, phase 3 trials", The Lancet. (Mar. 5, 2022); 399(10328): 909-923.
Meltzer E.B., et al., "Idiopathic pulmonary fibrosis", Orphanet Journal of Rare Diseases. (Mar. 26, 2008); 3(1): 1-5.
Montuschi, P. "Pharmacological treatment of chronic obstructive pulmonary disease", International Journal of Chronic Obstructive Pulmonary Disease. (Dec. 2006); 1(4): 409-424.
Morice A.H., et al., "Opiate therapy in chronic cough", American Journal of Respiratory and Critical Care Medicin. (Feb. 15, 2007); 175(4): 312-315.
Moroni M., et al. "Inhaled sodium cromoglycate to treat cough in advanced lung cancer patients," British Journal of Cancer. (Jul. 1, 1996); 74(2): 309-311.
Patel M. "A review of standard pharmacological therapy for adult asthma-Steps 1 to 5", Chronic Respiratory Disease. (May 2015); 12(2): 165-176.
Plantier L. et al., "Physiology of the lung in idiopathic pulmonary fibrosis" European Respiratory Review. (Mar. 31, 2018); 27(147): 1-14.
Ramirez, J.M. et al., "Neuronal mechanisms underlying opioid-induced respiratory depression: our current understanding", Journal of Neurophysiology. (May 1, 2021); 125(5): 1899-18919. Epub Apr. 7, 2021.
"The Voice of the Patient: a series of reports from the U.S. Food and Drug Administration's (FDA's) Patient-Focused Drug Development Initiative, Idiopathic Pulmonary Fibrosis", Center for Drug Evaluation and Research (CDER) U.S. Food and Drug Administration (FDA) Public Meeting (Sep. 26, 2014) Report Date:(Mar. 2015) 22 pages.
Troy L.K., et al., "Sleep disordered breathing in interstitial lung disease: a review". World Journal of Clinical Cases: WJCC. (Dec. 12, 2014); 2(12): 828-834.
Vajdos F.F., et al., "Comprehensive Functional Maps of the Antigen-Binding Site of an Anti-ErbB2 Antibody Obtained with Shotgun Scanning Mutagenesis," J. Mol. Biol. (Jul. 2002); 320(2): 415-428.
Valle et al., "A phase Ib study of pertuzumab (P), a recombinant humanized anitbody to HER2, and capecitabine (C) in patient with advanced solid tumors" European Journal of Cancer Supplements. (Sep. 30, 2004); 2(8): 1 page.
Van Manen M.J. et al., "Optimizing quality of life in patients with idiopathic pulmonary fibrosis", Therapeutic Advances in Respiratory Disease. (Mar. 2017); 11(3): 157-169.

* cited by examiner

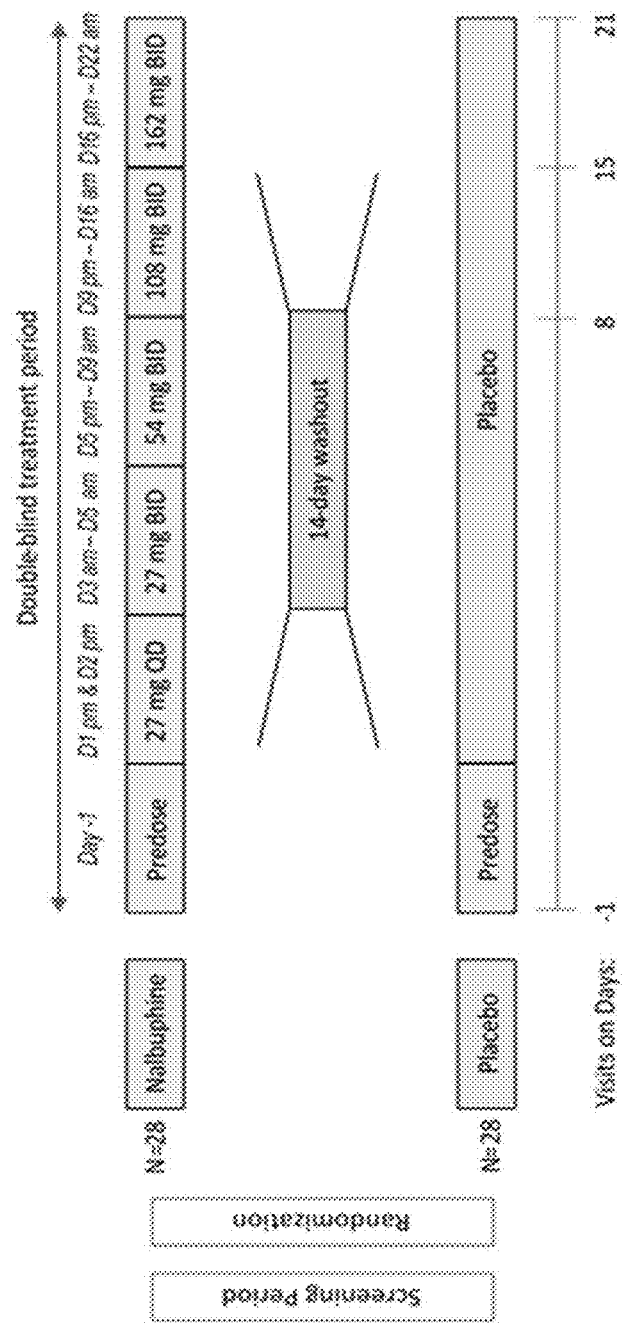

TREATMENT OF CHRONIC COUGH, BREATHLESSNESS AND DYSPNEA

CROSS-REFERENCE TO RELATED APPLICATIONS

The application is a continuation of U.S. application Ser. No. 17/576,208, filed Jan. 14, 2022, which is a continuation of U.S. application Ser. No. 17/341,936, filed Jun. 8, 2021, which is a continuation of U.S. application Ser. No. 17/085,098, filed Oct. 30, 2020, which is a continuation of U.S. application Ser. No. 16/810,317, filed Mar. 5, 2020, which is a continuation of U.S. application Ser. No. 16/519,831, filed Jul. 23, 2019, which claims the benefit of priority to U.S. Provisional Application Ser. No. 62/701,902, filed Jul. 23, 2018, the contents of which are hereby incorporated by reference in their entirety.

FIELD OF THE INVENTION

In various embodiments the present invention relates to methods and compositions for treating chronic cough, breathlessness or dyspnea in patients using nalbuphine.

BACKGROUND

Cough is the most common symptom for which individuals seek medical advice. Cough is a three phase expulsive motor act characterized by inspiration effort (inspiratory phase), followed by a forced expiratory effort against a closed glottis (compressive phase) and then by opening of the glottis and rapid expiratory airflow (expulsive phase). There are two general types of cough: acute cough and chronic cough. Chronic cough is a cough that lasts for at least 8 weeks and may be of an explained (e.g., postnasal drip, asthma, gastroesophageal reflux disease (GERD), chronic bronchitis) or unexplained origin. Chronic cough severely impacts a patient's quality of life with patients often avoiding social interactions for fear of cough-induced emesis, incontinence or syncope.

Breathlessness is the subjective experience of breathing discomfort that consists of qualitatively distinct sensations of shortness of breath that vary in intensity. Dyspnea is breathlessness that is experienced with activity, exercise or exertion. At a basic physiological level, breathlessness or dyspnea results from the imbalance between the central neural drive demand directing the breathing function and the capacity of the respiratory system to achieve that demand. Major sensory perceptions experienced by the breathless or dyspneic patient include feelings of unsatisfied air hunger following inspiration and the feeling of a large work effort to breathe. The presence of "acute exacerbation of IPF" consists of worsening of both dyspnea and lung function and is a potent predictor of patient mortality in IPF patients.

Chronic cough, breathlessness and dyspnea are common symptoms of idiopathic pulmonary fibrosis. However, chronic cough, breathlessness and dyspnea, especially associated with IPF, are often refractory to treatment with common antitussive, anti-breathlessness and anti-dyspneic agents, and there is a need for effective treatments of chronic cough, breathlessness and dyspnea.

SUMMARY OF THE INVENTION

The present disclosure, among other things, provides methods of treating cough, breathlessness or dyspnea comprising administering an effective amount of nalbuphine or a pharmaceutically acceptable salt, solvate or ester thereof to a patient in need of such treatment.

In some embodiments, the present disclosure provides methods of treating chronic cough comprising administering an effective amount of nalbuphine or a pharmaceutically acceptable salt, solvate or ester thereof to a patient in need of such treatment. In some embodiments, the patient in need of a treatment of chronic cough is a patient with unexplained chronic cough, refractory chronic cough or cough hypersensitivity syndrome. In some embodiments, the patient's chronic cough is refractory to treatment with tramadol.

In some embodiments, the patient in need of a treatment of chronic cough is a patient without a lung disease. In some embodiments, the patient in need of a treatment of chronic cough is a patient with a lung disease. In some embodiments, the lung disease is an interstitial lung disease. In some embodiments, the lung disease is a chronic obstructive pulmonary lung disease (COPD).

In some embodiments, the patient in need of a treatment of cough, breathlessness or dyspnea is a patient with cough, breathlessness or dyspnea associated with idiopathic pulmonary fibrosis ("IPF cough, breathlessness or dyspnea"). In some embodiments, the patient has chronic cough associated with IPF.

In some embodiments, the patient in need of a treatment of IPF cough, breathlessness, or dyspnea is a patient with IPF cough, breathlessness, or dyspnea that is refractory to other therapies. In some embodiments, the patient's IPF cough is refractory to treatment with other antitussive agents. In some embodiments, the patient's IPF cough, breathlessness, or dyspnea is refractory to treatment with μ-opioid agonists. In some embodiments, the patient's IPF cough is refractory to treatment with pirfenidone. In some embodiments, the patient's IPF cough is refractory to treatment with thalidomide. In some embodiments, the patient's IPF cough is refractory to treatment with cromolyn sodium.

In some embodiments, the patient in need of a treatment of cough, breathlessness or dyspnea is a patient also treated for a disease selected from pulmonary hypertension, obstructive sleep apnea, lung cancer, COPD/emphysema, ischemic heart disease and GERD.

According to some embodiments of the present disclosure, the method of treating cough, breathlessness, or dyspnea comprises administering for at least a week to a patient in need thereof a daily dose of at least about 15 mg nalbuphine or a pharmaceutically acceptable salt, solvate or ester thereof. In some embodiments, the method of treating cough, breathlessness, or dyspnea comprises administering for at least a week to a patient in need thereof a daily dose of at least about 120 mg nalbuphine or a pharmaceutically acceptable salt, solvate or ester thereof. In some embodiments, the method of treating cough, breathlessness, or dyspnea comprises administering for at least a week to a patient in need thereof a daily dose of at least about 180 mg of nalbuphine or a pharmaceutically acceptable salt, solvate or ester thereof. In some embodiments, the method of treating cough, breathlessness, or dyspnea comprises administering for at least a week to a patient in need thereof a daily dose of at least about 360 mg of nalbuphine or a pharmaceutically acceptable salt, solvate or ester thereof. In some embodiments, about 10 mg of the nalbuphine is administered twice a day. In some embodiments, about 15 mg of the nalbuphine is administered twice a day. In some embodiments, about 20 mg of the nalbuphine is administered twice a day. In some embodiments, about 30 mg of the nalbuphine is administered twice a day. In some embodiments, about 60 mg of the nalbuphine is administered twice a day. In some embodiments, about 90 mg of the nalbuphine is administered twice a day. In some embodiments, about 180 mg of the nalbuphine is administered once a day. In some embodiments, about 180 mg of the nalbuphine is administered twice a day. In some embodiments, about 360 mg of the nalbuphine is administered once a day.

In some embodiments, the nalbuphine or a pharmaceutically acceptable salt, solvate or ester thereof is administered for about 2 weeks. In some embodiments, the nalbuphine or a pharmaceutically acceptable salt, solvate or ester thereof is administered for about 4 weeks. In some embodiments, the nalbuphine or a pharmaceutically acceptable salt, solvate or ester thereof is administered for about 8 weeks. In some embodiments, the nalbuphine or a pharmaceutically acceptable salt, solvate or ester thereof is administered for about 10 weeks. In some embodiments, the nalbuphine or a pharmaceutically acceptable salt, solvate or ester thereof is administered for about 12 weeks. In some embodiments, the nalbuphine or a pharmaceutically acceptable salt, solvate or ester thereof is administered for about 18 weeks. In some embodiments, the nalbuphine or a pharmaceutically acceptable salt, solvate or ester thereof is administered for about 50 weeks.

In some embodiments, after the treatment the patient experiences a substantial reduction in cough compared to prior to the treatment. In some embodiments, after the treatment the patient experiences a substantial reduction in breathlessness compared to prior to the treatment. In some embodiments, after the treatment the patient experiences a substantial reduction in dyspnea compared to prior to the treatment.

In some embodiments, the method of treating cough, breathlessness, or dyspnea further includes a step of titrating the dose of the nalbuphine or a pharmaceutically acceptable salt, solvate or ester thereof for at least about one week until a steady state is achieved in the patient. In some embodiments, the titration is conducted for about 2 weeks until a steady state is achieved in the patient. In some embodiments, the titration is conducted for about 7 days to about 30 days until a steady state is achieved in the patient. In some embodiments, the titration is conducted for about 12 days to about 20 days until a steady state is achieved in the patient.

In some embodiments, ascending doses of the nalbuphine or a pharmaceutically acceptable salt, solvate or ester thereof are administered during the titration until a steady state is achieved in the patient. In some embodiments, ascending doses of the nalbuphine or a pharmaceutically acceptable salt, solvate or ester thereof are administered during the titration until an effective amount 60 mg, 90 mg, 120 mg, 180 mg, 240 mg or 360 mg is achieved in the patient is achieved in the patient.

In some embodiments, the titration is initiated with a dose of about 15 mg once or twice a day. In some embodiments, the titration is initiated with a dose of about 30 mg once or twice a day. In some embodiments, the titration comprises administering the nalbuphine in increments ranging from about 15 mg to about 30 mg. In some embodiments, the titration comprises administering the nalbuphine in increments ranging from about 15 mg to about 60 mg. In some embodiments, titration twice a day is with an AM dosage and a PM dosage, wherein the PM dosage is higher than or the same as the AM dosage.

In accordance with some embodiments of the present disclosure, the rate of adverse events after the treatment with the nalbuphine or a pharmaceutically acceptable salt, solvate or ester thereof is substantially the same as the rate of adverse events after administering a placebo for the same period of time.

According to some embodiments of the present disclosure, clinical studies show that patients treated with nalbuphine or a pharmaceutically acceptable salt, solvate or ester thereof experience a statistically significant reduction of cough, breathlessness, or dyspnea compared to patients treated with a placebo. In some embodiments, the statistically significant reduction of cough, breathlessness, or dyspnea is indicated by a p value of less than or equal to about 0.05.

According to some embodiments of the present disclosure, after the treatment the patient experiences a substantial reduction of fatigue compared to prior to the treatment.

According to some embodiments of the present disclosure, after the treatment the patient experiences a substantial reduction in the rate of pulmonary fibrosis progression compared to prior to said treating as quantified by objective measures (chest x-ray, pulmonary function tests, etc.).

In some embodiments, after said treatment the patient experiences a substantial reduction in the hospitalization rate based on improvement in the breathlessness, dyspnea, or cough status.

In some embodiments, after said treatment the patient experiences a substantial reduction in morbidity and mortality as a result of the lessening incidence of acute exacerbations of IPF (AE-IPF) related to deterioration of lung function and/or lessening of breathing difficulties secondary to an interruption in the "dyspnea cycle" positive feedback loop of progressively more frequent episodes of dyspnea of increasing intensity.

In accordance with some embodiments of the present disclosure, the method of treating cough, breathlessness, or dyspnea does not produce a substantial aquaretic effect.

In some embodiments, the method of treating cough, breathlessness, or dyspnea further includes administering at least one additional antitussive, anti-breathlessness and anti-dyspneic drug. In some embodiments, the method of treating cough, breathlessness, or dyspnea further includes administering at least one additional antitussive, anti-breathlessness or anti-dyspneic drug.

In some embodiments, the nalbuphine is in the form of an extended release oral dosage form.

In some embodiments, the nalbuphine is administered in a formulation comprising nalbuphine hydrochloride, mannitol, hydroxypropyl cellulose, locust bean gum, xanthan gum, calcium sulfate dihydrate, and magnesium stearate.

The present methods, and advantages thereof, are further illustrated by the following non-limiting detailed description, including the Examples.

BRIEF DESCRIPTION OF THE FIGURES

FIG. 1 is a schematic overview of the screening and treatment regimens of two randomized groups of patients. QD=once a day; BID=twice a day; PBO=placebo. Nalbuphine doses expressed as Equivalent Amount of Nalbuphine Free Base.

Definitions

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

Throughout this disclosure, various patents, patent applications and publications (including non-patent publications) are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "administer," "administering" or "administration" as used herein refer to either directly administering a compound or pharmaceutically acceptable salt or ester of the compound or a composition comprising the compound or pharmaceutically acceptable salt or ester of the compound to a patient.

The term "adverse event" (AE) as used herein is defined as any untoward medical occurrence in a clinical investigation patient reported on or after the first screening date. An AE does not necessarily have to have a causal relationship with the treatment. An AE can therefore be any unfavorable and unintended sign (including an abnormal laboratory finding), symptom whether or not related to the medicinal (investigational) product, or disease temporally associated with the use of a medicinal (investigational) product. Typical adverse events include nausea, vomiting, somnolence, dizziness and hallucination. In accordance with the present disclosure, the rate of adverse events after the treatment is substantially the same as the rate of adverse events after administering a placebo for the same period of time.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "chronic cough" is used in this disclosure to mean cough that lasts for at least 8 weeks.

The term "cough hypersensitivity syndrome" is used in this disclosure to mean a clinical syndrome characterized by troublesome coughing often triggered by low levels of thermal, mechanical or chemical exposure. This syndrome is manifested clinically by coughing induced by seemingly innocuous stimuli such as changes in ambient temperature, laughing, talking on the phone or aerosol exposure.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound, or a salt, solvate or ester thereof, that, when administered to a patient, is capable of performing the intended result. For example, an effective amount of nalbuphine is that amount that is required to reduce at least one symptom of IPF in a patient, e.g. the amount required to reduce the cough frequency or breathlessness in a patient. The actual amount that comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "treating" as used herein with regard to a patient, refers to improving at least one symptom of the patient's disorder. Treating can be curing, improving, or at least partially ameliorating a disorder.

The term "therapeutic effect" as used herein refers to a desired or beneficial effect provided by the method and/or the composition. For example, the method for treating IPF provides a therapeutic effect when the method reduces at least one symptom of IPF, e.g., cough frequency or breathlessness, in a patient.

DETAILED DESCRIPTION

Idiopathic Pulmonary Fibrosis (IPF) is a specific form of chronic, progressive fibrosing interstitial pneumonia of unknown cause, occurring primarily in older adults, limited to the lungs and associated with histopathological and/or radiologic pattern of usual interstitial pneumonia (UIP) (Raghu G, et al; American Thoracic Society, European Respiratory Society, Japanese Respiratory Society, and Latin American Thoracic Society. Diagnosis of Idiopathic Pulmonary Fibrosis. An Official ATS/ERS/JRS/ALAT Clinical Practice Guideline. Am J Respir Crit Care Med. 2018 Sep. 1; 198(5).). Most IPF patients experience a slow progression over time with some patients remaining relatively stable; however, others have rapidly progressing disease. Common comorbidities in IPF patients include pulmonary hypertension, obstructive sleep apnea, lung cancer, COPD/emphysema, ischemic heart disease and GERD. Cough and dyspnea are common symptoms of IPF patients with 81% and 90%, respectively, of patients reporting these symptoms at the time of diagnosis.

The cough associated with IPF ("IPF cough") is a persistent dry cough that is worse with exercise and talking (C. Vigeland, et al., Etiology and treatment of cough in idiopathic pulmonary fibrosis, Respiratory Medicine, 2017, 123, 98-104.). The cough frequency has been reported at between 1.9-39.4 coughs per hour with a daytime cough median frequency of 14.6 per hour. The impact of the chronic cough on the IPF patient's quality of life is significant and debilitating. The cough causes difficulty falling asleep, patients avoid social interactions and patients fear cough-induced emesis, incontinence or syncope. Furthermore, recent studies suggest that cough is an independent predictor of disease progression and death in IPF patients (C. Ryerson, et al., Cough predicts prognosis in idiopathic pulmonary fibrosis. Respirology. 2011; 16: 969-75.).

The etiology of IPF cough is uncertain (below); however, the net effect is that IPF patients develop a hypersensitivity of the cough reflex. Without being bound by any theory, the etiology of IPF cough is presumed related to disease-generated chemical mediators (for example, inflammatory cytokines, histamine, etc.) that alter the excitability of the C and A-delta nerve fibers of the afferent arm of the cough reflex as well as from architectural distortion of lung tissue secondary to fibrosis resulting in increased nerve signaling from mechanoreceptors to the cough reflex center in the brainstem that induce cough.

Dyspnea in IPF patients is strongly correlated to decreased quality of life (for example, deconditioning and depression correlate with dyspnea) (C. Ryerson, et al., Dyspnea in Idiopathic Pulmonary Fibrosis: A Systematic Review, J. Pain and Symptom Management 2012, 43 (4); 771-82). Mortality is also correlated to the degree of dyspnea such that a one-unit increase in the dyspnea score is associated with a 10% increase in the risk of death and a two-unit change resulted in a 49% increase of death (using the [0-20 dyspnea scale described in L. Watters et al., A Clinical, Radiographic, and Physiologic Scoring System for the Longitudinal Assessment of Patients with Idiopathic Pulmonary Fibrosis, Am. Rev. Respir. Dis. 1986; 133: 97-103.]) (T. King, et al., Idiopathic Pulmonary Fibrosis: Relationship between Histopathologic Features and Mortality, Am. J. Respir. Crit. Care Med. 2001, 164, pp 1025-1032.).

Mu and kappa opioid receptors are present in areas of the central and peripheral nervous system that are associated with respiratory function and the cough reflex. For example, mu opioid receptors are present in high density in the anterior cingulate cortex, insula, amygdala, brainstem, spinal cord and peripheral endings of Type C and A-delta fibers (N. Volkow, et al., Opioid Abuse in Chronic Pain—Misconceptions and Mitigation Strategies, N Engl J Med, 2016, 374 (13), 1253-63.), which are involved in pulmonary ventilation mechanics, respiratory reflexes and the perceptions surrounding the function of respiration. Kappa opiate receptors are present in the anterior cingulate cortex, insula and amygdala. Mu, kappa and delta opioid receptors are found in the respiratory related regions of the brainstem and spinal cord. Endogenous opioids are found in the medullary and pontine respiratory regions and are believed to play an important, but yet undefined, role in modulating respiration (P. Lalley, Opioidergic And Dopaminergic Modulation of Respiration, Respir Physiol Neurobiol. 2008, 164 (1-2): 160-167.).

Chronic coughing, dyspnea and breathlessness are impacted by cortical neurophysiology. Functional brain imagining study in healthy volunteers administered the cough irritant capsacin showed activation of anterior insula, and discrete regions of the anterior cingulate cortex (Mazzone S B, et al., Mapping supramedullary pathways involved in cough using functional brain imaging: comparison with pain. Pulm Pharmacol Ther. 2009; 22(2):90-6.).

Mahler and O'Donnell (Mahler D A, O'Donnell D E. Recent advances in dyspnea. Chest. 2015; 147(1):232-41.) explain that cortical-limbic system (anterior cingulate gyms, insula, amygdala) activate the emotional aspect of respiratory distress and the unpleasant perception of breathlessness and/or dyspnea. Neuroimaging studies indicate a cortical-limbic network involving insular cortex and anterior cingulate cortex is involved in the perception of dyspnea (Mahler and O'Donnell 2015). Without being bound by any theory, pharmacological intervention at the cortical level (for example, by administration of the opioid receptor active compound nalbuphine) improves chronic cough, breathlessness and dyspnea because opioid receptors exist in high density in the anterior cingulate cortex, insula and amygdala (Volkow N D, McLellan A T. Opioid Abuse in Chronic Pain—Misconceptions and Mitigation Strategies. N Engl J Med. 2016; 374(13):1253-63.).

Additionally, the brainstem has a high density of opioid receptors (Volkow et al. 2016). The brainstem is central to the regulation of breathing and the activation and setting the sensitization level of the cough reflex. Without being bound by any theory, because neural communication circuits exist between the cortex and brainstem, pharmacological action of nalbuphine directly at the brainstem level as well as via nalbuphine mediated cortical influences on the brainstem alters neurophysiological brainstem activity and thus improve the symptoms of chronic coughing, dyspnea and breathlessness.

In one aspect, the present disclosure provides a method of treating cough, breathlessness, or dyspnea comprising administering an effective amount of nalbuphine or a pharmaceutically acceptable salt, solvate or ester thereof. In accordance with some embodiments of the present disclosure, at least about 30 mg, 60 mg, 90 mg, 120 mg, or 180 mg of the nalbuphine or a pharmaceutically acceptable salt, solvate or ester thereof is administered.

In some embodiments, methods of the present disclosure are used for the treatment of chronic cough. In some embodiments, the chronic cough is selected from refractory chronic cough, unexplained chronic cough, unexplained and refractory chronic cough, idiopathic chronic cough, cough hypersensitivity syndrome, hypertussia, allotussia and neurogenic cough as well as suppression of the sensation of the urge to cough.

In some embodiments, the patient in need of a treatment of chronic cough is a patient without a lung disease.

In some embodiments, the patient in need of a treatment of chronic cough is a patient with a lung disease. In some embodiments, the lung disease is an interstitial lung disease. In some embodiments, the interstitial lung disease is selected from the group consisting of idiopathic pulmonary fibrosis, hypersensitivity pneumonitis, sarcoidosis, asbestosis, bronchiolitis obliterans, histiocytosis X, chronic eosinophilic pneumonia, collagen vascular disease, granulomatous vasculitis, Goodpasture's syndrome and, pulmonary alveolar proteinosis. In some embodiments, the interstitial lung disease is selected from the group consisting of idiopathic pulmonary fibrosis, hypersensitivity pneumonitis, sarcoidosis, and asbestosis. In some embodiments, the lung disease is a chronic obstructive pulmonary lung disease (COPD). In some embodiments, the COPD is associated with a condition selected from the group consisting of emphysema, chronic bronchitis and Alpha-1-antitrypsin (AAt) deficiency. In some embodiments, the COPD is associated with an irritant selected from the group consisting of cigarette smoke, secondhand smoke, pipe smoke, air pollution and workplace exposure to dust, smoke or fumes.

In some embodiments, the chronic cough is refractory to treatment with tramadol. In some embodiments, the chronic cough is refractory to treatment with morphine. In some embodiments, the chronic cough is refractory to treatment with codeine.

In some embodiments, methods of the present disclosure are used for the treatment of cough, breathlessness, or dyspnea associated with IPF. In some embodiments, methods of the present disclosure are used for the treatment of IPF cough, breathlessness, or dyspnea wherein prior to said treatment the patient's cough severity is at least 40 mm on the visual analogue scale (VAS) cough scale. In some embodiments, methods of the present disclosure are used for the treatment of IPF cough, breathlessness, or dyspnea wherein prior to said treatment the patient's daytime average cough count is at least 15 per hour measured using a cough count device.

In some embodiments, nalbuphine is used or indicated for the treatment of cough, breathlessness, or dyspnea in patients with chronic cough associated with IPF. In some embodiments, nalbuphine is used or indicated for the treatment of cough, breathlessness, or dyspnea in patients with refractory chronic cough associated with IPF.

In some embodiments, nalbuphine is used or indicated for the treatment of IPF cough, breathlessness, or dyspnea in patients who are also treated for a disease selected from the group consisting of pulmonary hypertension, obstructive sleep apnea, lung cancer, COPD/emphysema, ischemic heart disease and GERD.

According to the present disclosure, the nalbuphine is administered on a once or twice a day basis to provide effective relief of the symptoms of cough, breathlessness, or dyspnea that is not effectively relieved by other therapies (i.e., the cough, breathlessness, or dyspnea is refractory to other treatments).

In some embodiments, the methods of the present disclosure are used to treat IPF cough where the cough is refractory to treatment with other antitussive agents. In some embodiments, the antitussive agent is selected from lidocaine, gefapixant, serlopitant, and orvepitant.

In some embodiments, the methods of the present disclosure are used to treat IPF cough, breathlessness, or dyspnea where the cough, breathlessness, or dyspnea is refractory to treatment with μ-opioid agonists. In some embodiments, the μ-opioid agonist is selected from morphine, tramadol, dihydrocodeine and diamorphine.

In some embodiments, the methods of the present disclosure are used to treat IPF cough where the cough is refractory to treatment with pirfenidone. In some embodiments, the methods of the present disclosure are used to treat IPF cough, breathlessness, or dyspnea where the cough, breathlessness, or dyspnea is refractory to treatment with nintedanib. In some embodiments, the methods of the present disclosure are used to treat IPF cough where the cough is refractory to treatment with thalidomide. In some embodiments, the methods of the present disclosure are used to treat IPF cough where the cough is refractory to treatment with cromolyn sodium.

In accordance with some embodiments of the present disclosure, the method provides a therapeutic effect without producing a substantial adverse event. In some embodiments, the rate of adverse events after the treatment with nalbuphine is substantially the same as the rate of adverse events after administering a placebo for the same period of time.

In accordance with some embodiments of the present disclosure, the method of treating cough, breathlessness, or dyspnea does not produce a substantial aquaretic effect.

In one aspect, the present disclosure provide a method of treating cough associated with a condition selected from asthma, gastroesophageal reflux disease (GERD)/esophageal irritation from other causes, and upper airway disease In one aspect, the present disclosure provides a method of treating chronic cough comprising administering an effective amount of a kappa agonist to a patient in need thereof. In some embodiments, the kappa agonist is difelikefalin or a pharmaceutically acceptable salt, solvate or ester thereof. In some embodiments, the kappa agonist is Nalfurafine or a pharmaceutically acceptable salt, solvate or ester thereof.

In one aspect, the present disclosure provides a method of treating IPF cough, breathlessness or dyspnea comprising administering an effective amount of a kappa agonist to a patient in need thereof. In some embodiments, the kappa agonist is difelikefalin or a pharmaceutically acceptable salt, solvate or ester thereof. In some embodiments, the kappa agonist is Nalfurafine or a pharmaceutically acceptable salt, solvate or ester thereof.

In some embodiments, the total daily dose of the difelikefalin is about 0.25 mg a day to about 5 mg a day, including about 0.25 mg a day, about 0.5 mg a day, about 1.0 mg a day, 1.5 mg a day, about 2.0 mg a day, about 2.5 mg a day, about 3.0 mg a day, about 3.5 mg a day, about 4.0 mg a day, about 4.5 mg a day, and about 5.0 mg a day (including all range in between) for the treatment of chronic cough, IPF cough, breathlessness or dyspnea.

In some embodiments, the total daily dose of the nalfurafine is about 1.5 μg a day to about 6.0 μg a day, including about 1.5 μg a day, about 2.0 μg a day, about 2.5 μg a day, about 3.0 μg a day, about 3.5 μg a day, about 4.0 μg a day, about 4.5 μg a day, about 5.0 μg a day, about 5.5 μg a day and about 6.0 μg a day (including all range in between) for the treatment of chronic cough, IPF cough, breathlessness or dyspnea.

Nalbuphine

Nalbuphine as employed in the present methods can form a part of a pharmaceutical composition by combining nalbuphine, or a pharmaceutically acceptable salt, solvate or ester thereof, with a pharmaceutically acceptable carrier. Additionally, the compositions can include an additive selected from the group consisting of adjuvants, excipients, diluents, release-modifying agents and stabilizers. The composition can be an immediate release formulation, a delayed release formulation, a sustained release formulation or an extended release formulation.

Nalbuphine HCl (17-(cyclobutylmethyl)-4,5α-epoxymorphinian-3, 6α, 14-triol, hydrochloride) is a synthetic opioid. Structurally, nalbuphine is a derivative of 14 hydroxymorphine.

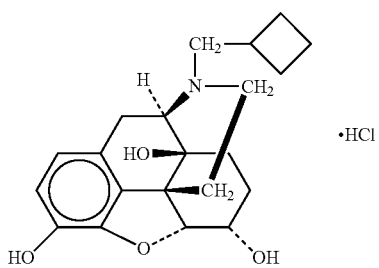

Nalbuphine HCl is currently available only as a generic medication in an injectable form. An injectable form of nalbuphine has been available as an approved drug formulation since 1978. Nubain® was the innovator brand injectable form of nalbuphine on which the presently sold generic bioequivalent injectable formulations are based. The injectable formulation is currently approved for use in the relief of moderate to severe pain, a supplement to balanced anesthesia, for pre-operative and post-operative analgesia and obstetrical analgesia during labor and delivery.

The present disclosure also includes pharmaceutically acceptable esters of nalbuphine. The term "ester" denotes a derivative of the agent containing an ester functional group (as described herein), which is capable of releasing the agent when the ester form is administered to a patient. Release of the active ingredient occurs in vivo. Pharmaceutically acceptable esters can be prepared by techniques known to one skilled in the art. These techniques generally modify appropriate functional groups in a given compound. These modified functional groups however regenerate original functional groups by metabolism of the compound in vivo. Esters include compounds wherein a hydroxy, carboxylic, or a similar group is modified.

Suitable pharmaceutically acceptable esters for a hydroxyl group include inorganic esters such as phosphate esters and α-acyloxyalkyl ethers and related compounds which, as a result of in vivo hydrolysis of the ester, provide the parent hydroxy group. In vivo hydrolyzable ester forming groups for hydroxy include alkanoyl (e.g., $C_{1-10}$ linear, branched or cyclic alkyl), benzoyl, phenylacetyl and substituted benzoyl and phenylacetyl, alkoxycarbonyl (to give alkyl carbonate esters), dialkylcarbamoyl and N—(N, N-dialkylaminoethyl)-N-alkylcarbamoyl (to give carbamates), N, N-dialkylaminoacetyl and carboxyacetyl.

In some embodiments, the nalbuphine used in the formulations and methods of the present disclosure is a pharmaceutically acceptable co-crystal of nalbuphine.

Formulations

The methods of the present disclosure can employ various formulations for administration to patients, e.g., humans and animals in unit dosage forms, such as tablets, capsules, pills, powders, granules, sterile parenteral solutions or suspensions, inhalable dry powders, dispersions, solutions or suspensions, and oral solutions or suspensions, and oil-water emulsions containing suitable quantities of nalbuphine, or pharmaceutically acceptable salts or esters thereof.

Oral pharmaceutical dosage forms can be either solid or liquid. The solid dosage forms can be tablets, capsules, granules, and bulk powders. Types of oral tablets include compressed, chewable lozenges and tablets, which can be enteric-coated, sugar-coated or film-coated. Capsules can be hard or soft gelatin capsules, while granules and powders can be provided in non-effervescent or effervescent form with the combination of other ingredients known to those skilled in the art. In other embodiments, the oral dosage form may be an osmotic-controlled release oral delivery system (OROS). In other embodiments, the oral dosage form may include matrix-embedded dosage forms or related devices. In some embodiments, the present oral dosage forms may include orally-disintegrating tablets.

Pharmaceutically acceptable carriers utilized in tablets include binders, lubricants, diluents, disintegrating agents, coloring agents, flavoring agents, and wetting agents.

Liquid oral dosage forms include aqueous solutions, emulsions, suspensions, solutions and/or suspensions reconstituted from non-effervescent granules and effervescent preparations reconstituted from effervescent granules.

Aqueous solutions include, for example, elixirs and syrups. Emulsions can be either oil-in water or water-in-oil. Elixirs are clear, sweetened, hydroalcoholic preparations. Pharmaceutically acceptable carriers used in elixirs include solvents. Syrups can be concentrated aqueous solutions of a sugar, for example, sucrose, and can contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions can use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, can include organic acids and a source of carbon dioxide. Coloring and flavoring agents can be used in all of the above dosage forms.

Parenteral administration of the formulations of the present disclosure includes intravenous, subcutaneous and intramuscular administrations of immediate, sustained (e.g., depot), extended, and/or modified release formulations (e.g., as described herein). Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

The concentration of the pharmaceutically active compound can be adjusted so that an injection provides an effective amount to produce the desired pharmacological effect. The exact dose depends on the age, weight and condition of the patient or animal, as is known in the art. The unit-dose parenteral preparations are packaged in an ampoule or a syringe with a needle. All preparations for parenteral administration must be sterile, as is known and practiced in the art. Illustratively, intravenous or intraarterial infusion of a sterile aqueous solution containing nalbuphine is an effective mode of administration.

Pharmaceutical dosage forms for rectal administration can be rectal suppositories, capsules and tablets for systemic effect. Rectal suppositories as used herein mean solid bodies for insertion into the rectum which melt or soften at body temperature releasing the pharmacologically and/or therapeutically active ingredients contained in the composition of this disclosure. Pharmaceutically acceptable substances utilized in rectal suppositories are bases or vehicles and agents to raise the melting point. Examples of bases include cocoa butter (theobroma oil), glycerin-gelatin, carbowax, polyoxyethylene glycol and mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

The compositions employed in the present methods can relieve cough or dyspnea when inhaled by a patient in need thereof. Relief can be temporary or permanent, and can even be evident after a single dose of the composition.

Pharmaceutical dosage forms for inhaled administration can be a solution, suspension, or dry powder for local/topical and/or systemic effect. The dry powder may be used in the form of dry powders or in the form of stabilized dispersions comprising a non-aqueous phase. Methods of preparing and using dry powder compositions for inhaled administration are disclosed in U.S. Pat. Nos. 5,874,064 and 5,855,913 and U.S. Patent Application Publication No. 2008/0160092, which are hereby incorporated by reference in their entirety for all purposes. Methods of preparing and using stabilized dispersions are described in U.S. Pat. Nos. 6,946,117 and 6,565,885 and U.S. Patent Application Publication Nos. 2010/0329984 and 2004/0241101, which are hereby incorporated by reference in their entirety for all purposes.

The dry powder, stabilized dispersion, solution, or suspension may be used in conjunction with metered dose inhalers (MDIs), dry powder inhalers (DPIs), atomizers, or nebulizers to provide for inhaled delivery (e.g., intratracheally or intranasally).

Compositions of this disclosure intended for inhaled administration contain an amount of the composition effective to deliver an antitussive, anti-breathlessness or anti-dyspneic amount, typically at a concentration of between about 0.01% w/w to about 80% w/w. The balance of the composition may be a suitable vehicle (such as water, a suitable organic solvent or other suitable solvent or buffer) or one or more pharmaceutical carriers. The compositions that are formulated as dry powders, stabilized dispersions, solutions, or suspensions can administered intratracheally or intranasally.

Compositions should be administered in an amount sufficient to provide relief from cough, breathlessness, or dyspnea that is within safety guidelines established by the FDA. Determining the appropriate amount to administer to a patient is within the skill of the person of ordinary skill in the art in association with teachings provided by the present disclosure.

Pharmaceutical excipients or vehicles suitable for administration of the compositions include any such carriers known to those skilled in the art to be suitable for the particular mode of administration. The nalbuphine can be included in the carriers in amounts sufficient to exert a therapeutically useful effect without serious toxic effects on the treated individual.

Sustained Release

Nalbuphine formulations that can be employed in the present methods include oral sustained release nalbuphine formulations as described in U.S. Provisional Pat. Appl. Nos. 60/772,466, 60/710,772, and 62/011,936; U.S. patent application Ser. No. 11/509,347 (published as US 2007/0048376), Ser. No. 12/154,496 (published as US 2009/0030026), and Ser. No. 14/738,550; and PCT Appl. No. PCT/US2015/035650; each of which is incorporated herein by reference in their entireties.

"Sustained release" or "extended release" means that the nalbuphine or pharmaceutically acceptable salt, solvate or ester thereof is released from the formulation at a controlled rate so that therapeutically beneficial blood levels (but below toxic levels) of the nalbuphine or pharmaceutically acceptable salt, solvate or ester thereof are maintained over an extended period of time. Alternatively, "sustained release" or "extended release" means that the desired pharmacologic effect is maintained over an extended period of time.

The half-life of nalbuphine injectable formulations (i.e., IV or IM or SC) has been reported to be relatively short, only about 2-3 hours. In some embodiments, the present methods can employ oral sustained release formulations of nalbuphine including an effective amount of nalbuphine or a pharmaceutically acceptable salt, solvate or ester thereof. The oral sustained release formulations can provide a controlled release and a lower $C_{max}$ of nalbuphine over a longer period than observed for bolus injections or immediate release oral formulations (e.g., at least about 8-12 hours). Reducing the frequency of dosing provides the potential for enhanced patient convenience and compliance with the present methods. The lower dosing frequency also has the potential to provide reduced side effects because the patient may be exposed to lower peak concentrations of agent over time.

Without wishing to be bound by a particular theory, the longer than expected duration of antitussive, anti-breathlessness and anti-dyspneic effect is attributed to the enterohepatic recirculation of nalbuphine. Nalbuphine forms a glucuronic acid or other type of conjugated metabolite in vivo through enzymatic reaction with an enzyme system such as UDP-glucuronyl transferase. It is also possible that enterohepatic recirculation also occurs when parent drug in the bile is released from the gallbladder into the intestine and reabsorbed. Once formed, the conjugated nalbuphine product is thought to be transported into the gastrointestinal tract via biliary secretion whereby the drug conjugate is cleaved liberating nalbuphine, which can be reabsorbed from the intestine. The sustained release formulation can improve the duration of antitussive, anti-breathlessness or anti-dyspneic effect, by more slowly releasing nalbuphine into the in vivo system and allowing more drug to be conjugated and therefore available for recirculation and later reabsorption from the intestine.

The present methods can employ compositions including nalbuphine or a pharmaceutically acceptable salt, solvate or ester thereof and a sustained release delivery system. The sustained release delivery system includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent. Alternatively, in other embodiments, the present methods can employ compositions including nalbuphine or a pharmaceutically acceptable salt, solvate or ester thereof and a sustained release delivery system, which may employ a hydrophobic compound in a sustained release system.

The nalbuphine can be homogeneously dispersed in the sustained release delivery system. In some embodiments, the nalbuphine or pharmaceutically acceptable salt, solvate or ester thereof is present in the composition in an amount of about 1 mg to about 240 mg; about 1 mg to about 150 mg; about 1 mg to about 125 mg; or about 1 mg to about 100 mg. In some embodiments, the nalbuphine or pharmaceutically acceptable salt, solvate or ester thereof is present in the composition in an amount of about 5 mg to about 80 mg; about 10 mg to about 70 mg; about 15 mg to about 60 mg; about 40 mg to about 80 mg; about 50 mg to about 70 mg; or about 45 mg to about 60 mg. In some embodiments, the nalbuphine or pharmaceutically acceptable salt, solvate or ester thereof is present in the composition in an amount of about 15 mg, about 20 mg, about 25 mg, about 30 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, or about 240 mg. In some embodiments, the nalbuphine or pharmaceutically acceptable salt thereof is present in the composition in an amount of about 15 mg, about 30 mg, about 45 mg, about 60 mg, about 90 mg, about 120 mg, or about 180 mg.

In some embodiments, the pharmaceutically acceptable salt of nalbuphine, e.g., nalbuphine HCl, is present in the composition in an amount of about 15 mg, about 30 mg, about 60 mg, about 90 mg, about 120 mg, or about 180 mg. For compositions comprising a pharmaceutically acceptable salt of nalbuphine, the amount of nalbuphine in said compositions may be expressed as the Equivalent Amount of Nalbuphine Free Base, which is the calculated amount of nalbuphine free base in the composition based on the actual amount of the pharmaceutically acceptable salt of nalbuphine in the composition. The amount of the Equivalent Amount of Nalbuphine Free Base in a composition will vary within the manufacturing process, and the compositions of the present disclosure encompass pharmaceutically-acceptable deviations (i.e., FDA-acceptable) from the nalbuphine content that is recited in the present disclosure.

The following table shows the Equivalent Amount of Nalbuphine Free Base for compositions containing 15 mg, 30 mg, 60 mg, 90 mg, 120 mg, 180 mg and 240 mg of nalbuphine HCl:

| Amount of nalbuphine HCl | Equivalent Amount of Nalbuphine Free Base |
|---|---|
| 15 mg | 13.6 |
| 30 mg | 27.2 |
| 60 mg | 54.4 |
| 90 mg | 81.6 |
| 120 mg | 108.8 |
| 180 mg | 163.2 |
| 240 mg | 217.6 |

The amount of Equivalent Amount of Nalbuphine Free Base is rounded to the nearest 0.1 decimal place using the equation below.

Throughout the present disclosure, the amount of nalbuphine in a composition is generally expressed in terms of the amount of nalbuphine hydrochloride present in a composition. However, the present disclosure contemplates embodiments where the nalbuphine is present in another nalbuphine form (such as a different pharmaceutically acceptable salt and/or ester) and provides about the same Equivalent Amount of Nalbuphine Free Base as the embodiments that are expressly described herein. For example, about 251 mg of nalbuphine citrate (FW=549.57 g/mol) provides about the same Equivalent Amount of Nalbuphine Free Base as about 180 mg of nalbuphine hydrochloride. The Equivalent Amount of Nalbuphine Free Base in said compositions may be calculated by the following formula:

$$\text{Equivalent Amount of Nalbuphine Free Base} = \frac{\text{Mass of Pharmaceutically Acceptable Salt (g)} \times 357.45 \left(\text{Formula Weight of Nalbuphine Free Base}, \frac{g}{mol}\right)}{\text{Formula Weight of Pharmaceutically Acceptable Salt} \left(\frac{g}{mol}\right)}$$

The Equivalent Amount of Nalbuphine Free Base content of the dosage form calculated using the equation above may be adjusted by a pharmaceutically acceptable amount (for example, within an amount permitted by FDA safety standards, which in some embodiments is 1% or less of the calculated Equivalent Amount of Nalbuphine Free Base) to allow product labeling using a whole number integer when referencing the dosage strength. For example, the calculated Equivalent Amount of Nalbuphine Free Base for 240 mg of nalbuphine hydrochloride is 217.6 mg. According to the present disclosure, the nalbuphine content of the composition may be adjusted for a product labelling of 216 mg of Equivalent Amount of Nalbuphine Free Base.

In some embodiments, the nalbuphine or pharmaceutically acceptable salt thereof, e.g., HCL is present in the composition in an amount of about 15 mg, about 30 mg, about 60 mg, about 90 mg, about 120 mg, or about 180 mg.

In some embodiments, the sustained release delivery system is present in the composition in an amount from about 10 mg to about 420 mg; from about 25 mg to about 225 mg; from about 21 mg to about 198 mg; or from about 80 mg to about 200 mg; from about 80 mg to about 220 mg; from about 90 mg to about 210 mg; from about 100 mg to about 200 mg; from about 110 mg to about 190 mg; from about 120 mg to about 180 mg; from about 130 mg to about 170 mg; from about 140 mg to about 160 mg; from about 30 mg to about 60 mg; from about 60 mg to about 180 mg; from about 30 mg to about 180 mg, from about 75 mg to about 150 mg, from about 80 mg to about 160 mg, from about 90 mg to about 150 mg, from about 100 mg to about 140 mg, from about 110 mg to about 130 mg, from about 100 mg to about 300 mg, from about 200 mg to about 300 mg or from about 200 mg to about 250 mg. In some embodiments, the sustained release delivery system is present in the composition in an amount from about 75 mg to about 150 mg.

In some embodiments, the sustained release delivery system is present in the composition in an amount of about 30 mg, about 60 mg, about 75 mg, about 80 mg, about 90 mg, about 100 mg, about 110 mg, about 112 mg, about 115 mg, about 117 mg, about 120 mg, about 125 mg, about 130 mg, about 135 mg, about 140 mg, about 145 mg, about 150 mg, about 160 mg, about 170 mg, about 180 mg, about 190 mg, about 200 mg, about 210 mg, about 220 mg, about 225 mg, about 230 mg, about 240 mg, about 250 mg, about 260 mg, about 270 mg, about 280 mg, about 300 mg, about 320 mg, about 340 mg, about 360 mg, about 380 mg, about 400 mg or about 420 mg. In some embodiments, the sustained release delivery system is present in the composition in an amount of about 112 mg.

The ratio of nalbuphine or pharmaceutically acceptable salt, solvate or ester thereof in the compositions to the sustained release delivery system is generally from about 4:1 to about 1:25. In some embodiments, the ratio of nalbuphine or pharmaceutically acceptable salt, solvate or ester thereof to the sustained release delivery system is generally from about 2.5:1 to about 1:4. In some embodiments, the ratio of nalbuphine or pharmaceutically acceptable salt, solvate or ester thereof to the sustained release delivery system is generally from about 5:1 to about 1:5, about 4:1 to about 1:4, about 3:1 to about 1:3, about 2:1 to about 1:2, about 1:1 to about 1:5, about 1:1 to about 1:4, about 1:1 to about 1:3, about 1:1 to about 1.2, and about 1:2 to about 1:3. In some embodiments, the ratio of nalbuphine or pharmaceutically acceptable salt, solvate or ester thereof to the sustained release delivery system is about 1:1, about 1:2, about 1:2.5, about 1:3, about 1:4, or about 1:5.

In some embodiments, at least one hydrophilic compound is present in the sustained release delivery system in an amount of about 5% to about 80% by weight; the at least one cross-linking agent is present in the sustained release delivery system in an amount of about 0.5% to about 80% by weight; and the at least one pharmaceutical diluent is present in the sustained release delivery system in an amount of about 20% to about 80% by weight. In some embodiments, the at least one hydrophilic compound is present in the sustained release delivery system in an amount of about 8% to about 31% by weight; the at least one cross-linking agent is present in the sustained release delivery system in an amount of about 12% to about 47% by weight; and the at least one pharmaceutical diluent is present in the sustained release delivery system in an amount of about 20% to about 78% by weight. In some embodiments, the at least one hydrophilic compound is present in the sustained release delivery system in an amount of about 10% to about 20% by weight; the at least one cross-linking agent is present in the sustained release delivery system in an amount of about 15% to about 25% by weight; and the at least one pharmaceutical diluent is present in the sustained release delivery system in an amount of about 50% to about 85% by weight. In some embodiments, the at least one hydrophilic compound is present in the sustained release delivery system in an amount of about 8%, about 9%, about 10%, about 11%, about 12%, about 13%, about 14%, about 15%, about 16%, about 17%, about 18%, about 19%, about 20%, about 22%, about 24%, about 26%, about 28%, about 30%, about 32%, about 34%, or about 36% by weight; the at least one cross-linking agent is present in the sustained release delivery system in an amount of about 10%, about 11%, about 12%, about 13%, about 14%, about 15%, about 16%, about 17%, about 18%, about 19%, about 20%, about 22%, about 24%, about 26%, about 28%, about 30%, about 32%, about 33%, about 34%, or about 35% by weight; and the at least one pharmaceutical diluent is present in the sustained release delivery system in an amount of about 40%, about 45%, about 50%, about 55%, about 60%, about 65%, about 70%, about 80%, or about 85% by weight.

In some embodiments, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cross-linking agent is present in the sustained release delivery system in an amount of about 15%, about 16%, about 17%, about 18%, about 19%, about 20%, or about 22% by weight; and the at least one pharmaceutical diluent is present in the sustained release delivery system in an amount of about 55%, about 60%, about 65%, about 70%, about 80%, or about 85% by weight. In some embodiments, the at least one hydrophilic compound is present in the sustained release delivery system in an amount of about 8%, about 12%, or about 20% by weight; the at least one cross-linking agent is present in the sustained release delivery system in an amount of about 12%, about 18%, or about 30% by weight; and the at least one pharmaceutical diluent is present in the sustained release delivery system in an amount of about 40%, about 60%, or about 70% by weight.

In some embodiments, nalbuphine is in the form of any pharmaceutically acceptable salt known in the art, in an amount which provides an equivalent amount of nalbuphine free base as described herein. Exemplary pharmaceutically acceptable salts include without limitation hydrochloric, sulfuric, nitric, phosphoric, hydrobromic, maleic, malic, ascorbic, citric, tartaric, pamoic, lauric, stearic, palmitic, oleic, myristic, lauryl sulfuric, napthalenesulfonic, linoleic, linolenic acid, and the like. In some embodiments, nalbuphine is in the form of a hydrochloride salt.

The sustained release delivery system includes at least one hydrophilic compound. The hydrophilic compound preferably forms a gel matrix that releases the nalbuphine or the pharmaceutically acceptable salt, solvate or ester thereof at a sustained rate upon exposure to liquids. The rate of release of the nalbuphine or the pharmaceutically acceptable salt, solvate or ester thereof from the gel matrix depends on the drug's partition coefficient between the components of the gel matrix and the aqueous phase within the gastrointestinal tract. The weight ratio of nalbuphine to hydrophilic compound is generally in the range of about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, and about 2:1 to about 1:2. In some embodiments, the weight ratio of nalbuphine to hydrophilic compound is in the range of about 10:1 to about 1:1, about 10:1 to about 2:1, about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, and about 2:1 to about 1:1. In some embodiments, the weight ratio of nalbuphine to hydrophilic compound is in the range of about 6:1 to about 1:1, about 5:1 to about 2:1, about 4:1 to about 3:1, about 4:1 to about 2:1, and about 5:1 to about 2:1. In some embodiments, the weight ratio of nalbuphine to hydrophilic compound is about 1:5, about 1:4.5, about 1:4.4, about 1:4, about 1:3.5, about 1:3.3, about 1:3, about 1:2.5, about 1:2, about 1:1, and about 1:1.5.

The sustained release delivery system generally includes the hydrophilic compound in an amount of about 5% to about 80% by weight. In some embodiments, the sustained release delivery system generally includes the hydrophilic compound in an amount of about 5% to about 30%, about 8% to about 31%, about 10% to about 20%, about 20% to about 60%, or about 40% to about 60% by weight. In some embodiments, the sustained release delivery system includes the hydrophilic compound in an amount of about 8% to about 31% by weight. In some embodiments, the sustained release delivery system includes the hydrophilic compound in an amount of about 10% to about 20% by weight. In some embodiments, the sustained release delivery system includes the hydrophilic compound in an amount of about 10%, about 11%, about 12%, about 13%, about 14%, about 15%, about 16%, about 17%, about 18%, about 19%, or about 20% by weight. In some embodiments, the sustained release delivery system includes the hydrophilic compound in an amount of about 12% by weight. In some embodiments, the sustained release delivery system includes the hydrophilic compound in an amount of about 8% by weight. In some embodiments, the sustained release delivery system includes the hydrophilic compound in an amount of about 20% by weight. In some embodiments, the sustained release delivery system includes the hydrophilic compound in an amount of about 28% by weight.

The hydrophilic compound is any pharmaceutically acceptable compound known in the art to be hydrophilic. Exemplary hydrophilic compounds include without limitation pharmaceutically acceptable gums, cellulose ethers, polyvinyl pyrrolidone, protein-derived compounds, and mixtures thereof. Exemplary gums include without limitation heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include without limitation hydroxyalkyl celluloses and carboxyalkyl celluloses. In some embodiments, cellulose ethers include hydroxyethyl celluloses, hydroxypropyl celluloses, hydroxypropylmethyl-celluloses, carboxy methylcelluloses, and mixtures thereof. In some embodiments, the hydrophilic compound is a gum. In other embodiments, the hydrophilic compound is a heteropolysaccharide gum. In further embodiments, the hydrophilic compound is a xanthan gum or derivative thereof. Derivatives of xanthan gum include without limitation, for example, deacylated xanthan gum, the carboxymethyl esters of xanthan gum, and the propylene glycol esters of xanthan gum.

In another aspect, the sustained release delivery system further includes at least one cross-linking agent. In some embodiments, the cross-linking agent is a compound that is capable of cross-linking the hydrophilic compound to form a gel matrix in the presence of liquids. As used herein, "liquids" includes, for example, gastrointestinal fluids and aqueous solutions, such as those used for in vitro dissolution testing. The sustained release delivery system generally includes the cross-linking agent in an amount of about 0.5% to about 80% by weight. In some embodiments, the sustained release delivery system generally includes the cross-linking agent in an amount of about 12% to about 47% by weight. In some embodiments, the sustained release delivery system generally includes the cross-linking agent in an amount of about 20% to about 30% by weight. In some embodiments, the sustained release delivery system generally includes the cross-linking agent in an amount of about 15% to about 25% by weight. In some embodiments, the at least one cross-linking agent is present in the sustained release delivery system in an amount of about 15%, about 16%, about 17%, about 18%, about 19%, about 20%, about 21%, about 22%, about 23%, about 24%, or about 25% by weight. In some embodiments, the sustained release delivery system includes the cross-linking agent in an amount of about 18% by weight. In some embodiments, the sustained release delivery system includes the cross-linking agent in an amount of about 12% by weight. In some embodiments, the sustained release delivery system includes the cross-linking agent in an amount of about 30% by weight. In some embodiments, the sustained release delivery system includes the cross-linking agent in an amount of about 42% by weight.

Exemplary cross-linking agents include homopolysaccharides. Exemplary homopolysaccharides include without limitation galactomannan gums, such as guar gum, hydroxypropyl guar gum, and locust bean gum. In some embodiments, the cross-linking agent is a locust bean gum or a guar gum. In other embodiments, the cross-linking agent is an alginic acid derivative or hydrocolloid.

In some embodiments, when the sustained release delivery system includes at least one hydrophilic compound and at least one cross-linking agent, the weight ratio of hydrophilic compound to cross-linking agent is from about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, or about 1:2 to about 2:1. In some embodiments, the weight ratio of hydrophilic compound to cross-linking agent is about 1:5, about 1:4.5, about 1:4, about 1:3.5, about 1:3, about 1:2.5, about 1:2, about 1:1.5, and about 1:1.

When the sustained release delivery system includes at least one hydrophilic compound and at least one cross-linking agent, the weight ratio of the nalbuphine or pharmaceutically acceptable salt, solvate or ester thereof to the sum of the at least one hydrophilic compound and the at least one cross-linking agent is from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, or from about 2:1 to about 1:2. In some embodiments, the weight ratio of the nalbuphine or pharmaceutically acceptable salt, solvate or ester thereof to the sum of the at least one hydrophilic compound and the at least one cross-linking agent is from about 4:1 to about 1:1, from about 4:1 to about 1:1.5, from about 3:1 to about 1:1, or from about 2:1 to about 1:1. In some embodiments, the ratio of the nalbuphine or pharmaceutically acceptable salt, solvate or ester thereof to the sum of the at least one hydrophilic compound and the at least one cross-linking agent is about 5:1, about 4:1 (i.e., 1:0.25), about 3.5:1, about 3:1, about 2.5:1, about 2:1 (i.e., 1:0.5), about 1.9:1, about 1.8:1, about 1.7:1, about 1.6:1, about 1.5:1, about 1.4:1, about 1.3:1, about 1.2:1, about 1.1:1, about 1:1, about 1:1.5, about 1:2, about 1:3, about 1:4, and about 1:5.

The sustained release delivery system further includes one or more pharmaceutical diluents known in the art. Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Nonlimiting examples of water-soluble pharmaceutical diluents include lactose, dextrose, sucrose, or mixtures thereof. The weight ratio of pharmaceutical diluent to hydrophilic compound is generally from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In some embodiments, the weight ratio of pharmaceutical diluent to hydrophilic compound is generally from about 9:1 to about 1:1.5. In some embodiments, the weight ratio of pharmaceutical diluent to hydrophilic compound is about 9:1, about 8.75:1, about 8.5:1, about 8.25:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, or about 1:1.

The sustained release delivery system generally includes one or more pharmaceutical diluents in an amount of about 20% to about 80%, about 30% to about 70%, about 40% to about 70%, or about 40% to about 60%. In some embodiments, the sustained release delivery system includes one or more pharmaceutical diluents in an amount of about 20% to about 70% by weight. In some embodiments, the sustained release delivery system includes one or more pharmaceutical diluents in an amount of about 50% to about 85% by weight. In some embodiments, the sustained release delivery system includes one or more pharmaceutical diluents in an amount of about 55%, about 60%, about 65%, about 70%, about 80%, or about 85% by weight. In some embodiments, the sustained release delivery system includes one or more pharmaceutical diluents in an amount of about 20% by weight. In some embodiments, the sustained release delivery system includes one or more pharmaceutical diluents in an amount of about 30% by weight. In some embodiments, the sustained release delivery system includes one or more pharmaceutical diluents in an amount of about 40% by weight. In some embodiments, the sustained release delivery system includes one or more pharmaceutical diluents in an amount of about 50% by weight. In some embodiments, the sustained release delivery system includes one or more pharmaceutical diluents in an amount of about 60% by weight. In some embodiments, the sustained release delivery system includes one or more pharmaceutical diluents in an amount of about 70% by weight.

In a further aspect, the sustained release delivery system includes one or more cationic cross-linking compounds. In some embodiments, the one or more cationic cross-linking compounds are used instead of the cross-linking agent. In some embodiments, the one or more cationic cross-linking compounds are used in addition to the cross-linking agent. In some embodiments, the one or more cationic cross-linking compounds are used in an amount sufficient to cross-link the hydrophilic compound to form a gel matrix in the presence of liquids. In some embodiments, the one or more cationic cross-linking compounds are present in the sustained release delivery system in an amount of about 0.5% to about 30%, about 0.5% to about 25%, about 0.5% to about 20%, about 0.5% to about 15%, about 0.5% to about 10%, or about 0.5% to about 5% by weight. In some embodiments, the one or more cationic cross-linking compounds are present in the sustained release delivery system in an amount of about 5% to about 20%, about 5% to about 15%, about 6% to about 14%, about 7% to about 13%, about 8% to about 12%, or about 9% to about 11% by weight. In some embodiments, the one or more cationic cross-linking compounds are present in the sustained release delivery system in an amount of about 5%, about 6%, about 7%, about 8%, about 9%, about 10%, about 11%, about 12%, about 13%, about 14%, or about 15% by weight. In some embodiments, the cationic cross-linking compound is present in the sustained release delivery system in an amount of about 10% by weight.

Exemplary cationic cross-linking compounds include without limitation monovalent metal cations, multivalent metal cations, and inorganic salts, including alkali metal and/or alkaline earth metal sulfates, chlorides, borates, bromides, citrates, acetates, lactates, and mixtures thereof. For example, the cationic cross-linking compound include without limitation one or more of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures thereof.

When the sustained release delivery system includes at least one hydrophilic compound and at least one cationic cross-linking compound, the weight ratio of hydrophilic compound to cationic cross-linking compound ranges from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In some embodiments, the weight ratio of hydrophilic compound to cationic cross-linking compound ranges from about 1:3 to about 3:1. In some embodiments, the weight ratio of hydrophilic compound to cationic cross-linking compound is about 3:1, about 2.75:1, about 2.5:1, about 2.25:1, about 2:1, about 1.8:1, about 1.6:1, about 1.4:1, about 1.2:1, about 1:1, about 1:1.25, about 1:1.5, or about 1:2. In some embodiments, the weight ratio of hydrophilic compound to cationic cross-linking compound is about 1:1.25. In some embodiments, the weight ratio of hydrophilic compound to cationic cross-linking compound is about 1.2:1. In some embodiments, the weight ratio of hydrophilic compound to cationic cross-linking compound is about 2:1. In some embodiments, the weight ratio of hydrophilic compound to cationic cross-linking compound is about 2.8:1.

In some embodiments, the at least one hydrophilic compound is present in the sustained release delivery system in an amount of about 5% to about 80% by weight; the at least one cationic cross-linking agent is present in the sustained release delivery system in an amount of about 0.5% to about 30% by weight; and the at least one pharmaceutical diluent is present in the sustained release delivery system in an amount of about 20% to about 80% by weight. In some embodiments, the at least one hydrophilic compound is present in the sustained release delivery system in an amount of about 8% to about 30% by weight; the at least one cationic cross-linking agent is present in the sustained release delivery system in an amount of about 10% by weight; and the at least one pharmaceutical diluent is present in the sustained release delivery system in an amount of about 20% to about 70% by weight. In some embodiments, the at least one hydrophilic compound is present in the sustained release delivery system in an amount of about 5% to about 30% by weight; the at least one cationic cross-linking agent is present in the sustained release delivery system in an amount of about 5% to about 20% by weight; and the at least one pharmaceutical diluent is present in the sustained release delivery system in an amount of about 20% to about 85% by weight. In some embodiments, the at least one hydrophilic compound is present in the sustained release delivery system in an amount of about 10% to about 20% by weight; the at least one cationic cross-linking agent is present in the sustained release delivery system in an amount of about 5% to about 15% by weight; and the at least one pharmaceutical diluent is present in the sustained release delivery system in an amount of about 50% to about 85% by weight.

In some embodiments, the at least one hydrophilic compound is present in the sustained release delivery system in an amount of about 8%, about 9%, about 10%, about 11%, about 12%, about 13%, about 14%, about 15%, about 16%, about 17%, about 18%, about 19%, about 20%, about 22%, about 24%, about 26%, about 28%, or about 30% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, about 16%, about 17%, about 18%, about 19%, or about 20%, by weight; and the at least one pharmaceutical diluent is present in the sustained release delivery system in an amount of about 40%, about 45%, about 50%, about 55%, about 60%, about 65%, about 70%, about 80%, or about 85% by weight. In some embodiments, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, by weight; and the at least one pharmaceutical diluent is present in the sustained release delivery system in an amount of about 55%, about 60%, about 65%, about 70%, about 80%, or about 85% by weight. In some embodiments, the at least one hydrophilic compound is present in the sustained release delivery system in an amount of about 8%, about 12%, or about 20% by weight; the at least one cationic cross-linking agent is present in the sustained release delivery system in an amount of about 10%, about 12%, or about 14% by weight; and the at least one pharmaceutical diluent is present in the sustained release delivery system in an amount of about 40%, about 60%, or about 70% by weight.

In some embodiments, the sustained release delivery system includes about 0.5% to about 80% locust bean gum, about 5% to about 80% xanthan gum, about 20% to about 80% mannitol and about 0.5% to 80% calcium sulfate dihydrate. In some embodiments, the sustained release delivery system includes about 12% to about 47% locust bean gum, about 8% to about 31% xanthan gum, about 20% to about 78% mannitol and about 0.5% to 25% calcium sulfate dihydrate. In some embodiments, the sustained release delivery system includes about 15% to about 25% locust bean gum, about 10% to about 20% xanthan gum, about 50% to about 85% mannitol and about 5% to 15% calcium sulfate dihydrate. In some embodiments, the sustained release delivery system includes about 18% locust bean gum, about 12% xanthan gum, about 60% mannitol and about 10% calcium sulfate dihydrate. In some embodiments, the sustained release delivery system includes about 12% locust bean gum, about 8% xanthan gum, about 70% mannitol and about 10% calcium sulfate dihydrate. In some embodiments, the sustained release delivery system includes about 20% locust bean gum, about 30% xanthan gum, about 40% mannitol and about 10% calcium sulfate dihydrate. In some embodiments, the sustained release delivery system includes about 30% locust bean gum, about 20% xanthan gum, about 40% mannitol and about 10% calcium sulfate dihydrate. In some embodiments, the sustained release delivery system includes about 42% locust bean gum, about 28% xanthan gum, about 20% mannitol and about 10% calcium sulfate dihydrate.

Two properties of the components of this sustained release system (e.g., the at least one hydrophilic compound and the at least one cross-linking agent; or the at least one hydrophilic compound and at least one cationic cross-linking compound) are that it forms a gel matrix upon exposure to liquids are fast hydration of the compounds/agents and the ability to form a gel matrix having a high gel strength. These two properties, which are needed to achieve a slow release gel matrix, are maximized by the particular combination of compounds (e.g., the at least one hydrophilic compound and the at least one cross-linking agent; or the at least one hydrophilic compound and the at least one cationic cross-linking compound). For example, hydrophilic compounds (e.g., xanthan gum) have excellent water-wicking properties that provide fast hydration. The combination of hydrophilic compounds with materials that are capable of cross-linking the rigid helical ordered structure of the hydrophilic compound (e.g., cross-linking agents and/or cationic cross-linking compounds) thereby acts synergistically to provide a higher than expected viscosity (i.e., high gel strength) of the gel matrix.

In some embodiments, the sustained release compositions are further admixed with one or more wetting agents (e.g., polyethoxylated castor oil, polyethoxylated hydrogenated castor oil, polyethoxylated fatty acid from castor oil, polyethoxylated fatty acid from hydrogenated castor oil) one or more lubricants (e.g., magnesium stearate, sodium stearyl fumarate, and the like), one or more buffering agents, one or more colorants, and/or other conventional ingredients.

In some embodiments, compositions employed in the present methods can contain additional pharmaceutical excipients. For example, in some embodiments, fumaric acid can be added to the formulations described herein.

In other embodiments, a non-functional coating, e.g., Opadry® can be added to the compositions described herein.

In some embodiments, the compositions described herein further include a second hydrophilic compound. In some embodiments, the second hydrophilic compound is a cellulose ether. In some embodiments, the second hydrophilic compound is a hydroxyalkyl cellulose or a carboxyalkyl cellulose. In some embodiments, the second hydrophilic compound is a hydroxyethyl cellulose, a hydroxypropyl cellulose, a hydroxypropylmethyl-cellulose, a carboxy methylcellulose, or a mixture thereof. In some embodiments, the second hydrophilic is an ethyl cellulose or wax (e.g., including without limitation cetyl alcohol, stearyl alcohol, white wax, or carnauba wax). The second hydrophilic compound is present in the formulation in an amount ranging from about 5% to about 45%, about 5% to about 25%, about 10% to about 20%, or 12% to about 18% by weight. In some embodiments, the second hydrophilic compound is present in the formulation in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, or about 45%.

In some embodiments, the weight ratio of the second hydrophilic compound to the nalbuphine or pharmaceutically acceptable salt, solvate or ester ranges from about 5:1 to about 1:5, about 4:1 to about 1:4, about 3:1 to about 1:3, about 2:1 to about 1:2, about 1:1 to about 1:3, or about 1:1 to about 1:2. In some embodiments, the weight ratio of the second hydrophilic compound to the nalbuphine or pharmaceutically acceptable salt, solvate or ester is about 5:1, about 4:1, about 3:1, about 2:1, about 1:1, about 1:2, about 1:3, about 1:4, or about 1:5.

In some embodiments, the weight ratio of the second hydrophilic compound to the sustained release delivery system ranges from about 10:1 to about 1:10, about 8:1 to about 1:8, about 6:1 to about 1:6, about 4:1 to about 1:4, about 2:1 to about 1:3, about 1:1 to about 1:10, about 1:1 to about 1:6, or about 1:2 to about 1:6. In some embodiments, the weight ratio of the second hydrophilic compound to the sustained release delivery system is about 10:1, about 8:1, about 6:1, about 4:1, about 2:1, about 1:1, about 1:1.5, about 1:2, about 1:2.5, about 1:3, about 1:4, about 1:5, about 1:6, about 1:7, about 1:8, about 1:9 or about 1:10.

In some embodiments, the oral sustained release solid dosage formulations including from about 1 mg to 200 mg nalbuphine hydrochloride and about 10 mg to about 420 mg of a sustained release delivery system. In these embodiments, the sustained release delivery system includes about 12% to about 42% locust bean gum; about 8.0% to about 28% xanthan gum; about 20% to about 70% mannitol; and about 5% to about 20% calcium sulfate dihydrate. In some embodiments, the present methods can employ oral sustained release solid dosage formulations including from about 5 mg to about 80 mg nalbuphine hydrochloride and about 80 mg to about 360 mg of a sustained release delivery system. In some embodiments, the present methods can employ oral sustained release solid dosage formulations including from about 50 mg to about 150 mg nalbuphine hydrochloride and about 100 mg to about 300 mg of a sustained release delivery system.

In some embodiments, the present methods employ oral sustained release solid dosage formulations including about 15 mg nalbuphine hydrochloride, and from about 25 mg to about 225 mg, for example about 195 mg, of a sustained release delivery system. In these embodiments, the sustained release delivery system includes about 14% locust bean gum; about 9% xanthan gum; about 47% mannitol; and about 8% calcium sulfate dihydrate.

In some embodiments, the present methods employ oral sustained release solid dosage formulations including about 30 mg nalbuphine hydrochloride, and from about 25 mg to about 225 mg, for example about 180 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 60 mg nalbuphine hydrochloride, and from about 25 mg to about 225 mg, for example about 120 mg, of a sustained release delivery system. In these embodiments, the sustained release delivery system includes about 10% locust bean gum; about 12% xanthan gum; about 60% mannitol; and about 10% calcium sulfate dihydrate.

In some embodiments, the present methods employ oral sustained release solid dosage formulations including from about 5 mg to about 80 mg nalbuphine hydrochloride and about 80 mg to about 360 mg of a sustained release delivery system.

In some embodiments, the present methods employ oral sustained release solid dosage formulations including about 120 mg nalbuphine hydrochloride, and from about 25 mg to about 250 mg, for example about 240 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 30 mg nalbuphine hydrochloride, and from about 25 mg to about 350 mg, for example about 270 mg or about 360 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 45 to about 60 mg nalbuphine hydrochloride and from about 100 mg to about 200 mg of a sustained release delivery system. In these embodiments, the sustained release delivery system includes about 15% to about 25% locust bean gum; about 10% to about 20% xanthan gum; about 50% to about 85% mannitol; and about 5% to about 15% calcium sulfate dihydrate.

In some embodiments, the present methods employ oral sustained release solid dosage formulations including about 30 mg nalbuphine hydrochloride, about 32.4 mg locust bean gum; about 21.6 mg xanthan gum; about 108 mg mannitol; about 18 mg calcium sulfate dihydrate, about 35 mg hydroxypropylcellulose, and about 1.9 mg magnesium stearate.

In some embodiments, the present methods employ oral sustained release solid dosage formulations including about 29.8 mg nalbuphine hydrochloride, about 32.2 mg locust bean gum; about 21.4 mg xanthan gum; about 107 mg mannitol; about 18 mg calcium sulfate dihydrate, about 35 mg hydroxypropylcellulose, and about 1.9 mg magnesium stearate.

In some embodiments, the present methods employ oral sustained release solid dosage formulations including about 60 mg nalbuphine hydrochloride, about 21.6 mg locust bean gum; about 14.4 mg xanthan gum; about 72 mg mannitol; about 12 mg calcium sulfate dihydrate, about 30 mg hydroxypropylcellulose, and about 1.6 mg magnesium stearate.

In some embodiments, the present methods employ oral sustained release solid dosage formulations including about 59.5 mg nalbuphine hydrochloride, about 21.4 mg locust bean gum; about 14.3 mg xanthan gum; about 71 mg mannitol; about 12 mg calcium sulfate dihydrate, about 30 mg hydroxypropylcellulose, and about 1.6 mg magnesium stearate.

In some embodiments, the present methods employ oral sustained release solid dosage formulations including about 120 mg nalbuphine hydrochloride, about 43.2 mg locust bean gum; about 28.8 mg xanthan gum; about 144 mg mannitol; about 24 mg calcium sulfate dihydrate, about 60 mg hydroxypropylcellulose, and about 3.2 mg magnesium stearate.

In some embodiments, the present methods employ oral sustained release solid dosage formulations including about 119.0 mg nalbuphine hydrochloride, about 42.9 mg locust bean gum; about 25.6 mg xanthan gum; about 143 mg mannitol; about 24 mg calcium sulfate dihydrate, about 60 mg hydroxypropylcellulose, and about 3 mg magnesium stearate.

In some embodiments, the present methods employ oral sustained release solid dosage formulations including about 180 mg nalbuphine hydrochloride, about 64.8 mg locust bean gum; about 43.2 mg xanthan gum; about 216 mg mannitol; about 36 mg calcium sulfate dihydrate, about 90 mg hydroxypropylcellulose, about 5 mg magnesium stearate, and about 25 mg fumaric acid.

In some embodiments, the present methods employ oral sustained release solid dosage formulations including about 180 mg nalbuphine hydrochloride, about 48.6 mg locust bean gum; about 32.4 mg xanthan gum; about 162 mg mannitol; about 27 mg calcium sulfate dihydrate, about 60 mg hydroxypropylcellulose, about 4 mg magnesium stearate, and about 25 mg fumaric acid.

In some embodiments, the present methods employ oral sustained release solid dosage formulations including about 178.5 mg nalbuphine hydrochloride, about 48.2 mg locust bean gum; about 32.2 mg xanthan gum; about 161 mg mannitol; about 27 mg calcium sulfate dihydrate, about 60 mg hydroxypropylcellulose, about 4 mg magnesium stearate, and about 25 mg fumaric acid.

In some embodiments, the present methods employ oral sustained release solid dosage formulations including about 30 mg nalbuphine hydrochloride, about 32.4 mg locust bean gum; about 21.6 mg xanthan gum; about 108 mg mannitol; about 18 mg calcium sulfate dihydrate, about 35 mg hydroxypropylcellulose, about 1.9 mg magnesium stearate, and about 7.4 mg Opadry II White.

The sustained release formulations of nalbuphine are orally administrable solid dosage formulations. Nonlimiting examples of oral solid dosage formulations include tablets, capsules including a plurality of granules, sublingual tablets, powders, granules, syrups, and buccal dosage forms or devices (e.g., buccal patches, tablets, etc.). In some embodiments, tablets have an enteric coating or a hydrophilic coating.

The sustained release delivery system is prepared by dry granulation or wet granulation, before the nalbuphine or pharmaceutically acceptable salt, solvate or ester thereof is added, although the components can be held together by an agglomeration technique to produce an acceptable product. In the wet granulation technique, the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules of the sustained release delivery system. Thereafter, the sustained release delivery system is mixed in the desired amounts with the nalbuphine or the pharmaceutically acceptable salt, solvate or ester thereof and, optionally, one or more wetting agents, one or more lubricants, one or more buffering agents, one or more coloring agents, one or more second hydrophilic compounds, or other conventional ingredients, to produce a granulated composition. The sustained release delivery system and the nalbuphine can be blended with, for example, a high shear mixer. The nalbuphine is preferably finely and homogeneously dispersed in the sustained release delivery system. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

In some embodiments, the nalbuphine formulation is prepared by dry granulation or wet granulation. The components of the sustained release delivery system are added, along with the nalbuphine or a pharmaceutically acceptable salt, solvate or ester thereof. Alternatively, all of the components can be held together by an agglomeration technique to produce an acceptable product. In the wet granulation technique, nalbuphine or pharmaceutically salt, solvate or ester thereof and the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules. Optionally, one or more wetting agents, one or more lubricants, one or more buffering agents, one or more coloring agents, one or more second hydrophilic compounds, or other conventional ingredients, are also added to the granulation. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

The average particle size of the granulated composition is from about 50 µm to about 400 µm by weight. In some embodiments, the average particle size by weight is from about 185 µm to about 265 µm. The average density of the granulated composition is from about 0.3 g/mL to about 0.8 g/mL. In some embodiments, the average density is from about 0.5 g/mL to about 0.7 g/mL. The tablets formed from the granulations are generally from about 4 Kp to about 22 Kp hardness. The average flow of the granulations is from about 25 to about 40 g/sec.

In some embodiments, the present methods can employ a multilayer solid dosage form, in which the layers are formulated to release the nalbuphine hydrochloride at different rates. For example, in some embodiments, the second layer is an extended release layer that includes nalbuphine or a pharmaceutically acceptable salt, solvate or ester thereof and a sustained release delivery system designed to release the nalbuphine or the pharmaceutically acceptable salt, solvate or ester thereof at a controlled rate so that therapeutically effective blood levels are maintained over an extended period of time (e.g., from about 8 to about 12 hours). The first layer is an immediate release layer that includes a formulation of nalbuphine or a pharmaceutically acceptable salt, solvate or ester thereof designed to release the nalbuphine or the pharmaceutically acceptable salt, solvate or ester thereof at a rate that is faster than the rate of the second layer to achieve a therapeutically effective blood level in an immediate period of time (e.g., from about 1 to about 2 hours). In some embodiments, the first layer includes a sustained release delivery system. In some embodiments, the first layer does not include a sustained release delivery system.

In some embodiments, the weight ratio of the second layer to the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In some embodiments, the weight ratio of the second layer to the first layer is about 5:1 to about 1:5. In a further embodiment, the weight ratio of the second layer to the first layer is about 1:1 to about 1:2. In some embodiments, the weight ratio of the second layer to the first layer is about 1:1, about 1:1.2, about 1:1.4, about 1:1.6, about 1:1.8, or about 1:2. In some embodiments, the weight ratio of the second layer to the first layer is about 1:2. In some embodiments, the weight ratio of the second layer to the first layer is about 1:1.4. In some embodiments, the weight ratio of the second layer to the first layer is about 3:1, about 2.5:1, about 2:1, about 1.5:1. In some embodiments, the weight ratio of the second layer to the first layer is about 2.5:1.

The sustained release delivery system of the multilayer dosage form includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent. In some embodiments, when the first layer includes a sustained release delivery system, the sustained release delivery system of the first layer includes the same components as the sustained release delivery system of the second layer (e.g., both the first and second layers are one of embodiments (i)-(iii), listed above). In other embodiments, the sustained release delivery system of the first layer includes different components as the sustained release delivery system of the second layer (e.g., the first layer is embodiment (i), listed above, while the second layer is embodiment (iii), listed above). It is recognized that the sustained release delivery system of either layer can be one of embodiments (i)-(iii)

listed above. Moreover, it is recognized that in some embodiments, the first layer does not include a sustained release delivery system.

The sustained release delivery system is generally present in the second layer (e.g., extended release layer) in an amount ranging from about 10 mg to about 420 mg. In some embodiments, the sustained release delivery system is present in the second layer in an amount ranging from about 110 mg to about 200 mg. In some embodiments, the sustained release delivery system is present in the second layer in an amount ranging from about 110 mg to about 150 mg. In some embodiments, the sustained release delivery system is present in the second layer in an amount ranging from about 90 mg to about 150 mg. In some embodiments, the sustained release delivery system is present in the second layer in an amount of about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg. In some embodiments, the sustained release delivery system is present in the second layer in an amount of about 123 mg. In some embodiments, the sustained release delivery system is present in the second layer in an amount of about 101 mg. In some embodiments, the sustained release delivery system is present in the second layer in an amount of about 92 mg. In some embodiments, the sustained release delivery system is present in the second layer in an amount of about 112.5 mg. In some embodiments, the sustained release delivery system is present in the second layer in an amount of about 135 mg. In some embodiments, the sustained release delivery system is present in the second layer in an amount of about 150 mg.

Nalbuphine or a pharmaceutically acceptable salt, solvate or ester thereof is generally present in the second layer in an amount ranging from about 15 mg to about 60 mg. In some embodiments, nalbuphine or a pharmaceutically acceptable salt, solvate or ester thereof is present in the second layer in an amount ranging from about 30 mg to about 60 mg. In some embodiments, nalbuphine or a pharmaceutically acceptable salt, solvate or ester thereof is present in the second layer in an amount ranging from about 45 mg to about 60 mg. In some embodiments, nalbuphine or a pharmaceutically acceptable salt, solvate or ester thereof is present in the second layer in an amount of about 15 mg. In some embodiments, nalbuphine or a pharmaceutically acceptable salt, solvate or ester thereof is present in the second layer in an amount of about 30 mg. In some embodiments, nalbuphine or a pharmaceutically acceptable salt, solvate or ester thereof is present in the second layer in an amount of about 45 mg. In some embodiments, nalbuphine or a pharmaceutically acceptable salt, solvate or ester thereof is present in the second layer in an amount of about 15 mg, about 30 mg, about 60 mg, about 90 mg, about 120 mg, or about 180 mg.

In some embodiments, the weight ratio of nalbuphine or a pharmaceutically acceptable salt, solvate or ester thereof to the sustained release delivery system in the second layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2. In some embodiments, the weight ratio of nalbuphine or a pharmaceutically acceptable salt, solvate or ester thereof to the sustained release delivery system in the second layer is about 1:2 to about 1:4. In some embodiments, the weight ratio of nalbuphine or a pharmaceutically acceptable salt, solvate or ester thereof to the sustained release delivery system in the second layer is about 1:1 to about 1:5. In some embodiments, the weight ratio of nalbuphine or a pharmaceutically acceptable salt, solvate or ester thereof to the sustained release delivery system in the second layer is about 1: 1, about 1:1.2, about 1:1.4, about 1:1.6, about 1:1.8, about 1:2, about 1:2.5, about 1:3, or about 1:3.5. In some embodiments, the weight ratio of nalbuphine or a pharmaceutically acceptable salt, solvate or ester thereof to the sustained release delivery system in the second layer is about 1:2.5. In some embodiments, the weight ratio of nalbuphine or a pharmaceutically acceptable salt, solvate or ester thereof to the sustained release delivery system in the second layer is about 1:3.3. In a further embodiment, the weight ratio of nalbuphine or a pharmaceutically acceptable salt, solvate or ester thereof to the sustained release delivery system in the second layer is about 1:3.

In some embodiments, the ratio of nalbuphine or a pharmaceutically acceptable salt, solvate or ester thereof to the sustained release delivery system in the second layer is about 1:2.

When the sustained release delivery system is present in the first layer (e.g., immediate release layer), it is generally present in an amount ranging from about 0 mg to about 50 mg. In some embodiments, the sustained release delivery system is present in the first layer in an amount ranging from about 5 mg to about 25 mg or from about 5 mg to about 15 mg. In some embodiments, the sustained release delivery system is present in the first layer in an amount of about 3 mg to about 9 mg. In some embodiments, the sustained release delivery system is present in the first layer in an amount of about 4 mg to about 6 mg. In some embodiments, the sustained release delivery system is present in the first layer in an amount of about 2 mg, about 4 mg, about 6 mg, about 8 mg, about 10 mg, about 12 mg, about 14 mg, about 15 mg, about 16 mg, about 18 mg, about 20 mg about 25 mg, about 30 mg, about 35 mg, about 40 mg, about 45 mg or about 50 mg. In some embodiments, the sustained release delivery system is present in the first layer in an amount of about 6 mg.

In some embodiments, nalbuphine or a pharmaceutically acceptable salt, solvate or ester thereof is generally present in the first layer (e.g., immediate release layer) in an amount ranging from about 5 mg to about 180 mg. In some embodiments, nalbuphine or a pharmaceutically acceptable salt, solvate or ester thereof is present in the first layer in an amount ranging from about 5 mg to about 25 mg or from about 10 mg to about 20 mg. In some embodiments, the nalbuphine or a pharmaceutically acceptable salt, solvate or ester thereof is present in the first layer in an amount of about 5 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg or about 50 mg. In some embodiments, nalbuphine or a pharmaceutically acceptable salt, solvate or ester thereof is present in the first layer in an amount of about 15 mg, about 30 mg, about 60 mg, about 90 mg, about 120 mg, or about 180 mg.

In some embodiments, when the first layer includes a sustained release delivery system, the ratio of nalbuphine or pharmaceutically acceptable salt, solvate or ester thereof to the sustained release delivery system in the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In some embodiments, the ratio of nalbuphine or pharmaceutically acceptable salt, solvate or ester thereof to the sustained release delivery system in the first layer is about 2:1 to about 4:1. In some embodiments, the ratio of nalbuphine or pharmaceutically acceptable salt, solvate or ester thereof to the sustained release delivery system in the first layer is about 5:1, about 4.5:1, about 4:1, about 3.5:1, about 3:1, about 2.5:1, about 2:1, about 1.5:1, or about 1:1. In some embodiments, the ratio of nalbuphine or pharmaceutically acceptable salt, solvate or ester thereof to the sustained release delivery system in the first layer is about 2.5:1. In some embodiments, the ratio of nalbuphine or pharmaceutically acceptable salt, solvate or ester thereof to the sustained release delivery system in the first layer is about 3:1.

In some embodiments, the multilayer dosage form further includes a pharmaceutical disintegrant. The disintegrant promotes the dissolution and absorption of nalbuphine or pharmaceutically acceptable salt, solvate or ester thereof from the immediate release layer. Nonlimiting examples of pharmaceutical disintegrants include croscarmellose sodium, starch glycolate, crospovidone, and unmodified starch. In some embodiments, the disintegrant is in the first layer (i.e., the immediate release layer), of the dosage form. The disintegrant is generally present in the layer in an amount of about 1.5 mg to about 4.5 mg. In some embodiments, the disintegrant is present in an amount of about 3 mg. In some embodiments, the disintegrant is present in the layer in an amount of about 2-10% by weight. In some embodiments, the disintegrant is present in the layer in an amount of about 5% by weight. When the layer contains a sustained release delivery system, the weight ratio of the sustained release delivery system to the disintegrant is in a range of about 5:1 to about 1:5. In some embodiments, the ratio of the sustained release delivery system to the disintegrant is in a range of about 1:1 to about 3:1. In other embodiments, the ratio of the sustained release delivery system to the disintegrant is in a range of about 2:1.

In some embodiments, the multilayer tablets are prepared by first preparing the immediate release layer and extended release layer blends separately. The extended release layer is prepared as described above. The wet granulation of the extended release layer is then dried and milled to an appropriate size. Magnesium stearate is added and mixed with the milled granulation. The immediate release layer is prepared by first mixing the nalbuphine or the pharmaceutically acceptable salt, solvate or ester thereof with one or more diluents (e.g., microcrystalline cellulose). This mix is then optionally mixed with one or more disintegrants. The blend is mixed with magnesium stearate. Finally, the immediate release layer blend and the extended release layer blend are compressed into multi-layer (e.g., bi-layer) tablets.

In some embodiments, the chemistry of certain of the components of the formulation, such as the hydrophilic compound (e.g., xanthan gum), is such that the components are considered to be self-buffering agents which are substantially insensitive to the solubility of the nalbuphine and the pH changes along the length of the gastrointestinal tract. Moreover, the chemistry of the components is believed to be similar to certain known muco-adhesive substances, such as polycarbophil. Muco-adhesive properties are desirable for buccal delivery systems. Thus, the sustained release formulation can loosely interact with the mucin in the gastrointestinal tract and thereby provide another mode by which a constant rate of delivery of the nalbuphine is achieved.

The phenomenon discussed above (muco-adhesive properties) is a mechanism by which the sustained release formulations can interact with the mucin and fluids of the gastrointestinal tract and provide a constant rate of delivery of the nalbuphine.

When measured by USP Procedure Drug Release General Chapter <711> Dissolution, (incorporated by reference herein in its entirety), the sustained release formulations employed in the present methods generally exhibit an in vitro dissolution of about 15% to about 50% by weight nalbuphine after 1 hour, about 45% to about 80% by weight nalbuphine after 4 hours, or at least about 80% by weight nalbuphine after 10 hours. In some embodiments, the in vitro and in vivo release characteristics of the sustained release formulations are modified using mixtures of one or more different water insoluble and/or water soluble compounds, using different plasticizers, varying the thickness of the sustained release film, including providing release-modifying compounds in the coating, and/or by providing passageways through the coating. In some embodiments, the dissolution rate is determined using apparatus USP Type 111/250 mL at pH 6.8, 37° C. and 15 dpm. In some embodiments, the dissolution rate is determined using apparatus USP Type III/250 mL performed in pH change (0-1 hours pH 1.2, after hour 1 pH 4.5, after hour 2 pH 6.8) at 37° C. and 15 dpm.

In some embodiments, the sustained release formulation has an in vitro dissolution of about 50% to about 100% by weight nalbuphine after about 6 hours. In some embodiments, the sustained release formulation has an in vitro dissolution of about 75% to about 100% by weight nalbuphine after about 6 hours. In other embodiments, the sustained release formulation has an in vitro dissolution of about 75% to about 100% by weight nalbuphine from about 6 hours to about 8 hours. In further embodiments, the sustained release formulation has an in vitro dissolution of about 80% to about 100% by weight nalbuphine after about 12 hours. In still other embodiments, the sustained release formulation has an in vitro dissolution of about 80% to about 100% by weight nalbuphine from about 12 hours to about 24 hours. In some embodiments, the sustained release formulation has an in vitro dissolution of about 80% to about 100% after about 8 hours to about 12 hours. In yet other embodiments, the sustained release formulation has an in vitro dissolution of about 15% to about 75% by weight nalbuphine after about 1 hour. In still further embodiments, the sustained release formulation has an in vitro dissolution of about 50% by weight nalbuphine after about 1 hour. In some embodiments, the sustained release formulation has an in vitro dissolution of about 50% by weight nalbuphine after about 1 hour and about 75% to about 100% by weight nalbuphine from about 6 hours to about 8 hours. In some embodiments, the sustained release formulation has an in vitro dissolution of about 50% by weight nalbuphine after about 1 hour and about 75% to about 100% by weight nalbuphine from about 8 hours to about 12 hours. In some embodiments, the sustained release formulation has an in vitro dissolution of about 50% by weight nalbuphine after about 1 hour and about 75% to about 100% by weight nalbuphine from about 12 hours to about 24 hours. In some embodiments, the sustained release formulation has an in vitro dissolution of about 50% by weight nalbuphine after about 1 hour and about 80% to about 100% by weight nalbuphine after about 12 hours.

Where the tablet is a multilayer dosage form having a first extended release layer and a second, immediate release, layer, the sustained release formulation has an in vitro dissolution of about 25% to about 75% by weight nalbuphine after about 1 hour. In some embodiments, the multi-layer dosage form has an in vitro dissolution of about 25% by weight nalbuphine after about 1 hour. In some embodiments, the multilayer dosage form has an in vitro dissolution of about 50% by weight nalbuphine after about 1 hour. In some embodiments, the multilayer dosage form has an in vitro dissolution of about 75% to about 100% nalbuphine after about 6-8 hours. In some embodiments, the multilayer dosage form has an in vitro dissolution of about 75% to about 100% nalbuphine after about 8-12 hours. In some embodiments, the multilayer dosage form has an in vitro dissolution of about 75% to about 100% nalbuphine after about 12-24 hours. In some embodiments, the multilayer dosage form has an in vitro dissolution of about 75% to about 100% nalbuphine after about 12 hours.

In some embodiments, when administered orally to patients having either normal or impaired (e.g., reduced) kidney function, the sustained release formulations described herein exhibit the following in vivo characteristics: (a) a peak plasma level of nalbuphine occurs within about 4 hours to about 6 hours, e.g., for patients with renal impairment, or about 3 hours to about 5 hours, e.g., for patients without renal impairment after administration; (b) onset of nalbuphine antitussive, anti-breathlessness or anti-dyspneic effect from about 30 minutes of dosing to within about 6 hours of dosing; (c) duration of the nalbuphine antitussive, anti-breathlessness or anti-dyspneic effect is about 2 to about 24 hours; and (d) the relative nalbuphine bioavailability is about 0.5, about 1, about 1.5 or between about 0.5 to about 1.5 compared to an orally administered aqueous solution of nalbuphine. The time of onset for an antitussive, anti-breathlessness or anti-dyspneic effect can depend on at least on dosing and the severity of cough, breathlessness, or dyspnea symptoms. In some embodiments, the duration of the nalbuphine antitussive, anti-breathlessness or anti-dyspneic effect is at least about 8 hours. In some embodiments, the duration of the nalbuphine antitussive, anti-breathlessness or anti-dyspneic effect is at least about 9 hours. In some embodiments, the duration of the nalbuphine antitussive, anti-breathlessness or anti-dyspneic effect is at least about 10 hours. In some embodiments, the duration of the nalbuphine antitussive, anti-breathlessness or anti-dyspneic effect is at least about 11 hours. In some embodiments, the duration of the nalbuphine antitussive, anti-breathlessness or anti-dyspneic effect is at least about 12 hours. In some embodiments, the duration of nalbuphine antitussive, anti-breathlessness or anti-dyspneic effect is about 6, hours, 8 hours, 10 hours, 12 hours, 15 hours, or 18 hours. In some embodiments, the relative nalbuphine bioavailability is about 0.94 compared to an orally administered aqueous solution of nalbuphine. In some embodiments, the relative nalbuphine bioavailability is about 1.35 compared to an orally administered aqueous solution of nalbuphine.

In some embodiments, the sustained release nalbuphine formulations provide an oral unit dosage form including nalbuphine or a pharmaceutically acceptable salt, solvate or ester thereof. The oral dosage form provides an antitussive, anti-breathlessness or anti-dyspneic effect over a period of at least about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours. In some embodiments, the oral dosage form provides an antitussive, anti-breathlessness or anti-dyspneic effect over a period of about 6-18 hours, about 8-16 hours, about 8-12 hours, about 8 to about 24 hours, about 12 to about 24 hours, about 18 to about 24 hours, or about 8-10 hours. The oral dosage form provides an antitussive, anti-breathlessness or anti-dyspneic effect over a period of about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours.

In some embodiments, the oral dosage form provides a blood plasma level of nalbuphine characterized by one or more peaks followed by a plateau region. The plateau region is characterized as having a relatively consistent blood plasma level of nalbuphine (e.g., the blood plasma level of nalbuphine does not consistently increase or decrease from time point to time point). In some embodiments, the plateau region is characterized as having a consistent average blood plasma level of nalbuphine. The plateau region is contrasted with the region following the plateau region, in which the blood plasma level of nalbuphine generally decreases from one time point to the next. In some embodiments, the plateau region has a duration of at least about 1 hour, about 2 hours, about 3 hours, about 4 hours, about 5 hours, about 6 hours, about 7 hours, about 8 hours, about 9 hours, about 10 hours, about 11 hours or about 12 hours. In some embodiments, the plateau region has a duration from about 1 hour to about 12 hours, from about 2 hours to about 10 hours, from about 2 hours to about 8 hours, from about 2 hours to about 7 hours or from about 4 hours to about 10 hours, from about 4 hours to about 8 hours, or from about 4 hours to about 6 hours. In some embodiments, the blood plasma level of nalbuphine at each time point in the plateau region ranges from about 75% to about 125% of the mean blood plasma level in the plateau region. In some embodiments, the blood plasma level of nalbuphine at each time point in the plateau region ranges from about 80% to about 120% of the mean blood plasma level in the plateau region. In some embodiments, the blood plasma level of nalbuphine at each time point in the plateau region ranges from about 85% to about 115% of the mean blood plasma level in the plateau region. In some embodiments, the blood plasma level of nalbuphine at each time point in the plateau region ranges from about 90% to about 110% of the mean blood plasma level in the plateau region.

In some embodiments, the minimum blood plasma level of nalbuphine observed during the plateau region is not more than about 25% below the mean blood plasma level for all time points in the plateau region. In some embodiments, the minimum blood plasma level of nalbuphine observed during the plateau region is not more than about 20% below the mean blood plasma level in the plateau region. In some embodiments, the minimum blood plasma level of nalbuphine observed during the plateau region is not more than about 15% below the mean blood plasma level in the plateau region. In some embodiments, the minimum blood plasma level of nalbuphine observed during the plateau region ranges from about 75% to about 100% of the mean blood plasma level in the plateau region. In some embodiments, the minimum blood plasma level of nalbuphine observed during the plateau region ranges from about 80% to about 100% of the mean blood plasma level in the plateau region. In some embodiments, the minimum blood plasma level of nalbuphine observed during the plateau region ranges from about 85% to about 100% of the mean blood plasma level in the plateau region. In some embodiments, the minimum blood plasma level of nalbuphine observed during the plateau region ranges from about 80% to about 95% of the mean blood plasma level in the plateau region.

Co-Therapy

While the compositions can be administered as the sole active pharmaceutical ingredient, in other embodiments they can also be used in combination with one or more ingredients that are known to be therapeutically effective against cough and/or dyspnea and/or compliment the effect of nalbuphine. For example, in some embodiments, the present methods can employ nalbuphine or a pharmaceutically acceptable salt, solvate or ester thereof in conjunction with one or more antitussive, anti-breathlessness or anti-dyspneic agents. In some embodiments, the antitussive agent combined with the nalbuphine, or a pharmaceutically acceptable salt, solvate or ester thereof, include mu opioid agonists such as morphine, codeine, oxycodone, dextromethorphan, lidocaine, tramadol, anti-convulsants and anti-neuropathic pain drugs such as gabapentin, pregabalin, anti-depressants such as amitriptyline, pulmonary anti-fibrotic agents such as Pirfenidone (Esbriet®) and nintedanib) (Ofev®), steroids such as budesonide and prednisone, proton pump inhibitors such as esomeprazole, ipratropium bromide, cromoglicate, cromolyn sodium and thalidomide, kappa opioid agonists such as nalfurafine and difelikefalin, mu opioid antagonists such as naloxone and naltrexone. In some embodiments, the anti-dyspneic agent combined with the nalbuphine, or a pharmaceutically acceptable salt, solvate or ester thereof include anxiolytics such as benzodiazepam and anti-fibrotic agents such as Pirfenidone (Esbriet®) and nintedanib (Ofev®).

In some embodiments, nalbuphine or a pharmaceutically acceptable salt, solvate or ester thereof is not administered in combination with a second antitussive, anti-breathlessness or anti-dyspneic agents, e.g., co-formulated or administered separately.

In some embodiments, nalbuphine or a pharmaceutically acceptable salt, solvate or ester thereof is administered in conjunction with one or more agents used to treat IPF cough, breathlessness or dyspnea. In some embodiments, the agent used to treat IPF cough, breathlessness, or dyspnea is selected from the group consisting of pirfenidone, nintedanib, N-acetylcysteine, cromolyn sodium, thalidomide, gefapixant, serlopitant, and orvepitant.

Dosing

The disclosure provides methods for treating cough, breathlessness, or dyspnea by administering an effective amount of nalbuphine or a pharmaceutically acceptable salt, solvate or ester thereof, to a patient in need thereof. An effective amount is an amount sufficient to eliminate or significantly reduce cough, breathlessness, or dyspnea symptoms or to alleviate those symptoms (e.g., reduce the symptoms, such as cough frequency or breathlessness, compared to the symptoms present prior to treatment). Formulations employed in the present methods can incorporate the nalbuphine in a sustained release formulation such that the formulation provides therapeutically effective blood plasma levels of nalbuphine for the treatment of cough, breathlessness, or dyspnea.

According to some embodiments of the present disclosure, administering of nalbuphine or a pharmaceutically acceptable salt, solvate or ester thereof provides statistically significant therapeutic effect. In some embodiments, the statistically significant therapeutic effect is determined based on one or more standards or criteria provided by one or more regulatory agencies in the United States, e.g., FDA or other countries. In some embodiments, the statistically significant therapeutic effect is determined based on results obtained from regulatory agency approved clinical trial set up and/or procedure.

In some embodiments, the statistically significant therapeutic effect is determined based on a patient population of at least 20, 50, 60, 100, 200, 300, 400, 500, 600, 700, 800, 900, 1000 or 2000. In some embodiments, the statistically significant therapeutic effect is determined based on data obtained from randomized and double-blinded clinical trial set up. In some embodiments, the statistically significant therapeutic effect is determined based on data with a p value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase III clinical trial of the methods provided by the present disclosure, e.g., by FDA in the US.

In some embodiments, the statistically significant therapeutic effect is determined by a randomized double blind clinical trial of patients treated with nalbuphine or a pharmaceutically acceptable salt, solvate or ester thereof and optionally in combination with standard care. In some embodiment, the statistically significant therapeutic effect is determined by a randomized clinical trial and using daytime cough frequency measured using cough count monitor device as primary efficacy parameter and optionally in combination with any other commonly accepted criteria for cough and/or dyspnea assessment.

In general, statistical analysis can include any suitable method permitted by a regulatory agency, e.g., FDA in the US or Europe or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

In some embodiments of present disclosure, the nalbuphine is administered on a once or twice a day basis to provide effective relief of the cough symptoms of chronic cough. In some embodiments, a total daily dose is about 15 mg, about 10 mg, about 30 mg, about 60 mg, about 90 mg, about 120 mg, about 180 mg, about 240 mg, about 360 mg, or about 480 mg. In some embodiments, the patient in need of a treatment of chronic cough is a patient with a lung disease. In some embodiments, the lung disease is an interstitial lung disease. In some embodiments, the interstitial lung disease is selected from the group consisting of idiopathic pulmonary fibrosis, hypersensitivity pneumonitis, sarcoidosis, asbestosis, bronchiolitis obliterans, histiocytosis X, chronic eosinophilic pneumonia, collagen vascular disease, granulomatous vasculitis, Goodpasture's syndrome and, pulmonary alveolar proteinosis. In some embodiments, the interstitial lung disease is selected from the group consisting of idiopathic pulmonary fibrosis, hypersensitivity pneumonitis, sarcoidosis, and asbestosis. In some embodiments, the lung disease is a chronic obstructive pulmonary lung disease (COPD). In some embodiments, the COPD is associated with a condition selected from the group consisting of emphysema, chronic bronchitis and Alpha-1-antitrypsin (AAt) deficiency. In some embodiments, the COPD is associated with an irritant selected from the group consisting of cigarette smoke, secondhand smoke, pipe smoke, air pollution and workplace exposure to dust, smoke or fumes.

In some embodiments of the present disclosure, the nalbuphine is administered on a once or twice a day basis to provide effective relief of the cough symptoms associated with unexplained chronic cough. In some embodiments, a total daily dose is about 30 mg, about 60 mg, about 90 mg, about 120 mg, about 180 mg, about 240 mg, about 360 mg, or about 480 mg.

In some embodiments of the present disclosure, the nalbuphine is administered on a once or twice a day basis to provide effective relief of the symptoms of cough associated with refractory chronic cough. In some embodiments, a total daily dose is about 15 mg, about 20 mg, 30 mg, about 60 mg, about 90 mg, about 120 mg, about 180 mg, about 240 mg, about 360 mg, or about 480 mg.

In some embodiments of the present disclosure, the nalbuphine is administered on a once or twice a day basis to provide effective relief of the symptoms of cough associated with cough hypersensitivity syndrome. In some embodiments, a total daily dose is about 30 mg, about 60 mg, about 90 mg, about 120 mg, about 180 mg, about 240 mg, about 360 mg, or about 480 mg.

In some embodiments of the present disclosure, the nalbuphine is administered on a once or twice a day basis to provide effective relief of the symptoms of cough, breathlessness, or dyspnea associated with idiopathic pulmonary fibrosis. In some embodiments, a total daily dose is about 15 mg, about 10 mg, about 30 mg, about 60 mg, about 90 mg, about 120 mg, about 180 mg, about 240 mg, about 360 mg, or about 480 mg.

Throughout the present disclosure, the methods and doses used therein are generally expressed in terms of an amount of nalbuphine (or other antitussive or antibreathlessness or anti-dyspneic agent) for the "treatment of cough, breathlessness, or dyspnea" without specifying the condition that the cough, breathlessness, or dyspnea is associated with. However, the present disclosure contemplates embodiments where methods and doses are effective for the treatment of cough, breathlessness, or dyspnea associated with a particular condition such as IPF, refractory chronic cough, unexplained chronic cough, hypersensitivity pneumonitis, sarcoidosis, asbestosis, bronchiolitis obliterans, histiocytosis X, chronic eosinophilic pneumonia, collagen vascular disease, granulomatous vasculitis, Goodpasture's syndrome and, pulmonary alveolar proteinosis, COPD (such as COPD is associated with a condition such as emphysema, chronic bronchitis and Alpha-1-antitrypsin (AAt) deficiency or COPD associated with an irritant such as cigarette smoke, secondhand smoke, pipe smoke, air pollution and workplace exposure to dust, smoke or fumes) and other conditions described herein.

In some embodiments, the total daily dose of the nalbuphine can be at least about 15 mg a day for the treatment of cough, breathlessness, or dyspnea. In some embodiments, the total daily dose of the nalbuphine can be at least about 20 mg a day for the treatment of cough, breathlessness, or dyspnea. In some embodiments, the total daily dose of the nalbuphine can be at least about 30 mg a day for the treatment of cough, breathlessness, or dyspnea. In some embodiments, the total daily dose of the nalbuphine can be at least about 40 mg a day for the treatment of cough, breathlessness, or dyspnea. In some embodiments, the total daily dose of the nalbuphine can be at least about 60 mg a day for the treatment of cough, breathlessness, or dyspnea. In some embodiments, the total daily dose of the nalbuphine can be at least about 90 mg a day for the treatment of cough, breathlessness, or dyspnea. In some embodiments, the total daily dose of the nalbuphine can be at least about 120 mg a day for the treatment of cough, breathlessness, or dyspnea. In some embodiments, the total daily dose of the nalbuphine can be at least about 180 mg a day for the treatment of cough, breathlessness, or dyspnea. In some embodiments, the total daily dose of the nalbuphine can be at least about 240 mg a day for the treatment of cough, breathlessness, or dyspnea. In some embodiments, the total daily dose of the nalbuphine can be at least about 360 mg a day for the treatment of cough, breathlessness, or dyspnea.

In some embodiments, the total daily dose of the nalbuphine can be about 15 mg a day for the treatment of cough, breathlessness, or dyspnea. In some embodiments, the total daily dose of the nalbuphine can be about 20 mg a day for the treatment of cough, breathlessness, or dyspnea. In some embodiments, the total daily dose of the nalbuphine can be about 30 mg a day for the treatment of cough, breathlessness, or dyspnea. In some embodiments, the total daily dose of the nalbuphine can be about 40 mg a day for the treatment of cough, breathlessness, or dyspnea. In some embodiments, the total daily dose of the nalbuphine can be about 60 mg a day for the treatment of cough, breathlessness, or dyspnea. In some embodiments, the total daily dose of the nalbuphine can be about 90 mg a day for the treatment of cough, breathlessness, or dyspnea. In some embodiments, the total daily dose of the nalbuphine can be about 120 mg a day for the treatment of cough, breathlessness, or dyspnea. In some embodiments, the total daily dose of the nalbuphine can be about 180 mg a day for the treatment of cough, breathlessness, or dyspnea. In some embodiments, the total daily dose of the nalbuphine can be about 240 mg a day for the treatment of cough, breathlessness, or dyspnea. In some embodiments, the total daily dose of the nalbuphine can be about 360 mg a day for the treatment of cough, breathlessness, or dyspnea. In some embodiments, the total daily dose of the nalbuphine can be about 480 mg a day for the treatment of cough, breathlessness, or dyspnea.

In some embodiments, about 15 mg of the nalbuphine once a day is selected to provide a substantial reduction in cough, breathlessness, or dyspnea. In some embodiments, about 20 mg of the nalbuphine once a day is selected to provide a substantial reduction in cough, breathlessness, or dyspnea. In some embodiments, about 10 mg of the nalbuphine twice a day is selected to provide a substantial reduction in cough, breathlessness, or dyspnea. In some embodiments, about 30 mg of the nalbuphine once a day is selected to provide a substantial reduction in cough, breathlessness, or dyspnea. In some embodiments, about 15 mg of the nalbuphine twice a day is selected to provide a substantial reduction in cough, breathlessness, or dyspnea. In some embodiments, about 40 mg of the nalbuphine once a day is selected to provide a substantial reduction in cough, breathlessness, or dyspnea. In some embodiments, about 20 mg of the nalbuphine twice a day is selected to provide a substantial reduction in cough, breathlessness, or dyspnea. In some embodiments, about 60 mg of the nalbuphine once a day is selected to provide a substantial reduction in cough, breathlessness, or dyspnea. In some embodiments, about 30 mg of the nalbuphine twice a day is selected to provide a substantial reduction in cough, breathlessness, or dyspnea. In some embodiments, about 90 mg of the nalbuphine once a day is selected to provide a substantial reduction in cough, breathlessness, or dyspnea. In some embodiments, about 45 mg of the nalbuphine twice a day is selected to provide a substantial reduction in cough, breathlessness, or dyspnea. In some embodiments, about 120 mg of the nalbuphine once a day is selected to provide a substantial reduction in cough, breathlessness, or dyspnea. In some embodiments, about 60 mg of the nalbuphine twice a day is selected to provide a substantial reduction in cough, breathlessness, or dyspnea. In some embodiments, about 180 mg of the nalbuphine once a day is selected to provide a substantial reduction in cough, breathlessness, or dyspnea. In some embodiments, about 90 mg of the nalbuphine twice a day is selected to provide a substantial reduction in cough, breathlessness, or dyspnea. In some embodiments, about 240 mg of the nalbuphine once a day is selected to provide a substantial reduction in cough, breathlessness, or dyspnea. In some embodiments, about 120 mg of the nalbuphine twice a day is selected to provide a substantial reduction in cough, breathlessness, or dyspnea. In some embodiments, about 360 mg of the nalbuphine once a day is selected to provide a substantial reduction in cough, breathlessness, or dyspnea. In some embodiments, about 180 mg of the nalbuphine twice a day is selected to provide a substantial reduction in cough, breathlessness, or dyspnea. In some embodiments, about 480 mg of the nalbuphine once a day is selected to provide a substantial reduction in cough, breathlessness, or dyspnea. In some embodiments, about 240 mg of the nalbuphine twice a day is selected to provide a substantial reduction in cough, breathlessness, or dyspnea.

In some embodiments, the amount of nalbuphine administered to a patient in need thereof is in the form of a pharmaceutically acceptable salt and is expressed in terms of the Equivalent Amount of Nalbuphine Free Base provided to said patient.

In some embodiments, the total daily dose of the Equivalent Amount of Nalbuphine Free Base can be at least about 14 mg a day for the treatment of cough, breathlessness, or dyspnea. In some embodiments, the total daily dose of the Equivalent Amount of Nalbuphine Free Base can be at least about 18 mg a day for the treatment of cough, breathlessness, or dyspnea. In some embodiments, the total daily dose of the Equivalent Amount of Nalbuphine Free Base can be at least about 27 mg a day for the treatment of cough, breathlessness, or dyspnea. In some embodiments, the total daily dose of the Equivalent Amount of Nalbuphine Free Base can be at least about 36 mg a day for the treatment of cough, breathlessness, or dyspnea. In some embodiments, the total daily dose of the Equivalent Amount of Nalbuphine Free Base can be at least about 54 mg a day for the treatment of cough, breathlessness, or dyspnea. In some embodiments, the total daily dose of the Equivalent Amount of Nalbuphine Free Base can be at least about 81 mg a day for the treatment of cough, breathlessness, or dyspnea. In some embodiments, the total daily dose of the Equivalent Amount of Nalbuphine Free Base can be at least about 108 mg a day for the treatment of cough, breathlessness, or dyspnea. In some embodiments, the total daily dose of the Equivalent Amount of Nalbuphine Free Base can be at least about 162 mg a day for the treatment of cough, breathlessness, or dyspnea. In some embodiments, the total daily dose of the Equivalent Amount of Nalbuphine Free Base can be at least about 216 mg a day for the treatment of cough, breathlessness, or dyspnea.

In some embodiments, the total daily dose of the Equivalent Amount of Nalbuphine Free Base can be about 14 mg a day for the treatment of cough, breathlessness, or dyspnea. In some embodiments, the total daily dose of the Equivalent Amount of Nalbuphine Free Base can be about 18 mg a day for the treatment of cough, breathlessness, or dyspnea. In some embodiments, the total daily dose of the Equivalent Amount of Nalbuphine Free Base can be about 27 mg a day for the treatment of cough, breathlessness, or dyspnea. In some embodiments, the total daily dose of the Equivalent Amount of Nalbuphine Free Base can be about 36 mg a day for the treatment of cough, breathlessness, or dyspnea. In some embodiments, the total daily dose of the Equivalent Amount of Nalbuphine Free Base can be about 54 mg a day for the treatment of cough, breathlessness, or dyspnea. In some embodiments, the total daily dose of the Equivalent Amount of Nalbuphine Free Base can be about 81 mg a day for the treatment of cough, breathlessness, or dyspnea. In some embodiments, the total daily dose of the Equivalent Amount of Nalbuphine Free Base can be about 108 mg a day for the treatment of cough, breathlessness, or dyspnea. In some embodiments, the total daily dose of the Equivalent Amount of Nalbuphine Free Base can be about 162 mg a day for the treatment of cough, breathlessness, or dyspnea. In some embodiments, the total daily dose of the Equivalent Amount of Nalbuphine Free Base can be about 216 mg a day for the treatment of cough, breathlessness, or dyspnea.

In some embodiments, about 14 mg of the Equivalent Amount of Nalbuphine Free Base once a day is selected to provide a substantial reduction in cough, breathlessness, or dyspnea. In some embodiments, about 18 mg of the Equivalent Amount of Nalbuphine Free Base once a day is selected to provide a substantial reduction in cough, breathlessness, or dyspnea. In some embodiments, about 9 mg of the Equivalent Amount of Nalbuphine Free Base twice a day is selected to provide a substantial reduction in cough, breathlessness, or dyspnea. In some embodiments, about 27 mg of the Equivalent Amount of Nalbuphine Free Base once a day is selected to provide a substantial reduction in cough, breathlessness, or dyspnea. In some embodiments, about 14 mg of the Equivalent Amount of Nalbuphine Free Base twice a day is selected to provide a substantial reduction in cough, breathlessness, or dyspnea. In some embodiments, about 54 mg of the Equivalent Amount of Nalbuphine Free Base once a day is selected to provide a substantial reduction in cough, breathlessness, or dyspnea. In some embodiments, about 27 mg of the Equivalent Amount of Nalbuphine Free Base twice a day is selected to provide a substantial reduction in cough, breathlessness, or dyspnea. In some embodiments, about 81 mg of the Equivalent Amount of Nalbuphine Free Base once a day is selected to provide a substantial reduction in cough, breathlessness, or dyspnea. In some embodiments, about 41 mg of the Equivalent Amount of Nalbuphine Free Base twice a day is selected to provide a substantial reduction in cough, breathlessness, or dyspnea. In some embodiments, about 108 mg of the Equivalent Amount of Nalbuphine Free Base one a day is selected to provide a substantial reduction in cough, breathlessness, or dyspnea. In some embodiments, about 54 mg of the Equivalent Amount of Nalbuphine Free Base twice a day is selected to provide a substantial reduction in cough, breathlessness, or dyspnea. In some embodiments, about 162 mg of the Equivalent Amount of Nalbuphine Free Base once a day is selected to provide substantial reduction in cough, breathlessness, or dyspnea. In some embodiments, about 81 mg of the Equivalent Amount of Nalbuphine Free Base twice a day is selected to provide a substantial reduction in cough, breathlessness, or dyspnea. In some embodiments, about 216 mg of the Equivalent Amount of Nalbuphine Free Base once a day is selected to provide a substantial reduction in cough, breathlessness, or dyspnea. In some embodiments, about 108 mg of the Equivalent Amount of Nalbuphine Free Base twice a day is selected to provide a substantial reduction in cough, breathlessness, or dyspnea. In some embodiments, about 327 mg of the Equivalent Amount of Nalbuphine Free Base once a day is selected to provide a substantial reduction in cough, breathlessness, or dyspnea. In some embodiments, about 162 mg of the Equivalent Amount of Nalbuphine Free Base twice a day is selected to provide a substantial reduction in cough, breathlessness, or dyspnea. In some embodiments, about 436 mg of the Equivalent Amount of Nalbuphine Free Base once a day is selected to provide a substantial reduction in cough, breathlessness, or dyspnea. In some embodiments, about 218 mg of the Equivalent Amount of Nalbuphine Free Base twice a day is selected to provide a substantial reduction in cough, breathlessness, or dyspnea.

Reduction of cough in patients with chronic cough (including IPF patients) can be determined by various methods. In some embodiments, the effectiveness of a dosage regimen can be determined by evaluation via a cough severity Numerical Rating Scale (NRS) test value, a Leicester Cough Questionnaire score, daytime cough frequency measured using cough count monitor device, 24-hour cough frequency measured using cough count monitor device, night-time cough frequency measured using cough count monitor device, cough quality of life questionnaire (CQLQ) total value, Clinical Global Impression of Change (CGIC), PROMIS Item Bank v1.0-Fatigue Short Form 7a scale, St. George's Questionnaire for the IPF population (SGRQ-I) total score, EXAcerbation of Chronic pulmonary disease Tool 6(EXACT®) version 1.1 e-diary tool total score, Evaluating Respiratory Symptoms, (E-RS™) daily diary (the E-RS™ is a 11 respiratory symptoms item derivative instrument of the EXACT® tool) cough subscale score, chest symptoms subscale score as well as the E-RS™ total score or any combination thereof. In some embodiments, the effectiveness of a dosage regimen can be determined by evaluation via a daytime cough frequency measured using cough count monitor device as a primary efficacy endpoint in association with secondary efficacy endpoints such as a Leicester Cough Questionnaire score.

Reduction of breathlessness or dyspnea (including in IPF patients) can be determined by various methods. In some embodiments, the effectiveness of a dosage regimen can be determined by evaluation via an Evaluating Respiratory Symptoms (E-RS™) breathlessness subscale score (that includes assessment of breathlessness with activity (dyspnea)), Borg dyspnea scale value total score, Borg dyspnea scale domains (sensory-perceptual, affective distress or symptom impact), numerical rating scale dyspnea value, Modified Medical Research Council Scale, PROMIS Pool v1.0 Dyspnea Emotional Response Scale, PROMIS Item Bank v1.0 Dyspnea Severity-Short Form 10a Scale, PROMIS Item Bank v1.0 Dyspnea Characteristics Scale or any combination thereof.

According to some embodiments of the present disclosure, the dosing frequency and dose amount per administration of nalbuphine are selected to provide therapeutic effects for the treatment of cough, breathlessness, or dyspnea. In some embodiments, the dosing frequency and dose amount per administration of nalbuphine are selected to provide therapeutic effects for the treatment of IPF cough, breathlessness, or dyspnea.

According to some embodiments of the present disclosure, the dosing frequency and dose amount per administration of nalbuphine are selected to provide therapeutic effects for the treatment of fatigue associated with an interstitial lung disease. In some embodiments, the interstitial lung disease is IPF. Reduction of fatigue can be determined by various methods. In some embodiments, the effectiveness of a dosage regimen can be determined by evaluation via the PROMIS Item Bank v1.0-Fatigue Short Form 7a scale.

According to some embodiments of the present disclosure, the dosing frequency and dose amount per administration of the nalbuphine are selected to provide therapeutic effects for the treatment of chronic cough. In some embodiments, the dosing frequency and dose amount per administration of nalbuphine are selected to provide therapeutic effects for the treatment of chronic cough selected from refractory chronic cough and unexplained chronic cough.

According to some embodiments of the present disclosure, the dosing frequency and dose amount per administration of the nalbuphine are selected to provide therapeutic effects for the treatment of cough hypersensitivity syndrome.

According to some embodiments of the present disclosure, the dosing frequency and dose amount per administration of the nalbuphine are selected to provide therapeutic effects for the treatment of cough, breathlessness, or dyspnea that is refractory to other treatments. In some embodiments, the dosing frequency and dose amount per administration of the nalbuphine are selected to provide therapeutic effects for the treatment of IPF cough, breathlessness, or dyspnea associated with IPF that is IPF cough, breathlessness, or dyspnea is refractory to treatment with an antitussive agent selected from gefapixant, serlopitant, and orvepitant; refractory to treatment with µ-opioid agonists; refractory to treatment with pirfenidone; refractory to treatment with nintedanib; refractory to treatment with thalidomide; or refractory to treatment with cromolyn sodium.

In some embodiments, nalbuphine or a pharmaceutically acceptable salt, solvate or ester thereof is administered on a once-a-day or twice-a-day basis for at least a week, for example, about a week, about 2 weeks, about 3 weeks, about 4 weeks, about 5 weeks, about 6 weeks, about 7 weeks, about 8 weeks, about 9 weeks, about 10 weeks, about 12 weeks, about 18 weeks, about 24 weeks, and about 50 weeks.

In some embodiments, at least about 30 mg or about 30 mg of nalbuphine or a pharmaceutically acceptable salt, solvate or ester thereof is administered on a once-a-day or twice-a-day basis for at least a week. In some embodiments, at least about 60 mg or about 60 mg of nalbuphine or a pharmaceutically acceptable salt, solvate or ester thereof is administered on a once-a-day or twice-a-day basis for at least a week. In some embodiments, at least about 90 mg or about 90 mg of nalbuphine or a pharmaceutically acceptable salt, solvate or ester thereof is administered on a once-a-day or twice-a-day basis for at least a week. In some embodiments, at least about 120 mg or about 120 mg of nalbuphine or a pharmaceutically acceptable salt, solvate or ester thereof is administered on a once-a-day or twice-a-day basis for at least a week. In some embodiments, at least about 180 mg or about 180 mg of nalbuphine or a pharmaceutically acceptable salt, solvate or ester thereof is administered on a once-a-day or twice-a-day basis for at least a week. In some embodiments, at least about 240 mg or about 240 mg of nalbuphine or a pharmaceutically acceptable salt, solvate or ester thereof is administered on a once-a-day or twice-a-day basis for at least a week. In some embodiments, at least about 360 mg or about 360 mg of nalbuphine or a pharmaceutically acceptable salt, solvate or ester thereof is administered on a once-a-day or twice-a-day basis for at least a week.

According to some embodiments, the substantial reduction in cough, breathlessness, or dyspnea provided by the methods of the present disclosure requires treatment for a specified time interval (e.g., at least one week) before the patient experiences substantial reduction of cough, breathlessness, or dyspnea (i.e., there is an induction period before the patient experiences a substantial reduction in cough, breathlessness, or dyspnea). In some embodiments, after treatment for at least one week, at least two weeks, at least three weeks, at least four weeks, at least five weeks, at least six weeks, at least seven weeks or at least eight weeks, the patient experiences a substantial reduction of cough, breathlessness, or dyspnea compared to prior to the treatment. In some embodiments, after treatment for at least one week the patient experiences a substantial reduction of cough, breathlessness, or dyspnea compared to prior to the treatment. According to this embodiment, the substantial reduction in cough, breathlessness, or dyspnea may be expressed using any of the methods described herein (for example, decline in Evaluating Respiratory Symptoms (E-RS™) cough subscale score compared to prior to the treatment, reduction in daytime cough frequency measured using cough count monitor device compared to prior to the treatment, etc.).

In some embodiments, after the treatment the patient experiences a substantial reduction of IPF symptoms (such as cough, breathlessness or dyspnea) that is characterized by at least a one-point improvement in the Clinical Global Impression of Change (CGIC) compared to prior to the treatment. In some embodiments, the reduction of IPF symptoms is characterized by an improvement in CGIC value ranging from about 1.0 to about 3.0 points, for example, about 1.0 point, about 2.0 point, about 3.0 points, compared to prior to the treatment.

In some embodiments, after the treatment the patient experiences a substantial improvement in health status related to reduction in cough frequency that is characterized by at least about a 1.0 point improvement in the total score on the patient's Leicester Cough Questionnaire score compared to prior to the treatment. In some embodiments, the improvement in health status related to reduction of cough frequency is characterized by an improvement in Leicester Cough Questionnaire score ranging from about 0.5 to about 2.0 points, for example, about 0.5 points, about 1.0 point, about 1.5 points and about 2.0 points compared to prior to the treatment. In some embodiments, the improvement in health status related to reduction of cough frequency is characterized by an improvement in any of the three Leicester Cough Questionnaire domains (physical, psychological or social) score ranging from about 0.5 to about 2.0 points, for example, about 0.5 points, about 1.0 point, about 1.5 points and about 2.0 points compared to prior to the treatment.

In some embodiments, after the treatment the patient experiences a substantial reduction of cough that is characterized by at least about a 30% reduction in daytime cough frequency measured using cough count monitor device compared to prior to the treatment. In some embodiments, the reduction of cough is characterized by a decline in daytime cough frequency ranging from 10% to about 100%, for example, about 10%, about 20%, about 30%, about 40%, about 50%, about 60%, about 70%, about 80%, about 90%, and about 100%, compared to prior to the treatment.

In some embodiments, after the treatment the patient experiences a substantial reduction of cough that is characterized by at least a one-point reduction in the cough severity Numerical Rating Scale (NRS) value compared to prior to the treatment. In some embodiments, the reduction of cough is characterized by a decline in NRS cough value ranging from about 1.0 to about 9.0 points, for example, about 1.0 point, about 2.0 point, about 3.0 points, about 4.0 points, about 5.0 points, about 6.0 points, about 7.0 points, about 8.0 points, about 9.0 points and about 10.0 points compared to prior to the treatment.

In some embodiments, after the treatment the patient experiences a substantial improvement in health-related quality of life as a result of reduction in cough frequency that is characterized by at least a 4 points improvement in cough quality of life questionnaire (CQLQ©) total value compared to prior to the treatment. In some embodiments, the improvement in health-related quality of life is characterized by an improvement in CQLQ© total value ranging from about 3.0 to about 6.0 points, for example, about 3.0 point, about 3.5 points, about 4.0 points, about 4.5 points, about 5.0 points, about 5.5 points, and about 6.0 points compared to prior to the treatment. In some embodiments, after the treatment the patient experiences a substantial improvement in health-related quality of life as a result of reduction in cough frequency that is characterized by at least a 1 points improvement in any of the six CQLQ© subscales (physical complaints, psychosocial issues, functional abilities, emotional well-being, extreme physical complaints or personal safety fears) compared to prior to the treatment. In some embodiments, the improvement in health-related quality of life is characterized by an improvement in a CQLQ© subscale score ranging from about 1.0 to about 4.0 points, for example, about 4.0 points, about 3.0 points, about 2.0 points, about 1.0 points compared to prior to the treatment.

In some embodiments, after the treatment the patient experiences a substantial reduction of cough that is characterized by at least a 5 point improvement in the patient's St. George's Questionnaire for the IPF population (SGRQ-I) total score compared to prior to the treatment. In some embodiments, the reduction of cough is characterized by an improvement in SGRQ-I total score ranging from about 4.0 to about 7.0 points, for example, about 4.0 point, about 4.5 points, about 5.0 points, about 5.5 points, about 6.0 points, about 6.5 points, and about 7.0 points compared to prior to the treatment. In some embodiments, after the treatment the patient experiences a substantial reduction of cough that is characterized by at least a 1 point improvement in any of the patient's SGRQ-I three subdomains (symptoms, activities or impacts) compared to prior to the treatment.

In some embodiments, after said treatment the patient experiences a reduction of cough that is characterized by at least a 1.0 point reduction in the Evaluating Respiratory Symptoms (E-RS™) cough subscale score compared to prior to the treatment. In some embodiments, the reduction of cough is characterized by a decline in Evaluating Respiratory Symptoms (E-RS™) cough subscale score ranging from about 1.0 to about 4.0 points, compared to prior to the treatment for example, about 1.0 point, about 2.0 points, about 3.0 points and about 4.0 points compared to prior to the treatment.

In some embodiments, after said treatment the patient experiences a reduction of cough that is characterized by at least a 1.0 point reduction in the Evaluating Respiratory Symptoms (E-RS™) chest symptoms subscale score compared to prior to the treatment. In some embodiments, the reduction of cough is characterized by a decline in Evaluating Respiratory Symptoms (E-RS™) chest symptoms subscale score ranging from about 1.0 to about 12.0 points, for example, about 1.0 point, about 2.0 points, about 3.0 points, about 4.0 points, about 5.0 points, about 6.0 points, about 7.0 points, about 8.0 points, about 9.0 points, about 10 points, about 11 points and about 12.0 points compared to prior to the treatment.

In some embodiments, after said treatment the patient experiences a reduction of breathlessness that is characterized by at least a 1.0 point reduction in the Evaluating Respiratory Symptoms (E-RS™) breathlessness subscale score compared to prior to the treatment. In some embodiments, the reduction of breathlessness is characterized by a decline in Evaluating Respiratory Symptoms (E-RS™) breathlessness subscale score ranging from about 1.0 to about 23.0 points (Bacci E D, O'Quinn S, Leidy N K, Murray L, Vernon M. Evaluation of a respiratory symptom diary for clinical studies of idiopathic pulmonary fibrosis. Respir Med. 2018 January; 134:130-138), for example, about 1.0 point, about 3.0 points, about 5.0 points, about 7.0 points, about 9.0 points, about 11.0 points, about 13.0 points, about 15.0 points, about 17.0 points, about 19 points, about 21 points and about 23.0 points compared to prior to the treatment.

In some embodiments, after said treatment the patient experiences a reduction of dyspnea that is characterized by at least a 1.0 point reduction in the Evaluating Respiratory Symptoms (E-RS™) breathlessness subscale scores connected to breathlessness related to activity compared to prior to the treatment. In some embodiments, the reduction of dyspnea is characterized by a decline in Evaluating Respiratory Symptoms (E-RS™) breathlessness subscale score connected to activity ranging from about 1.0 to about 17.0 points (Bacci E D, O'Quinn S, Leidy N K, Murray L, Vernon M. Evaluation of a respiratory symptom diary for clinical studies of idiopathic pulmonary fibrosis. Online supplement (2018). https://doi.org/10.1016/j.rmed.2017.11.011), for example, about 1.0 point, about 3.0 points, about 5.0 points, about 7.0 points, about 9.0 points, about 11.0 points, about 13.0 points, about 15.0 points, about 17.0 points compared to prior to the treatment.

In some embodiments, after said treatment the patient experiences a reduction of dyspnea that is characterized by at least a one point change in the Borg dyspnea scale value total score compared to prior to the treatment. In some embodiments, the reduction of dyspnea is characterized by a decline in Borg dyspnea scale value total score ranging from about 0.5 to about 2.0 points, for example, about 0.5 points, about 1.0 point, about 1.5 points and about 2.0 points compared to prior to the treatment.

In some embodiments, after said treatment the patient experiences a reduction of dyspnea that is characterized by at least a one point change in any of the Borg dyspnea scale domains (sensory-perceptual, affective distress or symptom impact) compared to prior to the treatment. In some embodiments, the reduction of dyspnea is characterized by a decline in Borg dyspnea scale domains (sensory-perceptual, affective distress or symptom impact) ranging from about 0.5 to about 2.0 points, for example, about 0.5 points, about 1.0 point, about 1.5 points and about 2.0 points compared to prior to the treatment.

In some embodiments, after said treatment the patient experiences a reduction of dyspnea that is characterized by at least a 3 point reduction in the numerical rating scale dyspnea value compared to prior to the treatment. In some embodiments, the reduction of dyspnea is characterized by a decline in Borg dyspnea scale domains (sensory-perceptual, affective distress or symptom impact) ranging from about 2.0 to about 5.0 points, for example, about 2.0 points, about 2.5 points, about 3.0 point, about 3.5 points, about 4.0 points, about 4.5 points and about 5.0 points compared to prior to the treatment In some embodiments, after said treatment the patient experiences a reduction of dyspnea that is characterized by at least a one category change in the Modified Medical Research Council Scale compared to prior to the treatment. In some embodiments, the reduction of dyspnea is characterized by an improvement in Modified Medical Research Council Scale ranging from at least one category to about three categories, for example, about one category, about two categories, and about three categories compared to prior to the treatment.

In some embodiments, after said treatment the patient experiences a reduction of dyspnea that is characterized by at least a one category change in at least one of the 7 questions of the PROMIS Pool v1.0 Dyspnea Emotional Response Scale compared to prior to the treatment. In some embodiments, the reduction of dyspnea is characterized by an improvement in at least one of the 7 questions of the PROMIS Pool v1.0 Dyspnea Emotional Response Scale ranging from at least one category to about three categories, for example, about one category, about two categories, and about three categories compared to prior to the treatment.

In some embodiments, after said treatment the patient experiences a reduction of dyspnea that is characterized by at least a one category change in at least one of the 10 questions of the PROMIS Item Bank v1.0 Dyspnea Severity-Short Form 10a Scale compared to prior to the treatment. In some embodiments, the reduction of dyspnea is characterized by an improvement in at least one of the 10 questions of the PROMIS Item Bank v1.0 Dyspnea Severity-Short Form 10a Scale ranging from at least one category to about three categories, for example, about one category, about two categories, and about three categories compared to prior to the treatment.

In some embodiments, after said treatment the patient experiences a reduction of dyspnea that is characterized by at least a one category change in at least one of the 4 items or a one category change in the question "I have been short of breath" of the PROMIS Item Bank v1.0 Dyspnea Characteristics Scale compared to prior to the treatment. In some embodiments, the reduction of dyspnea is characterized by an improvement in at least one of the 4 items and/or the question "I have been short of breath" of the PROMIS Item Bank v1.0 Dyspnea Characteristics Scale ranging from at least one category to about three categories, for example, about one category, about two categories, and about three categories compared to prior to the treatment.

In some embodiments, after said treatment the patient experiences a reduction of fatigue that is characterized by at least a one category change in at least one of the 7 questions of the PROMIS Item Bank v1.0 Fatigue Short Form 7a Scale. In some embodiments, the reduction of fatigue is characterized by an improvement in at least one of the 7 questions of the PROMIS Item Bank v1.0 Fatigue Short Form 7a Scale ranging from at least one category to about three categories, for example, about one category, about two categories, about three categories, about four categories, about five categories, about six categories, and about seven categories compared to prior to the treatment.

In some embodiments, after said treatment the patient experiences a substantial reduction in the rate of pulmonary fibrosis progression compared to prior to said treating as quantified by objective measures (chest x-ray, pulmonary function tests, etc.).

In some embodiments, after said treatment the patient experiences a substantial reduction in the hospitalization rate based on improvement in the dyspnea and cough status.

In some embodiments, after said treatment the patient experiences a substantial reduction in morbidity and mortality as a result of the lessening incidence of acute exacerbations of IPF (AE-IPF) related to deterioration of lung function and/or lessening of breathing difficulties secondary to an interruption in the "dyspnea cycle" positive feedback loop of progressively more frequent episodes of dyspnea of increasing intensity.

In some embodiments, the daily dose of the nalbuphine is in a once or twice daily dose, and then titrated upward until the patient experiences satisfactory relief from the cough, breathlessness, or dyspnea. The daily dose can be titrated in increments ranging from about 5 mg to about 360 mg (e.g., about 15 mg, about 30 mg or about 60 mg). The daily dose can be titrated in one or more steps. The daily dosage can be titrated by increasing a single daily dosage, or each dose of a twice-daily dosing regimen. The amount a dosage is stepped, where there are multiple titration steps, can be the same, or can be different.

In some embodiments, the titration may be initiated with about 15 mg, about 30 mg or about 60 mg of the nalbuphine once or twice daily. In some embodiments, doses can be adjusted in 30 mg increments every 1 to 4 days. Patients can self-titrate to effect over from about 7 days to about 30 days (for example, from about 12 days to about 20 days) to a dose that provides adequate relief from cough, breathlessness, or dyspnea and minimizes adverse reactions. In some embodiments, the titration is conducted for at least about one week, 2 weeks, 3 weeks, 4 weeks or 5 weeks until a steady state is achieved in the patient.

In some embodiments, patients can be provided initially with 15 mg, 30 mg or 60 mg tablets to self-titrate to effect up to about 60 mg, about 90 mg, about 120 mg, about 180 mg, about 240 mg, about 360 mg, or about 480 mg once or twice a day. In some embodiments, the titration dose is started with about 15 mg or about 30 mg, and then gradually increased to about 90 mg or 180 mg twice a day, e.g., for patients with IPF cough, breathlessness, or dyspnea. In some embodiments, the titration dose is started with about 15 mg or about 30 mg, and then gradually increased to about 180 mg or 360 mg once a day, e.g., for patients with IPF cough, breathlessness, or dyspnea.

In some embodiments, the nalbuphine titration is conducted for seventeen days according to the dose schedule provided in the following table (expressed as Equivalent Amount of Nalbuphine Free Base):

| Day | AM dosage (mg) | PM dosage (mg) |
|---|---|---|
| Day 1 | 0 | 27 |
| Day 2 | 0 | 27 |
| Day 3 | 27 | 27 |
| Day 4 | 27 | 27 |
| Day 5 | 27 | 54 |
| Day 6 | 54 | 54 |
| Day 7 | 54 | 54 |
| Day 8 | 54 | 54 |
| Day 9 | 54 | 108 |
| Day 10 | 90 | 108 |
| Day 11 | 90 | 108 |
| Day 12 | 108 | 108 |
| Day 13 | 108 | 108 |
| Day 14 | 108 | 108 |
| Day 15 | 108 | 108 |
| Day 16 | 108 | 162 |
| Day 17 | 162 | 162 |

In some embodiments, the nalbuphine titration is conducted for two weeks according to the dose schedule provided in the following table (expressed as Equivalent Amount of Nalbuphine Free Base):

| Day | AM dosage (mg) | PM dosage (mg) |
|---|---|---|
| Day 1 | 0 | 27 |
| Day 2 | 0 | 27 |
| Day 3 | 27 | 27 |
| Day 4 | 27 | 27 |
| Day 5 | 27 | 54 |
| Day 6 | 54 | 54 |
| Day 7 | 54 | 54 |
| Day 8 | 54 | 90 |
| Day 9 | 90 | 90 |
| Day 10 | 90 | 90 |
| Day 11 | 90 | 108 |
| Day 12 | 108 | 108 |
| Day 13 | 108 | 108 |
| Day 14 | 108 | 162 |

In some embodiments, the nalbuphine titration is conducted for two weeks according to the dose schedule provided in the following table (expressed as Equivalent Amount of Nalbuphine Free Base):

| Day | AM dosage (mg) | PM dosage (mg) |
|---|---|---|
| Day 1 | 0 | 27 |
| Day 2 | 0 | 27 |
| Day 3 | 27 | 27 |
| Day 4 | 27 | 27 |
| Day 5 | 27 | 54 |
| Day 6 | 54 | 54 |
| Day 7 | 54 | 54 |
| Day 8 | 54 | 90 |
| Day 9 | 90 | 90 |
| Day 10 | 90 | 90 |
| Day 11 | 90 | 108 |
| Day 12 | 108 | 108 |
| Day 13 | 108 | 108 |
| Day 14 | 108 | 108 |

According to some embodiments of the present disclosure, the methods of the present disclosure provide therapeutically effective blood plasma levels of nalbuphine for treating patients with IPF cough, breathlessness, or dyspnea. Blood plasma levels of nalbuphine may be expressed using pharmacokinetic parameters that are known to those skilled in the art, such as steady state plasma levels, AUC, Cmax and Cmin. Blood plasma levels of nalbuphine are described in U.S. Publication Nos. 2014/0171459, 2014/0350042, 2015/0359789, and 2017/0216277, which are hereby incorporated by reference in their entirety.

In some embodiments, the present methods provide steady state plasma levels of nalbuphine that correlate to one or more statistically significant therapeutic effects. In some embodiments, the therapeutically effective steady state plasma levels of nalbuphine provided by the methods of the present disclosure range from about 10 ng/mL to about 80 ng/mL, including about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL and about 80 ng/mL, including all ranges there between. In some embodiments, the therapeutically effective steady state plasma levels of nalbuphine is provided by administering a daily dose of nalbuphine or a pharmaceutically acceptable salt or ester is about 360 mg. In further embodiments, the therapeutically effective steady state plasma levels of nalbuphine is provided by administering about 180 mg of nalbuphine or a pharmaceutically acceptable salt or ester thereof twice a day.

In some embodiments, the present methods provide mean steady state $AUC_{0-24h}$ (expressed in terms of ng*hr/mL) levels of nalbuphine that correlate to one or more statistically significant therapeutic effects. In some embodiments, the therapeutically effective mean steady state $AUC_{0-24h}$ levels of nalbuphine provided by the methods of the present disclosure range from about 200 ng*hr/mL to about 1600 ng*hr/mL, including about 300 ng*hr/mL, about 400 ng*hr/mL, about 500 ng*hr/mL, about 600 ng*hr/mL, about 700 ng*hr/mL, about 800 ng*hr/mL, about 900 ng*hr/mL, about 1000 ng*hr/mL, about 1100 ng*hr/mL, about 1200 ng*hr/mL, about 1300 ng*hr/mL, about 1400 ng*hr/mL, and about 1500 ng*hr/mL, including all ranges there between. In some embodiments, the therapeutically effective mean steady state $AUC_{0-24h}$ levels of nalbuphine is provided by administering a daily dose of nalbuphine or a pharmaceutically acceptable salt or ester is about 360 mg. In further embodiments, the therapeutically effective mean steady state $AUC_{0-24h}$ levels of nalbuphine is provided by administering about 180 mg of nalbuphine or a pharmaceutically acceptable salt or ester thereof twice a day.

In some embodiments, the nalbuphine, and the metabolites include glucuronides (most likely on the phenol and cyclohexane rings), two hydroxylated nalbuphine metabolites (on the cyclobutane ring) and three ketones (hydroxylation of the cyclobutane ring, followed by oxidation to a carbonyl or followed by ring opening of the cyclobutane ring). In some embodiments, the nalbuphine metabolites include nalbuphine 3-glucuronide or 6-glucuronide. In some other embodiments, the nalbuphine metabolites include triple hydroxylated nalbuphine, mono-hydroxylated nalbuphine, or mono-glucuronidated nalbuphine or a combination thereof. In some embodiments, the one or more metabolites of the nalbuphine do not have detectable antitussive, anti-breathlessness or anti-dyspneic activity. In other embodiments, one or more of the metabolites of nalbuphine exhibit anti-antitussive, anti-breathlessness or anti-dyspneic activity.

In embodiments wherein one or more metabolites of nalbuphine exhibit antitussive, anti-breathlessness or anti-dyspneic activity, the dosing regimen of the nalbuphine may be adjusted and/or titrated as described hereinabove depending on the clearance rate of the one or more metabolites exhibiting antitussive, anti-breathlessness or anti-dyspneic activity. Such dosage adjustment and/or titration of the dosage of the nalbuphine can be performed to prevent accumulation of either the nalbuphine and/or one or more metabolites, which can also exhibit antitussive, anti-breathlessness or anti-dyspneic activity, to avoid toxicity effects in a patient treated with nalbuphine.

In some embodiments, the nalbuphine is completely metabolized (e.g., about 100% metabolized). In other embodiments, the nalbuphine is not completely metabolized (e.g., less than about 100% metabolized). For example, in some embodiments, the nalbuphine is about 100% metabolized, about 95% metabolized, about 90% metabolized, about 85% metabolized, about 80% metabolized, about 75% metabolized, about 70% metabolized, about 65% metabolized, about 60% metabolized, about 55% metabolized, about 50% metabolized, about 45% metabolized, about 40% metabolized, about 35% metabolized, about 25% metabolized, about 20% metabolized, about 15% metabolized, about 10% metabolized, about 5% metabolized, about 1% metabolized, or about 0% metabolized. In some embodiments, the amount of dialyzable agent can be measured or monitored by the level of accumulation, e.g., blood plasma level of the nalbuphine or one or more of its metabolites.

The embodiments described herein should be understood to be illustrative of the present disclosure, and should not be construed as limiting. On the contrary, the present disclosure embraces alternatives and equivalents thereof, as embodied by the appended claims. Each reference disclosed herein is incorporated by reference herein in its entirety.

The following non-limiting examples illustrate various aspects of the present invention.

EXAMPLES

Example 1

A 30 mg, 60 mg or 180 mg extended release (ER) nalbuphine tablet was prepared as follows: Nalbuphine HCl, mannitol, xanthan gum, locust bean gum and calcium sulfate dihydrate were added to a high shear mixer and dried mix at low speed. A granulating solution (water for injection or purified water) was introduced into the mixer at low speed. The wet granulation was granulated at high speed and dried in a fluid bed processor. The dried granules were milled and sized using a conventional mill. The milled granulation was transferred into a diffusion (tumble) mixer. Hydroxypropylcellulose and, when applicable, fumaric acid (180 mg formulations only) were added to the diffusion mixer and blended. Thereafter, magnesium stearate was added to the diffusion mixer and blended. The final blend was compressed using a rotary tablet press. Tablets may be coated with a non-functional Opadry white coating.

TABLE 1

30 mg, 60 mg, 120 mg and 180 mg Extended Release Nalbuphine Tablet

| Ingredient | mg/tablet |
| --- | --- |
| Nalbuphine HCl | 29.8 |
| Mannitol | 107.3 |
| Hydroxypropylcellulose | 34.7 |
| Locust bean gum | 32.2 |
| Xanthan gum | 21.4 |
| Calcium sulfate dehydrate | 17.9 |
| Magnesium stearate | 1.9 |
| Water for injection or Purified water | QS |
| Total: | 245.1 |

| Ingredient | mg/tablet |
| --- | --- |
| Nalbuphine HCl | 59.5 |
| Mannitol | 71.5 |
| Hydroxypropylcellulose | 29.8 |
| Locust bean gum | 21.4 |
| Xanthan gum | 14.3 |
| Calcium sulfate dehydrate | 11.9 |
| Magnesium stearate | 1.6 |
| Water for injection or Purified water | QS |
| Total: | 210.0 |

| Ingredient | mg/tablet |
| --- | --- |
| Nalbuphine HCl | 119.0 |
| Mannitol | 143.0 |
| Hydroxypropylcellulose | 59.6 |
| Locust bean gum | 42.9 |
| Xanthan gum | 28.6 |
| Calcium sulfate dehydrate | 23.8 |
| Magnesium stearate | 3.2 |
| Water for injection or Purified water | QS |
| Total: | 432.6 |

| Ingredient | mg/tablet |
| --- | --- |
| Nalbuphine HCl | 178.5 |
| Mannitol | 160.8 |
| Hydroxypropylcellulose | 59.6 |
| Locust bean gum | 48.2 |

TABLE 1-continued

| | |
|---|---|
| Xanthan gum | 32.2 |
| Calcium sulfate dehydrate | 26.8 |
| Magnesium stearate | 4.0 |
| Fumaric acid | 24.8 |
| Water for injection or Purified water | QS |
| Total: | 246.9 |

The tablets were coated with a non-functional coat (Opadry II White).

TABLE 2

Nalbuphine HCl ER Tablets, 30 mg, 60 mg, or 180 mg Compositions

| Component | Tablet (mg/tablet) |
|---|---|
| Nalbuphine HCl | 30.0 |
| Mannitol | 108.0 |
| Hydroxypropylcellulose | 35.0 |
| Locust bean gum | 32.4 |
| Xanthan gum | 21.6 |
| Calcium sulfate dihydrate | 18.0 |
| Magnesium stearate | 1.9 |
| Opadry II White | 7.4 |
| Sterile water for irrigation | QS |
| Total | 254.3 |

| Component | Tablet (mg/tablet) |
|---|---|
| Nalbuphine HCl | 60.0 |
| Mannitol | 72.0 |
| Hydroxypropylcellulose | 30.0 |
| Locust bean gum | 21.6 |
| Xanthan gum | 14.4 |
| Calcium sulfate dihydrate | 12.0 |
| Magnesium stearate | 1.6 |
| Opadry II White | 6.355 |
| Sterile water for irrigation | QS |
| Total | 218 |

| Component | Tablet (mg/tablet) |
|---|---|
| Nalbuphine HCl | 180 |
| Mannitol | 160.8 |
| Hydroxypropylcellulose | 59.6 |
| Locust bean gum | 48.2 |
| Fumaric acid | 24.8 |
| Xanthan gum | 32.2 |
| Calcium sulfate dihydrate | 26.8 |
| Magnesium stearate | 4.0 |
| Sterile water for irrigation | QS |
| Total | 534.9 |

Example 2

A double-blind, randomized, placebo-controlled, 2-period crossover safety and efficacy study in Idiopathic Pulmonary Fibrosis subjects with nalbuphine HCl ER tablets for the treatment of cough, breathlessness and dyspnea will be undertaken according to the following protocol.

The study consists of two 3-week treatment periods separated by a washout period of 2 weeks (FIG. 1). In the first treatment period, patients are randomized in a 1:1 ratio to nalbuphine ER tablets to a target dose of 162 mg twice daily (BID) (Equivalent Amount of Nalbuphine Free Base) or placebo tablets BID.

The primary objectives are evaluating the effects of nalbuphine HCl ER tablets on (1) the percent change in the daytime cough frequency and (2) as well as safety and tolerability. Daytime is defined as period of time the subject is awake in the 24 hours after the digital cough monitor is applied for use. Assessments are done using objective digital cough monitoring.

Participants

To be eligible, patients must suffer from idiopathic pulmonary fibrosis, and patients must have chronic cough (>8 weeks).

Inclusion Criteria

Patients are required to meet all of the following criteria to be eligible for inclusion in the study:

Diagnosis of "definite" or "probable" IPF based on ATS/ERS/JRS/ALAT criteria (see Raghu G, et al; American Thoracic Society, European Respiratory Society, Japanese Respiratory Society, and Latin American Thoracic Society. Diagnosis of Idiopathic Pulmonary Fibrosis. An Official ATS/ERS/JRS/ALAT Clinical Practice Guideline. Am J Respir Crit Care Med. 2018 Sep. 1; 198(5).).

Forced vital capacity (FVC)>40% predicted of normal.

Diffusing capacity of the lung for carbon monoxide corrected for hemoglobin [DLCO] >25% predicted of normal.

Chronic cough >8 weeks.

Adequate swallow reflex as assessed by the ability to sip 3 fluid oz (or 89 ml) of water without coughing or choking.

Daytime cough severity score ≥4 on Cough Severity Numerical Rating Scale at screening.

Males or females age 18 years and older at the time of consent.

Females of childbearing potential must use an acceptable method of birth control (if sexually active).

All females of childbearing potential must have a negative pregnancy test at the screening and baseline visits.

For the purpose of this study, all females are considered to be of childbearing potential unless they are postmenopausal (i.e., at least 1 year since last menses and age >50 years) or surgically sterile (i.e., tubal ligation, hysterectomy, and/or bilateral oophorectomy).

Sexually active female subjects of childbearing potential are required to use 1 barrier method (e.g., condom, cervical cap, or diaphragm) of contraception in addition to 1 other method (e.g., intrauterine device in place for at least 1-month, stable hormonal contraception for at least 3 months, Essure procedure, or spermicide). For female subjects using a barrier method plus spermicide, that method must be used for at least 14 days prior to Screening.

Female subjects who are abstinent may participate in the study; however, they must be counseled on the requirement to use appropriate contraception should they become sexually active. This counseling should occur at each study visit and must be documented in source records.

Willing and able to understand and provide written informed consent.

Willing and able to comply with study requirements and restrictions.

Agree to the confidential use and storage of all data and use of all anonymized data for publication including scientific publication.

Exclusion Criteria

If a patient meets any of the following criteria, he or she is not eligible:

The following conditions are excluded:
  a) Interstitial lung disease (ILD) known to be caused by domestic and occupational environmental exposures
  b) Interstitial lung disease (ILD) known to be caused by connective tissue disease.

c) Interstitial lung disease (ILD) known to be caused by drug related toxicity.
Currently on continuous oxygen therapy.
Major psychiatric disorder, which in the opinion of the Investigator, could interfere with the assessment of anti-cough efficacy and/or safety events during the study or with the ability of the subject to cooperate with study requirements.
Serum bilirubin >1.5×upper limit of normal range at screening unless explained by a clinical diagnosis of Gilbert's syndrome.
Serum hepatic alanine aminotransferase or aspartate aminotransferase enzymes >100 U/L at screening.
Estimated glomerular filtration rate ≤44 mL/min/1.73 m$^2$ at screening.
Upper or lower respiratory tract infection within 4 weeks of screening.
Significant medical condition or other factors that may interfere with the subject's ability to successfully complete the study.
History of substance abuse that, as determined by the Investigator, may interfere with the conduct of the study.
Known intolerance or hypersensitivity/drug allergy to nalbuphine or vehicle components.
Pregnant or lactating female subject.
Concurrent enrollment in an ongoing clinical trial or anticipated enrollment in a concurrent clinical trial.
Clinical diagnosis of sleep apnea and/or use of continuous positive airway pressure (CPAP).
History of clinically significant head injury in past 1 month.
Clinical diagnosis of aspiration pneumonitis.
Clinical history of opiate withdrawal symptoms following use of opiates.
Documented or clinically suspected hypercapnia (pCO2 >6.0 kPa).
Medication-Related Exclusions:
Known intolerance (gastrointestinal, central nervous system symptoms) or hypersensitivity/drug allergy to opioids.
Exposure to any investigational medication, including placebo, within 4 weeks.
Potential subjects cannot have received opiates, including opiate-containing anti-cough agents, within 14 days prior to the screening period. Subjects are prohibited from using opioids, including naltrexone, for the duration of the study.
Potential subjects cannot currently be receiving benzodiazepines or other CNS Depressant Class Drugs that when used concomitantly with opioids are known to have the potential to cause added pharmacologic effects of depressing CNS activity.
Potential subjects cannot currently be receiving medications that affect serotonergic neurotransmission and that when used concomitantly with opioids can cause serotonin syndrome.
Alcohol consumption is prohibited for the duration of study treatment (due to the potential cause of added pharmacologic effects of CNS depression when used concomitantly with opioids.
Change of IPF-related drug treatment regimen within 8 weeks of screening.
Cardiac-Related Exclusions
Subjects with a history of congestive heart failure of Class 2 or higher as graded using the New York Heart Association (NYHA) classification.
Subjects with a history of angina pectoris Grade 2 or higher as graded using the Canadian Cardiovascular Society (CCS) grading scale.
History of ventricular tachycardia, Torsade de Pointes, or family history of sudden death.
Myocardial infarction or acute coronary syndrome within the previous 3 months, as reported by the subject.
Serum potassium below the laboratory lower limit of normal.
QTcF interval >450 ms on screening ECG.
Heart rate <45 bpm on any screening measurement. Subjects with a resting heart rate of <45 bpm will have it repeated once after 5 minutes in the supine position, and if it remains <45 bpm during the repeat, they will be considered a screen failure.
Use of a medication having a "known risk" of Torsade de Pointes (categorized as "KR" on the Credible Meds® website) is not permitted at entry or during the study. Medications associated with a potential risk of QT prolongation, but not clearly associated with Torsade de Pointes, are permitted at study entry if the following criteria are met:
Subject has been given medication at stable doses for a full 4 weeks prior to screening. Medication dose will not be increased after screening, or during the study, and it is anticipated that the subject will receive the medication for the entirety of the study. QTcF at Screening is ≤450 ms.
Outcomes
The primary endpoint is the percent change in daytime cough frequency (coughs per hour) from baseline as assessed by objective digital cough monitoring at Day 22 by treatment.
Secondary endpoints include:
Relative change in daytime cough frequency (coughs per hour) from baseline at Day 9 (dose: 54 mg BID), Day 16 (dose: 108 mg BID), and Day 22 (dose: 162 mg BID) by treatment.
Relative change in 24-hour (combined daytime and nighttime) cough frequency (coughs per hour) from baseline at Day 9 (dose: 54 mg BID), Day 16 (dose: 108 mg BID), and Day 22 (dose: 162 mg BID) by treatment.
Relative change in nighttime cough frequency (coughs per hour) from baseline at Day 9 (dose: 54 mg BID), Day 16 (dose: 108 mg BID), and Day 22 (dose: 162 mg BID) by treatment.
Percentage of E-RS diary cough subscale (E-RS diary question number 2) responders, with response defined as at least a one category improvement from baseline, at Days 9, 16, and 22 by treatment.
Mean change in the Cough Severity Numerical Rating Scale at Days 8, 15, and 21 by treatment.
Mean change in the E-RS diary breathlessness subscale (E-RS diary questions 7, 8, 9, 10, and 11) from baseline at Days 9, 16, and 22 by treatment.
Mean change in the 14-item EXACT v1.1 e-diary tool total score from baseline at Days 9, 16, and 22 by treatment.
Mean change in the PROMIS Item Bank v1.0 Fatigue Short Form 7a scale from baseline at Days 8, 15, and 21 by treatment.
Mean change in the CGI-C over time measured at Days 8, 15, and 21 by treatment.
Statistical Methods
Sample Size and Power
The planned sample size of approximately 44 subjects (22 per sequence) gives 80% power to detect 40% change in daytime cough frequency at the 5% statistical significance level (two-sided).

Primary efficacy analysis is based completers population, which consists of all subjects who received both study treatments and completed both treatment periods in the study.

Efficacy

Percent change in daytime cough frequency (coughs per hour) are analyzed using a mixed-effects model with sequence, treatment, and time (Days 9, 16, and 22) as fixed effects, the baseline value as a covariate, site as a random effect, and subject as a random repeated effect. There will be no imputation for dropouts or missing data for assessments not completed at study visits.

Safety

The incidence of adverse events is summarized through the presentation of proportions by Medical Dictionary for Regulatory Activities (MedDRA) body system classification and preferred term. Vital signs and laboratory data will be summarized using descriptive statistics. The extent and duration of use of prohibited or restricted medications are similarly summarized using descriptive statistics. No formal statistical analysis are performed on safety outcomes; inferences, when present, are derived through clinical review and interpretation.

Adverse events of special interest (AESI) that code to the most relevant abuse-related MedDRA preferred terms are tabulated and descriptive narratives are written. Additional adverse events that are considered "possibly related to abuse potential" are tabulated separately.

Electrocardiograms are read centrally by specially trained staff, with real-time feedback to clinical sites regarding any findings relevant to safety. Once the database is complete, ECG data (e.g., heart rate, PR, QTcF intervals) are presented in listings by subject and summarized by collection date and time. A complete ECG assessment is documented in a separate report from the central ECG laboratory.

Pharmacokinetics

Investigational product plasma concentration data (nalbuphine and metabolites) are listed by collection time, as applicable.

When data allow, two additional sets of analyses are conducted and provided in separate reports: 1) Analysis and reporting of concentration results; and 2) pharmacokinetic-pharmacodynamic (PK-PD) analyses to describe the exposure-response relationships between nalbuphine plasma concentrations and efficacy parameters.

Additional PK-PD analyses are conducted to include safety and/or tolerability parameters, as appropriate.

Interventions

The study consists of two treatment periods of 22 days separated by a washout period of 2 weeks (FIG. 1).

During Treatment Period 1, eligible subjects are randomized (1:1) to one of the following treatment arms:

Arm 1: Active NAL ER tablets followed by crossover Placebo tablets in Treatment Period 2

Arm 2: Placebo tablets followed by crossover NAL ER tablets in Treatment Period 2.

Subjects on NAL ER are titrated from 27 mg QD to 54 mg BID over treatment days 1-6 period and then maintained at 54 mg BID for treatment days 6-8. Doses are subsequently escalated to 108 mg BID over treatment days 9-10 and then maintained at 108 mg BID for treatment days 10-15. Doses are subsequently escalated to 162 mg BID over treatment days 16-17 and then maintained at 162 mg BID for treatment days 17-21. On treatment day 22, subjects on NAL ER will receive an AM dose of 162 mg.

After a washout period of 2 weeks, the subjects receive the second treatment (NAL ER or Placebo) over a 3-week period drug following the same protocol (FIG. 1). Subjects are discharged at the end of the second treatment. The total duration of the study is up to 11 weeks.

Study visits include screening to determine eligibility, and for each treatment period: visits at Day −1 for baseline assessments, at Days 8, 15, and 21 during treatment, and a follow-up at the end of the 2-week washout period. At study visits during each treatment period, subjects have blood drawn for safety analysis and PK analysis of nalbuphine plasma concentration. Subjects complete questionnaires for efficacy evaluations and undergo safety evaluations including an ECG. At the baseline visit and visits during each treatment period, site staff place an electronic cough monitor on the subject, which is worn until the evening of the following day in order to obtain at least a full 24-hour recording period of cough frequency. At the end of each recording session, the monitor is removed at home by the subject prior to bedtime. Subjects complete a daily e-diary prior to bedtime.

Subjects who discontinue investigational product, for reasons other than withdrawal of consent, are considered to have prematurely discontinued treatment and are asked to complete the premature discontinuation and 2-week off-treatment safety follow-up evaluations.

Results

The IPF patients in the NAL ER treated group exhibit a reduction in one or more of cough, breathlessness or dyspnea symptoms as indicated by the clinical endpoints described herein.

TREV-008/06US 318488-2235

EMBODIMENTS

1. A method of treating idiopathic pulmonary fibrosis (IPF) cough, breathlessness or dyspnea comprising administering an effective amount of nalbuphine or a pharmaceutically acceptable salt or ester thereof to a patient in need of such treatment.
2. The method of embodiment 1, wherein prior to said treatment the patient's daytime cough severity is at least 4 on the Cough Severity Numerical Rating scale.
3. The method of embodiment 1, wherein prior to said treatment the patient's daytime average cough count is at least 15 per hour measured using a cough count monitor device.
4. The method of embodiment 1, wherein the IPF cough is chronic cough.
5. The method of embodiment 1, wherein the IPF cough is refractory chronic cough.
6. The method of embodiment 1, wherein the IPF cough is refractory to treatment with an antitussive agent selected from gefapixant, serlopitant, and orvepitant.
7. The method of embodiment 1, wherein the IPF cough, breathlessness, or dyspnea is refractory to treatment with μ-opioid agonists.
8. The method of embodiment 1, wherein the IPF cough, breathlessness, or dyspnea is refractory to treatment with pirfenidone.
9. The method of embodiment 1, wherein the IPF cough, breathlessness, or dyspnea is refractory to treatment with nintedanib.
10. The method of embodiment 1, wherein the IPF cough, breathlessness, or dyspnea is refractory to treatment with thalidomide.
11. The method of embodiment 1, wherein the IPF cough, breathlessness, or dyspnea is refractory to treatment with cromolyn sodium.

12. The method of embodiment 1, wherein the patient is also treated for a disease selected from the group consisting of pulmonary hypertension, obstructive sleep apnea, lung cancer, COPD/emphysema, ischemic heart disease and GERD.
13. A method of treating chronic cough comprising administering an effective amount of nalbuphine or a pharmaceutically acceptable salt or ester thereof to a patient in need of such treatment.
14. The method of embodiment 13, wherein the chronic cough is selected from refractory chronic cough, unexplained chronic cough, unexplained and refractory chronic cough.
15. The method of embodiment 14, wherein the chronic cough is refractory to treatment with tramadol.
16. The method of any one of embodiments 13-15, wherein the patient in need of a treatment of chronic cough is a patient without a lung disease.
17. The method of any one of embodiments 13-15, wherein the patient in need of a treatment of chronic cough is a patient with a lung disease.
18. The method of embodiment 17, wherein the lung disease is an interstitial lung disease.
19. The method of embodiment 18, wherein the interstitial lung disease is selected from the group consisting of hypersensitivity pneumonitis, sarcoidosis, asbestosis, bronchiolitis obliterans, histiocytosis X, chronic eosinophilic pneumonia, collagen vascular disease, granulomatous vasculitis, Goodpasture's syndrome and, pulmonary alveolar proteinosis 20. The method of embodiment 17, wherein the lung disease is a chronic obstructive pulmonary lung disease (COPD).
21. The method of embodiment 20, wherein the COPD is associated with a condition selected from the group consisting of emphysema, chronic bronchitis and Alpha-1-antitrypsin (AAt) deficiency.
22. The method of embodiment 20, wherein the COPD is associated with an irritant selected from the group consisting of cigarette smoke, secondhand smoke, pipe smoke, air pollution and workplace exposure to dust, smoke or fumes.
23. A method of treating cough hypersensitivity disorder comprising administering an effective amount of nalbuphine or a pharmaceutically acceptable salt or ester thereof to a patient in need of such treatment.
24. The method of any one of embodiments 1-23, wherein about 14 mg of the Equivalent Amount of Nalbuphine Free Base is administered once a day.
25. The method of any one of embodiments 1-23, wherein about 14 mg of the Equivalent Amount of Nalbuphine Free Base is administered twice a day.
26. The method of any one of embodiments 1-23, wherein about 27 mg of the Equivalent Amount of Nalbuphine Free Base is administered once a day.
27. The method of any one of embodiments 1-23, wherein about 27 mg of the Equivalent Amount of Nalbuphine Free Base is administered twice a day.
28. The method of any one of embodiments 1-23, wherein about 54 mg of the Equivalent Amount of Nalbuphine Free Base is administered once a day.
29. The method of any one of embodiments 1-23, wherein about 54 mg of the Equivalent Amount of Nalbuphine Free Base is administered twice a day.
30. The method of any one of embodiments 1-23, wherein about 81 mg of the Equivalent Amount of Nalbuphine Free Base is administered once a day.
31. The method of any one of embodiments 1-23, wherein about 81 mg of the Equivalent Amount of Nalbuphine Free Base is administered twice a day.
32. The method of any one of embodiments 1-23, wherein about 108 mg of the Equivalent Amount of Nalbuphine Free Base is administered once a day.
33. The method of any one of embodiments 1-23, wherein about 108 mg of the Equivalent Amount of Nalbuphine Free Base is administered twice a day.
34. The method of any one of embodiments 1-23, wherein about 162 mg of the Equivalent Amount of Nalbuphine Free Base is administered once a day.
35. The method of any one of embodiments 1-23, wherein about 162 mg of the Equivalent Amount of Nalbuphine Free Base thereof is administered twice a day.
36. The method of any one of embodiments 1-23, wherein about 324 mg of the Equivalent Amount of Nalbuphine Free Base is administered once a day.
37. The method of any one of embodiments 1-36, wherein said administering is for about 8 weeks, 10 weeks, 12 weeks, 24 weeks or 50 weeks.
38. The method of any one of embodiments 1-36, wherein said administering is for at least about 1 week.
39. The method of any one of embodiments 1-38, further comprising titrating the dose of nalbuphine or a pharmaceutically acceptable salt or ester thereof for at least one week until a steady state is achieved in the patient.
40. The method of any one of embodiments 1-38, further comprising titrating the dose of nalbuphine or a pharmaceutically acceptable salt or ester thereof for about 2 weeks until a steady state is achieved in the patient.
41. The method of any one of embodiments 1-38, further comprising titrating the dose of nalbuphine or a pharmaceutically acceptable salt or ester thereof for about 7 to 30 days until a steady state is achieved in the patient.
42. The method of any one of embodiments 1-38, further comprising titrating the dose of the nalbuphine or a pharmaceutically acceptable salt or ester thereof for about 14 to 20 days until a steady state is achieved in the patient.
43. The method of embodiment 39, wherein said titrating comprises administering ascending doses of nalbuphine or a pharmaceutically acceptable salt or ester thereof until a steady state is achieved in the patient.
44. The method of embodiment 39, wherein said titrating comprises administering ascending doses of nalbuphine or a pharmaceutically acceptable salt or ester thereof until an effective amount of 27 mg or 324 mg is achieved in the patient.
45. The method of embodiment 39, wherein said titrating further comprises administering an initial dose of about 27 mg once or twice a day.
46. The method of embodiment 39, wherein said titrating comprises administering nalbuphine or a pharmaceutically acceptable salt or ester thereof in increments ranging from about 13 mg to about 54 mg.
47. The method of embodiment 39, wherein said titrating comprises administering nalbuphine according to the dose schedule provided in the following table (expressed as Equivalent Amount of Nalbuphine Free Base):

| Day | AM dosage (mg) | PM dosage (mg) |
| --- | --- | --- |
| Day 1 | 0 | 27 |
| Day 2 | 0 | 27 |
| Day 3 | 27 | 27 |
| Day 4 | 27 | 27 |

-continued

| Day | AM dosage (mg) | PM dosage (mg) |
|---|---|---|
| Day 5 | 27 | 54 |
| Day 6 | 54 | 54 |
| Day 7 | 54 | 54 |
| Day 8 | 54 | 54 |
| Day 9 | 54 | 108 |
| Day 10 | 90 | 108 |
| Day 11 | 90 | 108 |
| Day 12 | 108 | 108 |
| Day 13 | 108 | 108 |
| Day 14 | 108 | 108 |
| Day 15 | 108 | 108 |
| Day 16 | 108 | 162 |
| Day 17 | 162 | 162 |

48. The method of any one of embodiments 1-47, wherein after said treating the patient experiences a substantial reduction in cough compared to prior to said treating.

49. The method of any one of embodiments 1-48, wherein after said treating the patient experiences a reduction of cough that is characterized by an at least 1.3 point decline in the total score on the patient's Leicester Cough Questionnaire score.

50. The method of any one of embodiments 1-49, wherein after said treating the patient experiences a reduction of cough that is characterized by at least a 30% reduction in daytime cough frequency measured using cough count monitor device.

51. The method of any one of embodiments 1-50, wherein after said treating the patient experiences a reduction of cough severity that is characterized by at least a three point reduction in Numerical Rating Scale cough (NRS) value.

52. The method of any one of embodiments 1-51, wherein after said treating the patient experiences a reduction in cough that is characterized by at least a 4 point improvement in cough quality of life questionnaire (CQLQ) total value.

53. The method of any one of embodiments 1-52, wherein after said treating the patient experiences a reduction of cough that is characterized by at least a 5 point reduction in the patient's St. George's Questionnaire for the IPF population (SGRQ-I) total score.

54. The method of any one of embodiments 1-53, wherein after said treating the patient experiences a reduction of cough that is characterized by at least a one point reduction in each of the components of the patient's St. George's Questionnaire (SGRQ-I) score.

55. The method of any one of embodiments 1-54, wherein after said treating the patient experiences a reduction of cough that is characterized by at least a 1.0 point reduction in the EXACT-Respiratory Symptoms (E-RS™) cough subscale score.

56. The method of any one of embodiments 1-55, wherein after said treating the patient experiences a reduction of cough that is characterized by at least a 1.0 point reduction in the EXACT-Respiratory Symptoms (E-RS™) chest symptoms subscale score.

57. The method of any one of embodiments 1-56, wherein after said treating the patient experiences a substantial reduction in breathlessness compared to prior to said treating.

58. The method of any one of embodiments 1-57, wherein after said treating the patient experiences a reduction of breathlessness that is characterized by at least a 1.0 point reduction in the EXACT-Respiratory Symptoms (E-RS™) breathlessness subscale score.

59. The method of any one of embodiments 1-58, wherein after said treating the patient experiences a substantial reduction in dyspnea compared to prior to said treating.

60. The method of any one of embodiments 1-59, wherein after said treating the patient experiences a reduction of dyspnea that is characterized by at least a 1.0 point reduction in the EXACT-Respiratory Symptoms (E-RS™) breathlessness subscale score connected to activity.

61. The method of any one of embodiments 1-60, wherein after said treating the patient experiences a reduction of dyspnea that is characterized by at least a one point change in the Borg dyspnea scale value total score.

62. The method of any one of embodiments 1-61, wherein after said treating the patient experiences a reduction of dyspnea that is characterized by at least a one point change in any of the Borg dyspnea scale domains (sensory-perceptual, affective distress or symptom impact).

63. The method of any one of embodiments 1-62, wherein after said treating the patient experiences a reduction of dyspnea that is characterized by at least a 3 point reduction in the numerical rating scale dyspnea value.

64. The method of any one of embodiments 1-63, wherein after said treating the patient experiences a reduction of dyspnea that is characterized by at least a one category change in the Modified Medical Research Council Scale.

65. The method of any one of embodiments 1-64, wherein after said treating the patient experiences a reduction of dyspnea that is characterized by at least a one category change in at least one of the 7 questions of the PROMIS Pool v1.0 Dyspnea Emotional Response Scale.

66. The method of any one of embodiments 1-65, wherein after said treating the patient experiences a reduction of dyspnea that is characterized by at least a one category change in at least one of the 10 questions of the PROMIS Item Bank v1.0 Dyspnea Severity-Short Form 10a Scale.

67. The method of any one of embodiments 1-66, wherein after said treatment the patient experiences a reduction of dyspnea that is characterized by at least a one category change in at least one of the 4 items or a one category change in the question "I have been short of breath" of the PROMIS Item Bank v1.0 Dyspnea Characteristics Scale compared to prior to the treatment.

68. The method of any one of embodiments 1-67, wherein after said treating the patient experiences a substantial reduction in fatigue.

69. The method of any one of embodiments 1-68, wherein after said treating the patient experiences a reduction of fatigue that is characterized by at least a one category change in at least one of the 7 questions of the PROMIS Item Bank v1.0 Fatigue Short Form 7a Scale.

70. The method of any one of embodiments 1-69, wherein after said treating the patient experiences a substantial reduction in the rate of pulmonary fibrosis compared to prior to said treating as quantified by objective measures (chest x-ray, pulmonary function tests, etc.).

71. The method of any one of embodiments 1-70, wherein after said treating the patient experiences a substantial reduction in the hospitalization rate based on improvement in the dyspnea, breathlessness or cough status.

72. The method of any one of embodiments 1-12 and 24-71, wherein after said treating the patient experiences a substantial reduction in morbidity and mortality as a result of the lessening incidence of acute exacerbations of IPF (AE-IPF) related to deterioration of lung function and/or lessening of breathing difficulties secondary to an interruption in the "dyspnea cycle" positive feedback loop of progressively more frequent episodes of dyspnea of increasing intensity.

73. The method of any one of embodiments 1-12 and 24-72, wherein the nalbuphine or a pharmaceutically acceptable salt or ester thereof is administered in conjunction with one or more drugs that treat IPF cough, breathlessness, or dyspnea.

74. The method of embodiment 73, wherein the one or more drugs that treat IPF cough, breathlessness, or dyspnea is selected from the group consisting of pirfenidone, nintedanib, N-acetylcysteine, cromolyn sodium, thalidomide, gefapixant, serlopitant, and orvepitant.

75. The method of any one of embodiments 1-74, wherein the nalbuphine or a pharmaceutically acceptable salt or ester thereof is nalbuphine hydrochloride.

76. The method of any one of embodiments 1-75, wherein the nalbuphine or a pharmaceutically acceptable salt or ester thereof is in the form of an extended release oral dosage form.

77. The method of any one of embodiments 1-76, wherein the nalbuphine or a pharmaceutically acceptable salt or ester thereof is administered in a formulation comprising nalbuphine hydrochloride, mannitol, hydroxypropyl cellulose, locust bean gum, xanthan gum, calcium sulfate dihydrate, fumaric acid and magnesium stearate.

78. The method of any one of embodiments 1-77, wherein the nalbuphine is administered orally.

79. The method of any one of embodiments 1-77, wherein the nalbuphine is administered by inhalation.

What is claimed is:

1. A method of treating idiopathic pulmonary fibrosis (IPF) cough comprising orally administering to a patient in need thereof an effective amount of nalbuphine or a pharmaceutically acceptable salt or ester thereof.

2. The method of claim 1, wherein the IPF cough is chronic cough.

3. The method of claim 1, wherein the administration provides in the patient a mean $AUC_{tau}$ from about 40 ng·hr/mL to about 800 ng·hr/mL.

4. The method of claim 1, wherein the administration provides in the patient a mean $AUC_{tau}$ from about 40 ng·hr/mL to about 200 ng·hr/mL.

5. The method of claim 1, wherein the administration provides in the patient a mean $C_{max}$ of from about 5 ng/mL to about 85 ng/mL.

6. The method of claim 1, wherein the administration provides in the patient a mean $C_{max}$ of from about 6.28 ng/mL to about 82.78 ng/mL.

7. The method of claim 1, wherein a total daily dose of about 27 mg to about 324 mg of an Equivalent Amount of Nalbuphine Free Base is administered.

8. The method of claim 1, wherein a total daily dose of about 324 mg of an Equivalent Amount of Nalbuphine Free Base is administered.

9. The method of claim 1, wherein an Equivalent Amount of Nalbuphine Free Base of about 27 mg to about 162 mg is administered twice daily.

10. The method of claim 1, wherein about 27 mg of an Equivalent Amount of Nalbuphine Free Base is administered once a day.

11. The method of claim 1, wherein about 27 mg of an Equivalent Amount of Nalbuphine Free Base is administered twice a day.

12. The method of claim 1, wherein about 54 mg of an Equivalent Amount of Nalbuphine Free Base is administered twice a day.

13. The method of claim 1, wherein about 108 mg of an Equivalent Amount of Nalbuphine Free Base is administered twice a day.

14. The method of claim 1, wherein about 162 mg of an Equivalent Amount of Nalbuphine Free Base is administered twice a day.

15. The method of claim 1, wherein the administering is for at least 1 week.

16. The method of claim 1, wherein the administering is for at least 8 weeks, 10 weeks, 12 weeks, 24 weeks or 52 weeks.

17. The method of claim 1, further comprising titrating the dose of nalbuphine or a pharmaceutically acceptable salt or ester thereof for at least one week until a steady state is achieved in the patient.

18. The method of claim 17, wherein the nalbuphine is administered at an initial dose of from about 14 mg to about 27 mg once a day and then titrated to an effective dose.

19. The method of claim 17, wherein the titrating further comprises administering an initial dose of about 27 mg once or twice a day.

20. The method of claim 17, wherein the titrating comprises administering nalbuphine or a pharmaceutically acceptable salt or ester thereof in increments ranging from about 13 mg to about 54 mg.

21. The method of claim 17, wherein the titrating comprises administering nalbuphine according to the dose schedule provided in the following table (expressed as Equivalent Amount of Nalbuphine Free Base):

| Day | AM dosage (mg) | PM dosage (mg) |
| --- | --- | --- |
| Day 1 | 0 | 27 |
| Day 2 | 0 | 27 |
| Day 3 | 27 | 27 |
| Day 4 | 27 | 27 |
| Day 5 | 27 | 54 |
| Day 6 | 54 | 54 |
| Day 7 | 54 | 54 |
| Day 8 | 54 | 54 |
| Day 9 | 54 | 108 |
| Day 10 | 108 | 108 |
| Day 11 | 108 | 108 |
| Day 12 | 108 | 108 |
| Day 13 | 108 | 108 |
| Day 14 | 108 | 108 |
| Day 15 | 108 | 108 |
| Day 16 | 108 | 162 |
| Day 17 | 162 | 162. |

22. The method of claim 1, wherein after the treating the patient experiences a reduction of cough that is characterized by at least a 30% reduction in daytime cough frequency measured using cough count monitor device compared to prior to the treating.

23. The method of claim 1, wherein after the treating the patient experiences a reduction of cough that is characterized by at least a 50% reduction in daytime cough frequency measured using cough count monitor device compared to prior to the treating.

24. The method of claim 1, wherein the nalbuphine or a pharmaceutically acceptable salt or ester thereof is nalbuphine hydrochloride.

25. The method of claim 1, wherein the nalbuphine or a pharmaceutically acceptable salt or ester thereof is in the form of an extended release oral dosage form.

26. The method of claim 1, wherein the nalbuphine or a pharmaceutically acceptable salt or ester thereof is administered in combination with one or more therapeutic agents selected from nintedanib and pirfenidone.

* * * * *